(12) United States Patent
Durette et al.

(10) Patent No.: US 6,903,075 B1
(45) Date of Patent: Jun. 7, 2005

(54) HETEROCYCLIC AMIDE COMPOUNDS AS CELL ADHESION INHIBITORS

(75) Inventors: Philippe L. Durette, New Providence, NJ (US); Malcolm MacCoss, Freehold, NJ (US); William K. Hagmann, Westfield, NJ (US); Sander G. Mills, Scotch Plains, NJ (US); Richard A. Mumford, Red Bank, NJ (US); Jack A. Schmidt, Greenbrook, NJ (US); Gail A. Van Riper, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/086,327

(22) Filed: May 28, 1998

Related U.S. Application Data

(60) Provisional application No. 60/066,525, filed on Nov. 25, 1997, and provisional application No. 60/047,856, filed on May 29, 1997.

(51) Int. Cl.$^7$ .................................................. C07K 5/06
(52) U.S. Cl. ........................................ 514/19; 548/535
(58) Field of Search ............................ 514/19; 548/535

(56) References Cited

U.S. PATENT DOCUMENTS

| | | | |
|---|---|---|---|
| 4,350,698 A | 9/1982 | Gleason et al. | 514/308 |
| 4,482,486 A | 11/1984 | Brtnik et al. | 260/112.5 |
| 5,219,851 A | 6/1993 | Hamilton et al. | 514/233.5 |
| 5,229,381 A | 7/1993 | Doherty et al. | 514/210 |
| 5,424,329 A | 6/1995 | Boschelli et al. | 514/418 |
| 5,430,023 A | 7/1995 | Gesellchen | 514/18 |
| 5,439,930 A | 8/1995 | Seredenin et al. | 514/423 |
| 5,510,332 A | 4/1996 | Kogan et al. | 514/14 |
| 5,602,099 A | 2/1997 | Schiller | 514/18 |
| 5,688,913 A * | 11/1997 | Arrhenius et al. | 530/330 |
| 6,291,453 B1 | 9/2001 | Ashwell et al. | 514/227.5 |
| 6,362,341 B1 | 3/2002 | Thorsett et al. | 548/200 |
| 6,423,688 B1 | 7/2002 | Thorsett et al. | 514/19 |
| 6,489,300 B1 * | 12/2002 | Thorsett et al. | 514/19 |
| 6,492,421 B1 | 12/2002 | Thorsett et al. | 514/562 |
| 6,559,127 B1 | 5/2003 | Dappen et al. | 514/19 |
| 6,583,139 B1 | 6/2003 | Thorsett et al. | 514/227.5 |
| 6,586,602 B2 | 7/2003 | Thorsett et al. | 548/200 |

FOREIGN PATENT DOCUMENTS

| | | |
|---|---|---|
| EP | 0190852 | 8/1986 |
| EP | 0 337 549 | 6/1989 |
| EP | 0 443132 | 12/1990 |
| EP | 0 618 221 | 5/1994 |
| EP | 0 696 593 A2 | 2/1996 |
| WO | WO 92/04369 | 3/1992 |
| WO | WO 95/15973 | 6/1995 |
| WO | WO 96/01644 | 1/1996 |
| WO | WO 96/06108 | 2/1996 |
| WO | WO 96/20216 | 7/1996 |
| WO | WO 96/22966 | 8/1996 |
| WO | WO 96/40641 | 12/1996 |
| WO | WO 96/40781 | 12/1996 |
| WO | WO 97/02289 | 1/1997 |
| WO | WO 97/03094 | 1/1997 |
| WO | WO 98/54207 | 12/1998 |
| WO | WO 99/06390 | 2/1999 |
| WO | 99/06391 * | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |

OTHER PUBLICATIONS

Dutta (Journal of Peptide Science 6, 321–324, 2000).*
Komoriya, Akira (J. Biol. Chem. 266 (23), 15075–15079, 1991).*
Haworth, Duncan (Br. J. Pharmacol. 126(8), 1751–1760, 1999).*
Haubner (J. Am. Chem. Soc. 118, 7881, 1996).*
Lin (J Med Chem 42, 920, 1999).*
El–Naggar, Acta. Pharm. Jugosl 35, 15, 1985.*
Gerardo Byk, et al., *Bioorganic&Medicinal Chemistry Letters*, vol. 5, No. 22, pp. 2677–2682, (1995).
Journal of the Chinese Chemical Society, 1990, 37, 299–305, Selective Alkaline Protease Catalyzed Hydrolysis of Peptide Esters.
J. Serb. Chem. Soc. 52 (I) 17–24 (1987) Synthesis of Some 4–Methoxycimamic Acid–2–Sulphonylamino Acid Derivatives and their Antimicrobial Activity.
Proc. Indian nain. Sci–Acad., 60, A, No. 2, 1994, pp. 433–439 Synthesis and Antimicrobial Activity of Some New 7–Methoxy–4–Methylcoumarin–6–Sulphonyl–Amino Acid Derivatives (1993).
Acta Pharm. Jugosl. 33 (1983) 103–110 Synthesis and Biological Activity of Some New Quinoline–8–Sulphonylamino Acid and Dipeptide Derivatives.
Pharmazie, 1986 41(6), pp 378–81.
J. Med. Chem. 36(26) 1993 pp 4201–4207.
Bioorg. & Med. Chem. vol. 6 No. 21 1996 pp 2495–2500.
J. Med. Chem. 1997, 40 pp 3359–3368.
J. Med. Chem. 1995, vol. 38, No. 22 pp 4597–4614.
Pharmazie, 1986 41 (4)m, pp 233–235.

* cited by examiner

*Primary Examiner*—Jon Weber
*Assistant Examiner*—David Lukton
(74) *Attorney, Agent, or Firm*—Mollie M. Yang; David L. Rose

(57) ABSTRACT

Compounds of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

12 Claims, No Drawings

HETEROCYCLIC AMIDE COMPOUNDS AS CELL ADHESION INHIBITORS

CROSS REFERENCE TO RELATED APPLICATIONS

This application is based on, and claims priority from provisional applications 60/047,856 filed 29 May 1997 and 60/066,525 filed 25 Nov. 1997, where are hereby incorporated by reference in their entirety.

SUMMARY OF THE INVENTION

The compounds of the present invention are antagonists of the VLA-4 integrin ("very late antigen-4"; CD49d/CD29; or $\alpha_4\beta_1$) and/or the $\alpha4\beta7$ integrin (LPAM-1 and $\alpha_4\beta_p$), thereby blocking the binding of VLA-4 to its various ligands, such as VCAM-1 and regions of fibronectin and/or $\alpha4\beta7$ to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4 and/or $\alpha4\beta7$ binding and cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, and atherosclerosis.

BACKGROUND OF THE INVENTION

The present invention relates to heterocyclic amide derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell—cell and cell-matrix interactions are mediated through several families of cell adhesion molecules (CAMs) including the selecting, integrins, cadherins and immunoglobulins. CAMs play an essential role in both normal and pathophysiological processes. Therefore, the targeting of specific and relevant CAMs in certain disease conditions without interfering with normal cellular functions is essential for an effective and safe therapeutic agent that inhibits cell—cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, Cell, 67, 1033 (1991); T. A. Springer, Cell, 16, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, NY, 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell—cell and cell-matrix interactions of of these cell types (see M. E. Hemler, "VLA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to pro-inflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-4/CS-1 interactions in inflammatory conditions has been proposed (see M. J. Elices, "The integrin $\alpha_4\beta_1$ (VLA-4) as a therapeutic target" in Cell Adhesion and Human Disease, Ciba Found. Symp., John Wiley & Sons, NY, 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract (see C. M. Parker et al., Proc Natl. Acad. Sci. USA, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al., J. Immunol., 152, 3282 (1994)). MadCAM-1 can be induced in vitro by proinflammatory stimuli (See E. E. Sikorski et al. J. Immunol., 151, 5239 (1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neurology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995)); iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." J. Rheumatol., 23, 12 (1996)); iv)

adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", *J. Clin. Invest.*, 93, 1700 (1994), A. Jakubowski et al., "Vascular cell adhesion molecule-Ig fusion protein selectively targets activated $\alpha_4$-integrin receptors in vivo: Inhibition of autoimmune diabetes in an adoptive transfer model in nonobese diabetic mice." *J. Immunol.*, 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", *Transplant. Proc.*, 26, 867 (1994) and S. Molossi et al., "Blockade of very late antigen-4 integrin binding to fibronectin with connecting segment-1 peptide reduces accelerated coronary arteripathy in rabbit cardiac allografts." *J. Clin Invest.*, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin $\alpha$-4 subunit inhibit the murine contact hypersensitivity response." *Eur. J. Immunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of $\alpha$4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996; xii) inhibition of TH2 T-cell cytokine production including IL-4 and IL-5 by VLA-4 antibodies which would attenuate allergic responses (J. Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; acute respiratory distress syndrome (ARDS); atherosclerotic plaque formation; restenosis; uveitis and circulatory shock (for examples, see A. A. Postigo et al., "The $\alpha_4\beta_1$/CAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89, 375 (1996)).

At present, there is a humanized monoclonal antibody (Antegren® Athena Neurosciences/Elan) against VLA-4 in clinical development for the treatment of "flares" associated with multiple sclerosis and a humanized monoclonal antibody (ACT-1®/LDP-02 LeukoSite) against $\alpha_4\beta_7$ in clinical development for the treatment of inflammatory bowel disease. Several peptidyl antagonists of VLA-4 have been described (D. Y. Jackson et al., "Potent $\alpha$4$\beta$1 peptide antagonists as potential anti-inflammatory agents", *J. Med. Chem.*, 40, 3359 (1997); H. N. Shroff et al., "Small peptide inhibitors of $\alpha$4$\beta$7 mediated MadCAM-1 adhesion to lymphocytes", *Bioorg. Med. Chem. Lett.*, 6, 2495 (1996); U.S. Pat. No. 5,510,332, WO97/03094, WO97/02289, WO96/40781, WO96/22966, WO96/20216, WO96/01644, WO96/06108, WO95/15973). There is one report of non-peptidyl inhibitors of the ligands for $\alpha_4$-integrins (WO96/31206). There still remains a need for low molecular weight, specific inhibitors of VLA-4- and $\alpha$4$\beta$7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and $\alpha$4$\beta$7 binding and cell adhesion and activation.

DETAILED DESCRIPTION OF THE INVENTION

One aspect of the present invention provides a method for the treatment of diseases, disorders, conditions or symptoms mediated by cell adhesion in a mammal which comprises administering to said mammal an effective amount of a compound Formula I:

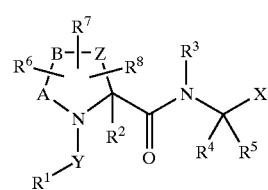

or a pharmaceutically acceptable salt thereof wherein:
$R^1$ is
1) $C_{1-10}$alkyl,
2) $C_{2-10}$alkenyl,
3) $C_{2-10}$alkynyl,
4) Cy,
5) Cy-$C_{1-10}$alkyl,
6) Cy-$C_{2-10}$alkenyl,
7) Cy-$C_{2-10}$alkynyl,
wherein alkyl, alkenyl, and alkynyl are optionally substituted with one to four substituents independently selected from $R^a$; and Cy is optionally substituted with one to four substituents independently selected from $R^b$;
$R^2$ is
1) hydrogen,
2) $C_{1-10}$alkyl,
3) $C_{2-10}$alkenyl,
4) $C_{2-10}$alkynyl,
5) aryl, 6) aryl-$C_{1-10}$alkyl,
7) heteroaryl,
8) heteroaryl-$C_{1-10}$alkyl,
wherein alkyl, alkenyl, and alkynyl are optionally substituted with one to four substituents independently selected from $R^a$; and aryl and heteroaryl optionally substituted with one to four substituents independently selected from $R^b$;

$R^3$ is
1) hydrogen,
2) $C_{1-10}$ alkyl,
3) Cy, or
4) Cy-$C_{1-10}$ alkyl,
wherein alkyl is optionally substituted with one to four substituents independently selected from $R^a$; and Cy is optionally substituted with one to four substituents independently selected from $R^b$;

$R^4$ is
1) hydrogen,
2) $C_{1-10}$alkyl,
3 $C_{2-10}$alkenyl,
4) $C_{2-10}$alkynyl,
5) Cy,
6) Cy-$C_{1-10}$alkyl,
7) Cy-$C_{2-10}$alkenyl,
8) Cy-$C_{2-10}$alkynyl,
wherein alkyl, alkenyl and alkynyl are optionally substituted with one to four substituents selected from phenyl and RX, and Cy is optionally substituted with one to four substituents independently selected from RY; or $R^3$, $R^4$ and the atoms to which they are attached together form a mono- or bicyclic ring containing 0–2 additional heteroatoms selected from N, O and S;

$R^5$ is
1) hydrogen,
2) $C_{1-10}$alkyl,
3) $C_{2-10}$alkenyl,
4) $C_{2-10}$alkynyl,
5) aryl,
6) aryl-$C_{1-10}$alkyl,
7) heteroaryl,
8) heteroaryl-$C_{1-10}$alkyl,
wherein alkyl, alkenyl and alkynyl are optionally substituted with one to four substituents selected from RX, and aryl and heteroaryl are optionally substituted with one to four substituents independently selected from RY; or $R^4$, $R^5$ and the carbon to which they are attached form a 3–7 membered mono- or bicyclic ring containing 0–2 heteroatoms selected from N, O and S;

$R^6$, $R^7$, and $R^8$ are each independently selected from the group consisting of
1) a group selected from $R^d$, and
2) a group selected from $R^x$; or
two of $R^6$, $R^7$, and $R^8$ and the atom to which both are attached, or two of $R^6$, $R^7$, and $R^8$ and the two adjacent atoms to which they are attached, together form a 5–7 membered saturated or unsaturated monocyclic ring containing zero to three heteroatoms selected from N, O or S, $R^a$ is
1) Cy, or
2) a group selected from Rx;
wherein Cy is optionally substituted with one to four substituents independently selected from $R^c$;

$R^b$ is
1) a group selected from $R^a$,
2) $C_{1-10}$alkyl,
3) $C_{2-10}$ alkenyl,
4) $C_{2-10}$ alkynyl,
5) aryl $C_{1-10}$alkyl,
6) heteroaryl $C_{1-10}$ alkyl,
wherein alkyl, alkenyl, alkynyl, aryl, heteroaryl are optionally substituted with a group independently selected from $R^c$;

$R^c$ is
1) halogen,
2) $NO_2$,
3) $C(O)OR^f$,
4) $C_{1-4}$alkyl,
5) $C_{1-4}$alkoxy,
6) aryl,
7) aryl $C_{1-4}$alkyl,
8) aryloxy,
9) heteroaryl,
10) NRfRg,
11) NRfC(O)Rg,
12 NRfC(O)NRfRg, or
13) CN;

$R^d$ and $R^e$ are independently selected from hydrogen, $C_{1-10}$alkyl, $C_{2-10}$ alkenyl, $C_{2-10}$alkynyl, Cy and Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy-$C_{1-10}$alkyl wherein Cy is optionally substituted with $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is
1) hydrogen,
2) $C_{1-10}$alkyl,
3) $C_{2-10}$alkenyl,
4) $C_{2-10}$alkynyl,
5) cyano,
6) aryl,
7) aryl $C_{1-10}$alkyl,
8) heteroaryl,
9) heteroaryl $C_{1-10}$alkyl, or
10) —$SO_2R^i$;
wherein alkyl, alkenyl, and alkynyl are optionally substituted with one to four substituents independently selected from $R^a$; and aryl and heteroaryl are each optionally substituted with one to four substituents independently selected from $R^b$;

$R^i$
1) $C_{1-10}$alkyl,
2) $C_{2-10}$alkenyl,
3) $C_{2-10}$alkynyl, or
4) aryl;
wherein alkyl, alkenyl, alkynyl and aryl are each optionally substituted with one to four substituents independently selected from $R^C$;

$R^x$ is
1) —$OR^d$,
2) —$NO_2$,
3) halogen
4) —$S(O)_m R^d$,
5) —$SR^d$,
6) —$S(O)_2 OR^d$,
7) —$S(O)_m NR^d R^e$,
8) —$NR^d R^e$,
9) —$O(CR^f R^g)_n NR^d R^e$,
10) —$C(O)R^d$,
11) —$CO_2 R^d$,
12) —$CO_2(CR^f R^g)_n CONR^d R^e$,
13) —$OC(O)R^d$,
14) —CN,
15) —$C(O)NR^d R^e$,
16) —$NR^d C(O)R^e$,
17) —$OC(O)NR^d R^e$,
18) —$NR^d C(O)OR^e$,
19) —$NR^d C(O)NR^d R^e$,
20) —$CR^d(N—OR^e)$,
21) —$CF_3$,
22) oxo,
23) $NR^d C(O)NR^d \, SO_2 R^i$,
24) $NR^d S(O)_m R^e$,
25) —$OS(O)_2 OR^d$, or
26) —$OP(O)(OR^d)_2$;

$R^y$ is
1) a group selected from $R^x$,
2) $C_{1-10}$ alkyl,
3) $C_{2-10}$ alkenyl,
4) $C_{2-10}$ alkynyl,
5) aryl $C_{1-10}$alkyl,
6) heteroaryl $C_{1-10}$ alkyl,
7) cycloalkyl,
8) heterocyclyl;

wherein alkyl, alkenyl, alkynyl and aryl are each optionally substituted with one to four substituents independently selected from RX;
Cy is cycloalkyl, heterocyclyl, aryl, or heteroaryl;
m is an integer from 1 to 2;
n is an integer from 1 to 10;
X is
1) —$C(O)OR^d$,
2) —$P(O)(OR^d)(OR^e)$
3) —$P(O)(Rd)(OR^e)$
4) —$S(O)_m OR^d$,
5) —$C(O)NR^d R^h$, or
6) -5-tetrazolyl;
Y is
1) —C(O)—,
2) —O—C(O)—,
3) —$NR^e$—C(O)—,
4) —$S(O)_2$—,
5) —$P(O)(OR^4)$ or
6) C(O)C(O);
Z and A are independently selected from —C— and —C≡C—;

B is selected from the group consisting of
1) a bond,
2) —C—
3) —C—C—,
3) —C=C—,
4) a heteroatom selected from the group consisting of nitrogen, oxygen, and sulfur; and
5) —$S(O)_m$—.

In one embodiment of the method compounds of Formula I are those wherein Y is $S(O)_2$ and $R^1$ is $C_{1-10}$alkyl, Cy or Cy-$C_{1-10}$ alkyl wherein alkyl is optionally substituted with one to two substituents independently selected from $R^a$, and Cy is optionally substituted with one to four substituents independently selected from $R^b$.

In another embodiment of the method compounds of Formula I are those of formula Ia, Ib or Ic.

In another embodiment, the cell adhesion is mediated by VLA-4.

Another aspect of the present invention provides novel compounds of Formula Ia:

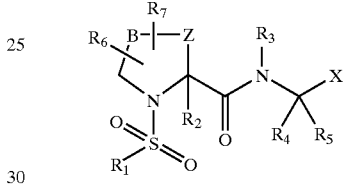

Ia or a pharmaceutically acceptable salt thereof, wherein the variables are as defined under formula I with the proviso that $R^6/R^7$ is not oxo when attached to the carbon between N and B, and with the further proviso that when B and Z are each C, $R^2$, $R^3$, $R^6$, and $R^7$ are each H, then $R^1$ is other than phenyl, 4-methylphenyl and 5-($NR^d R^e$)naphthyl.

In one subset of Formula Ia are compounds wherein Z is C.

In another subset of Formula Ia are compounds wherein B is C, C=C, C—C or S. Preferably B is C or C=C.

In another subset of Formula Ia are compounds wherein X is $C(O)OR^d$.

In another subset of Formula Ia are compounds wherein $R^1$ is $C_{1-10}$alkyl, Cy or Cy-$C_{1-10}$alkyl wherein alkyl is optionally substituted with one to two substituents independently selected from $R^a$, and Cy is optionally substituted with one to four substituents independently selected from $R^b$. For the purpose of $R^1$ Cy is preferably aryl optionally substituted with one to four substituents selected from $R^b$. More preferred $R^1$ is phenyl with a substituent on the 3-position and optionally a second substituent; the more preferred substituents are selected from $C_{1-10}$alkoxy, halogen, cyano, and trifluoromethyl.

In another subset of Formula Ia are compounds wherein $R^2$ is H or $C_{1-6}$alkyl. Preferred $R^2$ is H or $C_{1-3}$alkyl, more preferably H or methyl.

In another subset of Formula Ia are compounds wherein $R^3$ is H or $C_{1-6}$alkyl. Preferred $R^3$ is H or $C_{1-3}$alkyl, more preferably H or methyl.

In another subset of Formula Ia are compounds wherein $R^5$ is H and $R^4$ is $C_{1-10}$alkyl or Cy-$C_{1-10}$alkyl, wherein alkyl is optionally substituted with one to four substituents selected from phenyl and Rx, and Cy is optionally substituted with one to four substituents independently selected from $R^y$; or $R^4$, $R^5$ and the carbon to which they are attached together form a 3–7 membered mono- or bicyclic carbon only ring. For the purpose of $R^4$, Cy is preferably aryl, more preferably phenyl. In a preferred embodiment, $R^4$ is phenyl-$C_{1-3}$alkyl, wherein phenyl is optionally substituted with one or two groups selected from $R^y$.

In one embodiment of compounds of formula Ia are compounds of formula Ib:

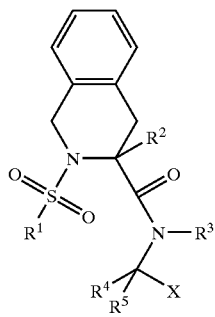

Ib wherein $R^2$ is H or $C_{1-6}$ alkyl, and $R^1$, $R^3$, $R^4$ and $R^5$ are as defined previously under Formula I. In a preferred embodiment X is $CO_2H$; $R^1$ is aryl optionally substituted with one to four substituents selected from $R^b$; $R^2$ is H; $R^3$ is H or $C_{1-3}$ alkyl; $R^4$ is phenyl-$C_{1-13}$alkyl, wherein phenyl is optionally substituted with one or two groups selected from $R^y$; and $R^5$ is H.

Another embodiment of compounds of Formula Ia are compounds of the formula Ic:

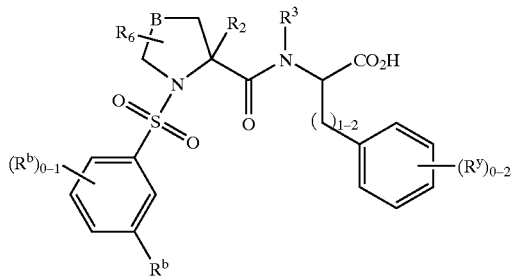

Ic wherein $R^2$ is H or $C_{1-3}$ alkyl, $R^6$ is H, $C_{1-6}$ alkyl, aryl, $OR^d$, $SR^d$, $NR^dR^e$, or $NR^dC(O)Re$, B is S, C=C, C or C—C, $R^3$ is H or $C_{1-6}$alkyl, Rb and $R^y$ are as defined under Formula I. Preferably B is C and Rb is halogen, $C_{1-10}$alkoxy, cyano, or trifluoromethyl.

The present compounds are generally composed of three domains: 1) an acyl (including sulfonyl) moiety, 2) a cyclic amino acid 1, and 3) amino acid 2, and are named in a manner similar to that used to name oliogopeptides. Representative names used herein and their corresponding structures are shown below (without the stereochemistry) to illustrate the nomenclature used in the application.

N-(3,4-dimethoxybenzenesulfonyl)-1,2,3,4-tetrahydroisoquinoline-3(S)-carbonyl-(L)-leucine

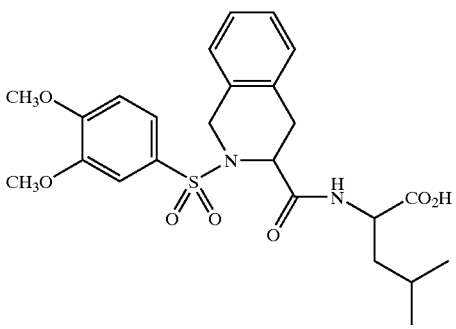

N-(3,5-dichlorobenzenesulfonyl)-(L)-pipecolyl-(L)-homophenylalanine

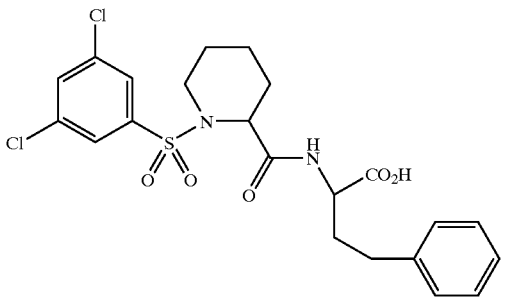

N-(3-fluorobenzenesulfonyl)-(L)-4(R)-hydroxyprolyl-(L)-tyrosine, O-tert-butyl ether

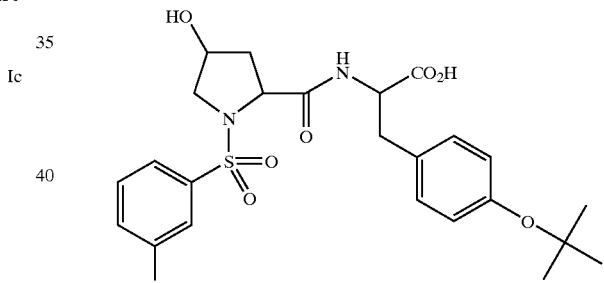

N-[4-(N'-2-toluylureido)phenylacetyl-(L)-prolyl-(L)-norleucine

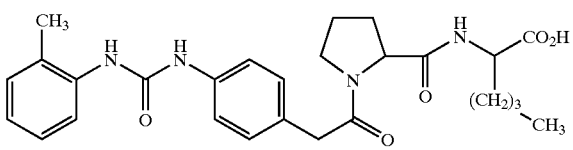

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon—carbon double bond, and which may be linear or branched or -combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon—carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers-Diastereomers-Geometric Isomers-Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha4\beta7$ integrin makes them useful for preventing or reversing the symptoms, disorders or diseases induced by the binding of VLA-4 and or $\alpha4\beta7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha4\beta7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, and (19) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients: In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
| --- | --- |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-500 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as P2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone, pioglitazone, englitazone, MCC-555, BRL49653 and the like); (1) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of the present invention may be prepared by procedures illustrated in the accompanying schemes. In the first method (Scheme 1), a resin-based synthetic strategy is outlined where the resin employed is represented by the ball ●. An N-Fmoc-protected amino acid derivative A (Fmoc=fluorenylmethoxycarbonyl) is loaded on to the appropriate hydroxyl-containing resin using dicyclohexylcarbodiimide (DCC) and 1-hydroxybenzotriazole (HOBt) in dimethylformamide (DMF) to give B. The Fmoc protecting group is removed with piperidine in DMF to yield free amine C. The next Fmoc-protected amino acid derivative D is coupled to C employing standard peptide (in this instance, 2-(1H-benzotriazol-1-yl)-1,1,3,3-tetramethyluronium hexafluorophosphate (HBTU), HOBt, and N,N-diisopropylethylamine (DIEA) in DMF) to yield dipeptide E. The Fmoc group is removed with piperidine in DMF to yield the free amine F. An acid chloride or isocyanate derivative is reacted with F in the presence of DIEA to yield G. The final product is removed from the resin with strong acid (in this instance, trifluoroacetic acid (TFA) in the presence of thioanisole and dithiane) to yield compounds of the present invention H.

In the second method (Scheme 2), standard solution phase synthetic methodology is outlined. An N-Boc-protected amino acid derivative A (Boc=tert-butyloxycarbonyl) is treated with tert-butyl 2,2,2-trichloroacetimidate in the presence of boron trifluoride etherate to yield tert-butyl ester followed by treatment with strong acid (HCl in ethyl acetate or sulfuric acid in t-butyl acetate) to yield the free amine n which is subsequently coupled to Cbz-protected amino acid derivative C (Cbz=carbobenzyloxy) in the presence of 1-(3-dimethylaminopropyl)-3-ethylcarbodiimide hydrochloride (EDC), HOBt, and N-methylmorpholine (NMM) in methylene chloride (Methylene chloride) to yield dipeptide D. Catalytic hydrogenation of D in the presence of a palladium-on-carbon (Pd/C) catalyst yields E Reaction of E with an acylchloride or isocyanate in the presence of DIEA and 4-dimethylaminopyridine (DMAP) yields F which is subsequently reacted with strong acid (TFA) to yield the desired product G.

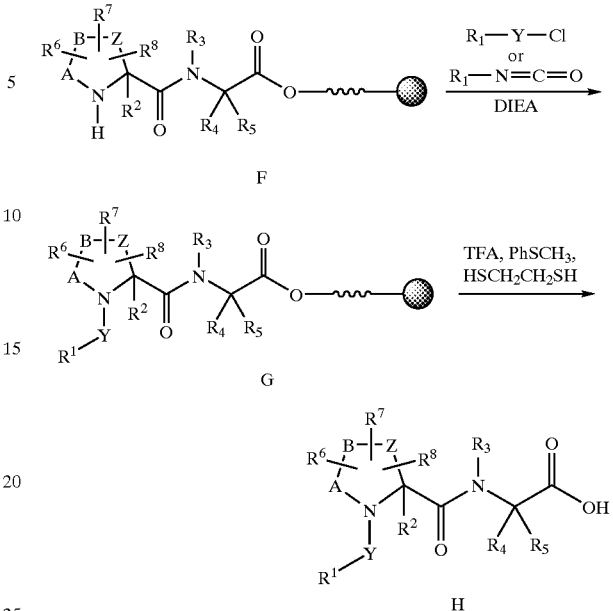

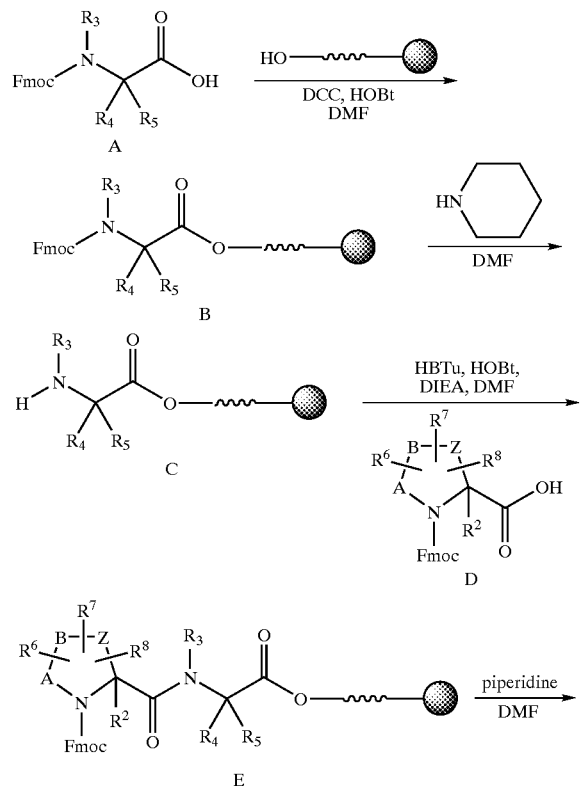

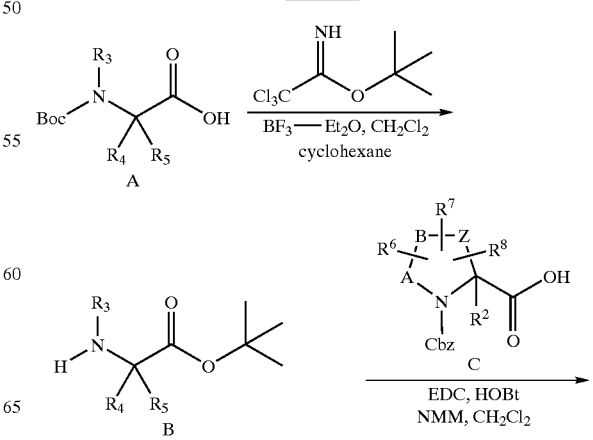

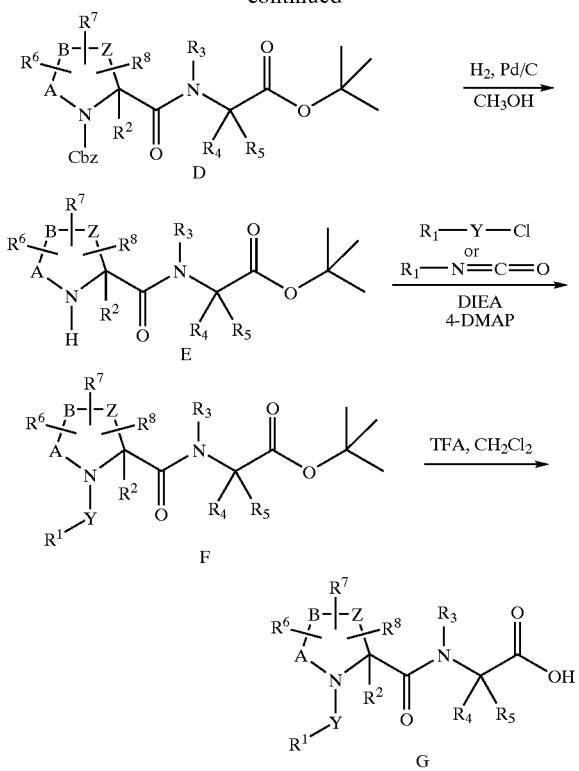

General Procedure for the Solid-Phase Synthesis of Compounds of Formula 1.

Step A. Loading of N-Fmoc-Amino Acid Derivatives onto Resins.

N-Fmoc-amino acids were loaded on either Wang® (Calbiochem-Novabiochem Corp.) or Chloro (2-chlorotrityl) resin. Wang® resin, typically 0.3 mmol, was washed with dimethylformamide three times. A solution of N-Fmoc-amino acid (0.3 mmol) in dimethylformamide (3 mL) was transferred to the pre-swollen Wang® resin. Dicyclohexylcarbodiimide (0.3 mmol) and 1-N-hydroxybenztriazole (0.3 mmol) was added and the mixture gently swirled for 2 hours. Following filtration, the resin was sequentially washed with dimethylformamide (3 times) and dichloromethane (3 times). The amino acid substitution value obtained after vacuum drying typically ranged between 0.07 to 0.1 mmol.

Alternatively, Chloro (2-chlorotrityl) resin, typically 0.2 mmol, was pre-swollen in dimethylformamide. A solution of N-Fmoc-amino acid (0.2 mmol) in dimethylformamide (3 ml) was added to the resin, followed by the addition of N,N-diisopropylethylamine(0.4 mmol). The resin was gently stirred for 2 hours, filtered and washed sequentially with dimethylformamide (3 times) and dichloromethane (3 times). The resin was finally washed with 10% methanol in dichloromethane and vacuum dried. The amino acid substitution value obtained after vacuum drying typically ranged between 0.05 to 0.1 mmol.

Step B. Deprotection of the N-Fmoc Group.

The N-Fmoc protecting group was removed from the resin from Step A by treatment with 20% piperidine in dimethylformamide for 30 minutes. Following filtration, the resin was washed sequentially with dimethylformamide (3 times), dichloromethane (1 time) and dimethylformamide (2 times) and used in the subsequent reaction.

Step C. Coupling of the Next N-Fmoc-Amino Acid Derivative

A solution of the next desired N-Fmoc-amino acid derivative (0.4 mmol) in dimethylformamide (2 mL) was mixed with 2-(1H-benzotriazol-1-yl)-1, 1,3,3-tetramethyluronium hexafluorophosphate (0.4 mmol), 1-hydroxybenzotriazole (0.4 mmol) and diisopropylethylamine (0.6 mmol). This solution was transferred to resin from Step B and typically allowed to react for 2 hours. Couplings were monitored by ninhydrin reaction. The coupling mixture was filtered and the resin washed with dimethylformamide (3 times) and used in the subsequent reaction.

Step D. Deprotection of the N-Fmoc Group.

The N-Fmoc protecting group was removed from the resin from Step C by the procedure described in Step B and used in the subsequent reaction.

Step E. Activation (or sulfonyl)ation) of the Terminal Amino Group.

The desired N-terminal capping reagent (sulfonyl) chloride or acyl chloride, or isocyanate) (0.4 mol) was dissolved in dimethylformamide (2 ml), mixed with N,N-diisopropylethylamine(0.8 mmol) and added to the resin from Step D. After approximately two hours, the resin was sequentially washed with dimethylformamide (3 times) and dichloromethane (3 times).

Step F. Cleavage of the Desired Products from the Resins.

The final desired products were cleaved from the resins from Step E by gently stirring with a solution of trifluoroacetic acid:thioanisole:ethanedithiol (95:2.5:2.5); 3 hours for Wang® resin and 30 minutes for the Chloro (2-chorotrityl) resin. Following filtration, the solvents were removed by evaporation and the residue dissolved in acetonitrile (3 mL). Insoluble material was removed by filtration. The final products were purified by reverse phase chromatography with a linear gradient of buffer A (0.1% trifluoroacetic acid in water) and buffer B (0.1% trifluoroacetic acid in acetonitrile) and isolated by lyophilization. Molecular ions were obtained by electrospray ionization mass spectrometry or matrix-assisted laser desorption ionization time-of-flight mass spectrometry to confirm the structure of each peptide.

The following compounds were prepared by the general procedures described above using the appropriate amino acid derivatives and acyl or sulfonyl chloride or alkyl or aryl isocyanate. These examples are provided to illustrate the present invention and are not to be construed as limiting its scope in any manner.

| Ex. | Compound Name | MS* |
|---|---|---|
| (1) | N-(3,4-dimethoxybenzenesulfonyl)-1,2,3,4-tetrahydroisoquinoline-3(S)-carbonyl-(L)-leucine | 491 |
| (2) | N-(3,4-dimethoxybenzenesulfonyl)-1,2,3,4-tetrahydroisoquinoline-3(S)-carbonyl-(L)-arginine | 534 |
| (3) | N-(3,4-dimethoxybenzenesulfonyl)-1,2,3,4-tetrahydroisoquinoline-3(S)-carbonyl-(L)-glutamic acid | 507 |
| (4) | N-(3,4-dimethoxybenzenesulfonyl)-1,2,3,4-tetrahydroisoquinoline-3(S)-carbonyl-glycine | 435 |
| (5) | N-(3,4-dimethoxybenzenesulfonyl)-1,2,3,4-tetrahydroisoquinoline-3(S)-carbonyl-(L)-(1-naphthyl)alanine | 575 |
| (6) | N-(3,4-dimethoxybenzenesulfonyl)-1,2,3,4-tetrahydroisoquinoline-3(S)-carbonyl-(L)-α-t-butylglycine | 491 |
| (7) | N-(3,4-dimethoxybenzenesulfonyl)-1,2,3,4-tetrahydroisoquinoline-3(S)-carbonyl-(L)-3-(2-thienyl)alanine | 531 |

| Ex. | Compound Name | MS* |
|---|---|---|
| (8) | N-(3,4-dimethoxybenzenesulfonyl)-1,2,3,4-tetrahydroisoquinoline-3(S)-carbonyl-(L)-cyclohexylalanine | 531 |
| (9) | N-(3,4-dimethoxybenzenesulfonyl)-1,2,3,4-tetrahydroisoquinoline-3(S)-carbonyl-(L)-3-(2-naphthyl)alanine | 575 |
| (10) | N-(3,3-diphenylpropanoyl)-1,2,3,4-tetrahydro isoquinoline-3(S)-carbonyl-(L)-norleucine | 498 |
| (11) | N-(2,4-dinitrobenzenesulfonyl)-1,2,3,4-tetrahydroisoquinoline-3(S)-carbonyl-(L)-norleucine | 521 |
| (12) | N-(3,4-dimethoxybenzenesulfonyl)-1,2,3,4-tetrahydroisoquinoline-3(S)-carbonyl-(L)-3,3-diphenylalanine | 601 |
| (13) | N-(3,4-dimethoxybenzenesulfonyl)-1,2,3,4-tetrahydroisoquinoline-3(S)-carbonyl-1,2,3,4-tetrahydroisoquinoline-3-carboxylic acid | 537 |
| (14) | N-(3,4-dimethoxybenzenesulfonyl)-1,2,3,4-tetrahydroisoquinoline-3(S)-carbonyl-(L)-proline | 475 |
| (15) | N-dansyl-1,2,3,4-tetrahydroisoquinoline-3(S)-carbonyl-(L)-norleucine | 511 |
| (16) | N-(2-naphthalenesulfonyl)-1,2,3,4-tetrahydro isoquinoline-3(S)-carbonyl-(L)-norleucine | 481 |
| (17) | N-(4-methoxybenzenesulfonyl)-1,2,3,4-tetrahydro isoquinoline-3(S)-carbonyl-(L)-norleucine | 461 |
| (18) | N-(4-phenylbenzoyl)-1,2,3,4-tetrahydro isoquinoline-3(S)-carbonyl-(L)-norleucine | 471 |
| (19) | N-(3,4-dimethylbenzenesulfonyl)-1,2,3,4-tetrahydroisoquinoline-3(S)-carbonyl-(L)-cysteine | 481 |
| (20) | N-(4-t-butylbenzenesulfonyl)-1,2,3,4-tetrahydro isoquinoline-3(S)-carbonyl-(L)-norleucine | 487 |
| (21) | N-(2,5-dichlorobenzenesulfonyl)-1,2,3,4-tetrahydro isoquinoline-3(S)-carbonyl-(L)-norleucine | 498 |
| (22) | N-(2-mesitylenesulfonyl)-1,2,3,4-tetrahydro isoquinoline-3(S)-carbonyl-(L)-norleucine | 473 |
| (23) | N-(p-toluenesulfonyl)-1,2,3,4-tetrahydro isoquinoline-3(S)-carbonyl-(L)-norleucine | 444 |
| (24) | N-(4-chlorobenzenesulfonyl)-1,2,3,4-tetrahydro isoquinoline-3(S)-carbonyl-(L)-norleucine | 465 |
| (25) | N-(N'-acetylsulfanilyl)-1,2,3,4-tetrahydro isoquinoline-3(S)-carbonyl-(L)-norleucine | 488 |
| (26) | N-(4-fluorobenzenesulfonyl)-1,2,3,4-tetrahydro isoquinoline-3(S)-carbonyl-(L)-norleucine | 449 |
| (27) | N-(1-naphthalenesulfonyl)-1,2,3,4-tetrahydro isoquinoline-3(S)-carbonyl-(L)-norleucine | 481 |
| (28) | N-(benzylsulfonyl)-1,2,3,4-tetrahydroisoquinoline-3(S)-carbonyl-(L)-norleucine | 445 |
| (29) | N-(4-nitrobenzenesulfonyl)-1,2,3,4-tetrahydro isoquinoline-3(S)-carbonyl-(L)-norleucine | 476 |
| (30) | N-(3,4-dimethoxybenzenesulfonyl)-1,2,3,4-tetrahydroisoquinoline-3(S)-carbonyl-(L)-phenylalanine | 525 |
| (31) | N-(3,4-dimethoxybenzenesulfonyl)-1,2,3,4-tetrahydroisoquinoline-3(S)-carbonyl-(L)-glutamine | 506 |
| (32) | N-(3,4-dimethoxybenzenesulfonyl)-1,2,3,4-tetrahydroisoquinoline-3(S)-carbonyl-(L)-(4-nitrophenyl)alanine | 570 |
| (33) | N-(3,4-dimethoxybenzenesulfonyl)-1,2,3,4-tetrahydroisoquinoline-3(S)-carbonyl-(L)-asparagine | 492 |
| (34) | N-(3,4-dimethoxybenzenesulfonyl)-1,2,3,4-tetrahydroisoquinoline-3(S)-carbonyl-(L)-methionine | 509 |
| (35) | N-(3,4-dimethoxybenzenesulfonyl)-1,2,3,4-tetrahydroisoquinoline-3(S)-carbonyl-(L)-homophenylalanine | 539 |
| (36) | N-(3,4-dimethoxybenzenesulfonyl)-1,2,3,4-tetrahydroisoquinoline-3(S)-carbonyl-(D)-norleucine | 491 |
| (37) | N-(3,4-dimethoxybenzenesulfonyl)-1,2,3,4-tetrahydroisoquinoline-3(S)-carbonyl-(L)-(4-fluorophenyl)alanine | 543 |
| (38) | N-(3-toluenesulfonyl)-1,2,3,4-tetrahydro isoquinoline-3(S)-carbonyl-(L)-norleucine | 445 |
| (39) | N-(4-trifluoromethylbenzenesulfonyl)-1,2,3,4-tetrahydroisoquinoline-3(S)-carbonyl-(L)-norleucine | 499 |
| (40) | N-(4-n-propylbenzenesulfonyl)1,2,3,4-tetrahydro isoquinoline-3(S)-carbonyl-(L)-norleucine | 473 |
| (41) | N-(4-isopropylbenzenesulfonyl)-1,2,3,4-tetrahydroisoquinoline-3(S)-carbonyl-(L)-norleucine | 473 |
| (42) | N-(2,6-dichlorobenzenesulfonyl)-1,2,3,4-tetrahydro isoquinoline-3(S)-carbonyl-(L)-norleucine | 499 |
| (43) | N-(4-ethylbenzenesulfonyl)-1,2,3,4-tetrahydro isoquinoline-8(S)-carbonyl-(L)-norleucine | 459 |
| (44) | N-(2,4-difluorobenzenesulfonyl)-1,2,3,4-tetrahydro isoquinoline-3(S)-carbonyl-(L)-norleucine | 467 |
| (45) | N-(2-cyanobenzenesulfonyl)-1,2,3,4-tetrahydro isoquinoline-3(S)-carbonyl-(L)-norleucine | 456 |
| (46) | N-(4-tert-amylbenzenesulfonyl)-1,2,3,4-tetrahydro isoquinoline-3(S)-carbonyl-(L)-norleucine | 501 |
| (47) | N-(4-chloro-3-nitrobenzenesulfonyl)-1,2,3,4-tetrahydroisoquinoline-3(S)-carbonyl-(L)-norleucine | 510 |
| (48) | N-(3-cyanobenzoyl)-1,2,3,4-tetrahydro isoquinoline-3(S)-carbonyl-(L)-norleucine | 420 |
| (49) | N-(3,5-dichlorobenzenesulfonyl)-1,2,3,4-tetrahydroisoquinoline-3(S)-carbonyl-(L)-norleucine | 499 |
| (50) | N-(3,4-dichlorobenzenesulfonyl)-1,2,3,4-tetrahydroisoquinoline-3(S)-carbony(L)-norleucine | 499 |
| (51) | N-(2-trifluoromethylbenzenesulfonyl)-1,2,3,4-tetrahydroisoquinoline-3(S)-carbonyl-(L)-norleucine | 499 |
| (52) | N-(2,3-dichlorobenzenesulfonyl)-1,2,3,4-tetrahydro isoquinoline-3(S)-carbonyl-(L)-norleucine | 499 |
| (53) | N-(2,4-dichlorobenzenesulfonyl)-1,2,3,4-tetrahydro isoquinoline-3(S)-carbonyl-(L)-norleucine | 499 |
| (54) | N-(2,5-dimethoxybenzenesulfonyl)-1,2,3,4-tetrahydroisoquinoline-3(S)-carbonyl-(L)-norleucine | 491 |
| (55) | N-(3,4-dimethoxybenzenesulfonyl)-1,2,3,4-tetrahydroisoquinoline-3(S)-carbonyl-(L)-serine | 465 |
| (56) | N-(3,4-dimethoxybenzenesulfonyl)-1,2,3,4-tetrahydroisoquinoline-3(S)-carbonyl-(L)-isoleucine | 491 |
| (57) | N-(3,4-dimethoxybenzenesulfonyl)-1,2,3,4-tetrahydroisoquinoline-3(S)-carbonyl-(L)-tryptophan | 564 |
| (58) | N-(2,1,3-benzothiadiazole-4-sulfonyl)-1,2,3,4-tetrahydroisoquinoline-3(S)-carbonyl-(L)-tryptophan | 489 |
| (59) | N-(3,4-dimethoxybenzenesulfonyl)-1,2,3,4-tetrahydroisoquinoline-3(S)-carbonyl-(L)-3-(3-pyridyl)alanine | 526 |
| (60) | N-(3,4-dimethoxybenzenesulfonyl)-1,2,3,4-tetrahydroisoquinoline-3(S)-carbonyl-(L)-3-(2-naphthyl)alanine, ethyl ester | 603 |
| (61) | N-acetyl-1,2,3,4-tetrahydroisoquinoline-3(S)-carbonyl-(L)-norleucine | 333 |
| (62) | N-(3,4-dimethoxybenzenesulfonyl)-1,2,3,4-tetrahydroisoquinoline-3(R)-carbonyl-(D)-norleucine | 491 |
| (63) | N-propionyl-(L)-prolyl-1,2,3,4-tetrahydro isoquinoline-3(S)-carbonyl-(L)-norleucine | 348 |
| (64) | N-(4-cyanobenzenesulfonyl)-1,2,3,4-tetrahydro isoquinoline-3(S)-carbonyl-(L)-norleucine | 456 |
| (65) | N-(benzenesulfonyl)-1,2,3,4-tetrahydro isoquinoline-3(S)-carbonyl-(L)-norleucine | 431 |
| (66) | N-(3-nitrobenzenesulfonyl)-1,2,3,4-tetrahydro isoquinoline-3(S)-carbonyl-(L)-norleucine | 476 |
| (67) | N-(3-trifluoromethylbenzenesulfonyl)-1,2,3,4-tetrahydroisoquinoline-3(S)-carbonyl-(L)-norleucine | 499 |

-continued

| Ex. | Compound Name | MS* |
|---|---|---|
| (68) | N-(2-thienylsulfonyl)-1,2,3,4-tetrahydro isoquinoline-3(S)-carbonyl-(L)-norleucine | 437 |
| (69) | N-(3,4-dimethoxybenzenesulfonyl)-1,2,3,4-tetrahydroisoquinoline-3(S)-carbonyl-(L)-N-methylleucine | 505 |
| (70) | N-(3,4-dimethoxybenzenesulfonyl)-1,2,3,4-tetrahydroisoquinoline-3(S)-carbonyl-(L)-citrulline | 535 |
| (71) | N-(4-iodobenzenesulfonyl)-1,2,3,4-tetrahydro isoquinoline-3(S)-carbonyl-(L)-norleucine | 557 |
| (72) | N-(3,5-dichlorobenzenesulfonyl)-(L)-prolyl-(L)-(3-iodo)tyrosine | 613 |
| (73) | N-(3,5-dichlorobenzenesulfonyl)-(L)-prolyl-(L)-(3-pyridyl)alanine | 472 |
| (74) | N-(3,5-dichlorobenzenesulfonyl)-(L)-prolyl-(L)-phenylalanine | 471 |
| (75) | N-(3,5-dichlorobenzenesulfonyl)-(L)-prolyl-(L)-glutamic acid | 453 |
| (76) | N-(3,5-dichlorobenzenesulfonyl)-(L)-prolyl-(L)-arginine | 480 |
| (77) | N-(N-(3,5-dichlorobenzenesulfonyl)-(L)-prolyl-1-amino-cyclopentane-1-carboxylic acid | 549 |
| (78) | N-(3,5-dichlorobenzenesulfonyl)-(L)-prolyl-(L)-3-(3,4-dichlorophenyl)alanine | 541 |
| (79) | N-(3,5-dichlorobenzenesulfonyl)-(L)-prolyl-(L)-3-(2-naphthyl)alanine, ethyl ester | 549 |
| (80) | N-(3,5-dichlorobenzenesulfonyl)-(L)-prolyl-(L)-3-(4-bromophenyl)alanine | 550 |
| (81) | N-(3,5-dichlorobenzenesulfonyl)-(L)-prolyl-(L)-3-(4-nitrophenyl)alanine | 516 |
| (82) | N-(3,5-dichlorobenzenesulfonyl)-(L)-prolyl-(L)-3-(4-thiazolyl)alanine | 478 |
| (83) | N-(3,5-dichlorobenzenesulfonyl)-(L)-prolyl-(L)-3-(2-chlorophenyl)alanine | 507 |
| (84) | N-(3,5-dichlorobenzenesulfonyl)-(L)-prolyl-(L)-3-(4-chlorophenyl)alanine | 507 |
| (85) | N-(3,5-dichlorobenzenesulfonyl)-(L)-prolyl-(L)-3-(4-cyanophenyl)alanine | 496 |
| (86) | N-(3,5-dichlorobenzenesulfonyl)-(L)-prolyl-(L)-tyrosine, O-sulfate | 586 |
| (87) | N-(3,5-dichlorobenzenesulfonyl)-(L)-prolyl-(L)-3,5-diiodotyrosine | 739 |
| (88) | N-(3,5-dichlorobenzenesulfonyl)-(L)-prolyl-(L)-tyrosine | 488 |
| (89) | N-(3,5-dichlorobenzenesulfonyl)-(L)-prolyl-(L)-aspartic acid | 438 |
| (90) | N-(3,5-dichlorobenzenesulfonyl)-(L)-prolyl-(L)-tryptophan | 510 |
| (91) | N-(3,5-dichlorobenzenesulfonyl)-(L)-prolyl-(L)-methionine | 454 |
| (92) | N-(3,4-dimethoxybenzenesulfonyl)-(L)-prolyl-(L)-norleucine | 429 |
| (93) | N-(3,5-di(trifluoromethyl)benzenesulfonyl)-(L)-prolyl-(L)-3-(2-naphthyl)alanine | 589 |
| (94) | N-(3,4-dimethoxybenzenesulfonyl)-(L)-thiaprolyl-(L)-3-(2-naphthyl)alanine | 531 |
| (95) | N-(3,4-dimethoxybenzenesulfonyl)-(L)-thiaprolyl-(L)-norleucine | 447 |
| (96) | N-[4-(N'-2-toluylureido)phenylacetyl]-(L)-thiaprolyl-(L)-3-(2-naphthyl)alanine | 597 |
| (97) | N-(3,5-dichlorobenzenesulfonyl)-(L)-thiaprolyl-(L)-3-(2-naphthyl)alanine | 539 |
| (98) | N-(3,4-dimethoxybenzenesulfonyl)-(L)-pipecolyl-(L)-norleucine | 443 |
| (99) | N-(3,4-dimethoxybenzenesulfonyl)-(L)-pipecolyl-(L)-norleucine, ethyl ester | 471 |
| (100) | N-(3,5-dichlorobenzenesulfonyl)-(L)-pipecolyl-(L)-homophenylalanine | 499 |
| (101) | N-(3,5-dichlorobenzenesulfonyl)-(L)-pipecolyl-(L)-(3-iodo)tyrosine | 626 |
| (102) | N-(3,5-dichlorobenzenesulfonyl)-(L)-pipecolyl-(L)-3-(2-naphthyl)alanine | 535 |
| (103) | N-[4-(N'-2-toluylureido)phenylacetyl]-(L)-pipecoliny(L)-3-(2-naphthyl)alanine | 593 |
| (104) | N-[3,5-di(trifluoromethyl)benzenesulfonyl]-(L)-pipecolyl-(L)-3-(2-naphthyl)alanine | 603 |
| (105) | N-(3,4-dimethoxybenzenesulfonyl)-(L)-pipecolyl-(L)-3-(2-naphthyl)alanine, ethyl ester | 555 |
| (106) | N-(3,4-dimethoxybenzenesulfonyl)-(L)-octahydroisoquinoline-3-carbonyl-(L)-norleucine | 483 |
| (107) | N-(3,4-dimethoxybenzenesulfonyl)-azetidine-2-carbonyl-(L)-norleucine | 415 |
| (108) | N-(3,5-dichlorobenzenesulfonyl)-(L)-4(S)-hydroxyprolyl-(L)-3-(2-naphthyl)alanine | 537 |
| (109) | N-(3,4-dimethoxybenzenesulfonyl)-(L)-4(S)-hydroxyprolyl-(L)-norleucine | 445 |
| (110) | N-(3,4-dimethoxybenzenesulfonyl)-(L)-3,4-dehydroprolyl-(L)-norleucine | 427 |
| (111) | N-(3-bis(N,N-benzenesulfonyl)aminobenzenesulfonyl)-(L)-prolyl-(L)-norleucine | |
| (112) | N-(3,5-dichlorobenzenesulfonyl)-(L)-prolyl-3-(4-pyridyl)alanine | 472.2 |
| (113) | N-(3,5-dichlorobenzenesulfonyl)-(L)-4(R)-aminoprolyl-(L)-3-(2-naphthyl)alanine | 536.1 |
| (114) | N-(3,5-dichlorobenzenesulfonyl)-(L)-3,4-dehydroprolyl-(L)-4-fluorophenylalanine | 487.2 |
| (115) | N-(3-chlorobenzenesulfonyl)-(L)-prolyl-(L)-4-fluorophenylalanine | 455.1 |
| (116) | N-(3,5-dichlorobenzenesulfonyl)-(L)-4(R)-hydroxyprolyl-(L)-4-fluorophenylalanine | 505.2 |
| (117) | N-(3,5-dichlorobenzenesulfonyl)-(L)-thiaprolyl-(L)-tyrosine | 505.0 |
| (118) | N-(3,5-dichlorobenzenesulfonyl)-(L)-thiaprolyl-(L)-3-iodotyrosine | 631.0 |
| (119) | N-(3-fluorobenzenesulfonyl)-(L)-thiaprolyl-(L)-3-(2-naphthyl)alanine | 489.3 |
| (120) | N-(3-fluorobenzenesulfonyl)-(L)-pipecolyl-(L)-3-(2-naphthyl)alanine | 485.4 |
| (121) | N-(3-fluorobenzenesulfonyl)-(L)-thiaprolyl-(L)-4-fluorophenylalanine | 457.2 |
| (122) | N-(3-fluorobenzenesulfonyl)-(L)-prolyl-(L)-4-fluorophenylalanine | 439.2 |
| (123) | N-(3-chlorobenzenesulfonyl)-(L)-3,4-dehydroprolyl-(L)-4-fluorophenylalanine | 453.3 |
| (124) | N-(3-fluorobenzenesulfonyl)-(L)-4(R)-hydroxyprolyl-(L)-4-fluorophenylalanine | 455.0 |
| (125) | N-(3-chlorobenzenesulfonyl)-(L)-4(R)-hydroxyprolyl-(L)-4-fluorophenylalanine | 471.0 |
| (126) | N-(3,5-dichlorobenzenesulfonyl)-(L)-pipecolyl-(L)-4-fluorophenylalanine | 503.1 |
| (127) | N-(3-fluorobenzenesulfonyl)-(L)-3,4-dehydroprolyl-(L)-tyrosine | 435.3 |
| (128) | N-(4,5-dichloro-2-thiophenesulfonyl)-(L)-prolyl-(L)-tyrosine | 493.2 |
| (129) | N-(3-fluorobenzenesulfonyl)-(L)-4(R)-hydroxyprolyl-(L)-tyrosine | 453.2 |
| (130) | N-(3-chlorobenzenesulfonyl)-(L)-4(R)-hydroxyprolyl-(L)-tyrosine | 469.2 |
| (131) | N-(3-fluorobenzenesulfonyl)-(L)-pipecolyl-(L)-4-fluorophenylalanine | 453.3 |
| (132) | N-(3-fluorobenzenesulfonyl)-(L)-4(R)-hydroxyprolyl-(L)-tyrosine, O-tert-butyl ether | 509.1 |
| (133) | N-3-chlorobenzenesulfonyl)-(L)-4(R)-hydroxyprolyl-(L)-tyrosine, O-tert-butyl ether | 525.3 |
| (134) | N-(4,5-dichloro-2-thiophenesulfonyl)-(L)-3,4-dehydroprolyl-(L)-tyrosine | 491.1 |
| (135) | N-(3,5-dichlorobenzenesulfonyl)-(L)-3(S)-methyl-prolyl-(L)-4-fluorophenylalanine | 503.1 |
| (136) | N-(4,5-dichloro-2-thiophenesulfonyl)-(L)-3,4-dehydroprolyl-(L)-tyrosine | 485.1 |
| (137) | N-(3-fluorobenzenesulfonyl)-(L)-3,4-dehydroprolyl-(L)-tyrosine, O-tert-butyl ether | 491.1 |
| (138) | N-(3-chlorobenzenesulfonyl)-(L)-3,4-dehydroprolyl-(L)-tyrosine, O-tert-butyl ether | 507.3 |
| (139) | N-(3-chlorobenzenesulfonyl)-(L)-2(S)-methyl-prolyl-(L)-4-fluorophenylalanine | 469.1 |
| (140) | N-(3-chlorobenzeneslfonyl-(L)-2(S)-methyl-prolyl-(L)-tyrosine | 467.3 |
| (141) | N-(3-fluorobenzenesulfonyl)-(L)-2(S)-methyl-prolyl-(L)-tyrosine, O-tert-butyl ether | 523.2 |
| (142) | N-(3,5-dichlorobenzenesulfonyl-(L)-2(S)-methyl-prolyl-(L)-tyrosine | 501.0 |
| (143) | N-(3-fluorobenzenesulfonyl)-(L)-prolyl-(L)-3- | 563.1 |

-continued

| Ex. | Compound Name | MS* |
|---|---|---|
| (144) | N-(3-chlorobenzenesulfonyl)-(L)-prolyl-(L)-3-iodotyrosine | 579.0 |
| (145) | N-(3-fluorobenzenesulfonyl)-(L)-prolyl-(L)-3-phenylalanine | 421.1 |
| (146) | N-(3-chlorobenzenesulfonyl)-(L)-prolyl-(L)-phenylalanine | 437.3 |
| (147) | N-(3,5-dichlorobenzenesulfonyl)-(L)-prolyl-(L)-phenylalanine | 471.2 |
| (148) | N-(3-fluorobenzenesulfonyl)-(L)-4(R)-hydroxyprolyl-(L)-phenylalanine | 437.3 |
| (149) | N-(3-chlorobenzenesulfonyl)-(L)-4(R)-hydroxyprolyl-(L)-phenylalanine | 453.2 |
| (150) | N-(4,5-dichloro-2-thiophenesulfonyl)-(L)-3,4-dehydroprolyl-(L)-3-(4-pyridyl)alanine | 476.1 |
| (151) | N-(4,5-dichloro-2-thiophenesulfonyl)-(L)-thiaprolyl-(L)-3-(4-pyridyl)alanine | 495.9 |
| (152) | N-(4,5-dichloro-2-thiophenesulfonyl)-(L)-3,4-dehydroprolyl-(L)-4-fluorophenylalanine | 492.9 |
| (153) | N-(3,5-dichlorobenzenesulfonyl)-(L)-4(R)-hydroxyprolyl-(L)-phenylalanine | 487.1 |
| (154) | N-(3-trifluoromethylbenzenesulfonyl)-(L)-prolyl-(L)-4-fluorophenylalanine | 489.3 |
| (155) | N-(3-trifluoromethylbenzenesulfonyl)-(L)-thiaprolyl-(L)-4-fluorophenylalanine | 507.0 |
| (156) | N-(3-fluorobenzenesulfonyl)-(L)-3,4-dehydroprolyl-(L)-4-fluorophenylalanine | 437.1 |
| (157) | N-(3,5-dichlorobenzenesulfonyl)-(L)-prolyl-(L)-tyrosine, O-phosphoric acid | 567.0 |
| (158) | N-(3-chlorobenzenesulfonyl)-(L)-4(R)-aminoprolyl-(L)-tyrosine | 468.3 |
| (159) | N-(4,5-dichloro-2-thiophenesulfonyl)-(L)-thiaprolyl-(L)-tyrosine | 510.9 |
| (160) | N-(N₁-methyl-4-imidazolesulfonyl)-(L)-prolyl-(L)-4-fluorophenylalanine | 425.3 |
| (161) | N-(3,5-dichlorobenzenesulfonyl)-(D)-proyl-(D)-4-fluorophenylalanine | 489.1 |
| (162) | N-(4,5-dichloro-2-thiophenesulfonyl)-(L)-4(R)-aminoprolyl-(L)-3-(4-pyridyl)alanine | 492.9 |
| (163) | N-(5-(5-trifluoromethyl-2-pyridylsulfonyl)-2-thiophenesulfonyl)-(L)-proyll-(L)-4-fluorophenylalanine | 636.1 |
| (164) | N-(5-(N-(4-chlorobenzoyl)aminomethyl))-2-thiophenesulfonyl)-(L)-prolyl-(L)-4-fluorophenylalanine | 575.1 |
| (165) | N-(5-(3-(1-methyl-5-trifluoromethyl-pyrazoyl))-2-thiophenesulfonyl)-(L)-prolyl-(L)-4-fluorophenylalanine | 594.0 |
| (166) | N-(3-fluorobenzenesulfonyl)-2(S)-methylprolyl-(L)-O-tert-butyl-tyrosine | 507.3 |
| (167) | N-(3-fluorobenzenesulfonyl)-(L)-4(R)-aminoprolyl-(L)-4-fluorophenylalanine | 454.2 |
| (168) | N-(3,5-dichlorobenzenesulfonyl)-(L)-4(R)-aminoprolyl-(L)-4-fluorophenylalanine | 504.3 |
| (169) | N-(3-chlorobenzenesulfonyl)-(L)-4(R)-aminoprolyl-(L)-4-fluorophenylalanine | 470.1 |
| (170) | N-(3,5-dichlorobenzenesulfonyl)-(L)-4(S)-aminoprolyl-(L)-4-fluorophenylalanine | 504.0 |
| (171) | N-(3-chlorobenzenesulfonyl)-(L)-thiaprolyl-(L)-4-fluorophenylalanine | 473.3 |
| (172) | N-(4-bromo-5-chloro-2-thiophenesulfonyl)-(L)-prolyl-(L)-4-fluorophenylalanine | 540.9 |
| (173) | N-(4,5-dichloro-2-thiophenesulfonyl)-(L)-prolyl-(L)-4-fluorophenylalanine | 513.0 |
| (174) | N-(3,5-dichlorobenzenesulfonyl)-(L)-thiaprolyl-(L)-3,5-diiodotyrosine | 756.7 |
| (175) | N-(5-benzoylaminomethyl-2-thiophenesulfonyl)-(L)-prolyl-(L)-4-fluorophenylalanine | 560.1 |
| (176) | N-(3,5-dichlorobenzenesulfonyl)-(L)-prolyl-(L)-O-tert-butyl-tyrosine | 509.3 |
| (177) | N-(5-benzenesulfonyl-2-thiophenesulfonyl)-(L)-prolyl-(L)-4-fluorophenylalanine | 567.0 |
| (178) | N-(3-bromo-5-chloro-2-thiophenesulfonyl)-(L)-prolyl-(L)-4-fluorophenylalanine | 540.9 |
| (179) | N-(3-chlorobenzenesulfonyl)-(L)-3,4-dehydroprolyl-(L)-tyrosine | 451.2 |
| (180) | N-(3,5-dichlorobenzenesulfonyl)-(L)-prolyl-(L)-homophenylalanine | 485.3 |

-continued

| | Ex. | Compound Name | MS* |
|---|---|---|---|
| 814561 | (181) | N-(4-benzenesulfonyl-2-thiophenesulfonyl)-(L)-prolyl-(L)-O-tert-butyl-tyrosine | 621.1 |
| 814562 | (182) | N-(5-benzoylaminomethyl-2-thiophenesulfonyl)-(L)-prolyl-(L)-O-tert-butyl-tyrosine | 614.2 |
| 814564 | (183) | N-(trans-2-phenyl-ethylene-sulfonyl)-(L)-prolyl-(L)-O-tert-butyl-tyrosine | 501.3 |
| 814568 | (184) | N-(5-benzenesulfonyl-2-thiophenesulfonyl)-(L)-prolyl-(L)-O-tert-butyl-tyrosine | 621.1 |
| 814569 | (185) | N-(3-fluorobenzenesulfonyl)-(L)-thiaprolyl-(L)-O-tert-butyl-tyrosine | 511.2 |
| 814570 | (186) | N-(benzylsulfonyl)-(L)-prolyl-(L)-O-tert-butyl-tyrosine | 489.3 |
| 814572 | (187) | N-(3,5-dichlorobenzenesulfonyl)-(L)-prolyl-(L)-cysteine, amide | 426.2 |
| 814576 | (188) | N-(1-methyl-4-imidazolylsulfonyl)-(L)-prolyl-(L)-O-tert-butyl-tyrosine | 479.1 |
| 814578 | (189) | N-(4-(N-(4-dimethylaminophenyl)diazo)-benzenesulfonyl)-(L)-prolyl-(L)-O-tert-butyl-tyrosine | 622.0 |
| 814579 | (190) | N-(5-(4-trifluoromethylbenzenesulfonyl)-2-thiophenesulfonyl)-(L)-prolyl-(L)-O-tert-butyl-tyrosine | 690.2 |
| 814580 | (191) | N-(3-bromobenzenesulfonyl)-(L)-prolyl-(L)-O-tert-butyl-tyrosine | 553.2 |
| 814581 | (192) | N-(4-methylsulfonyl-benzenesulfonyl)-(L)-prolyl-(L)-4-fluorophenylalanine | 499.2 |
| 814586 | (193) | N-(4-methoxybenzenesulfonyl)-(L)-prolyl-(L)-O-tert-butyl-tyrosine | 505.2 |
| 814589 | (194) | N-(4,5-dichloro-2-thiophenesulfonyl)-(L)-prolyl-(L)-3-fluorophenylalanine | 495.0 |
| 814591 | (195) | N-(5-chloro-2-thiophenesulfonyl)-(L)-prolyl-(L)-4-fluorophenylalanine | 461.1 |
| | (196) | N-(3-chlorobenzenesulfonyl)-(L)-thiaprolyl-(L)-tyrosine | 471.0 |
| | (197) | N-(3,5-dichlorobenzenesulfonyl)-(L)-2(S)-methylprolyl-(L)-O-tert-butyl-tyrosine | 558.6 |
| | (198) | N-(1(R)-(+)-10-camphorsulfonyl)-(L)-prolyl-(L)-O-tert-butyl-tyrosine | 549.3 |
| | (199) | N-(1(S)-(+)-10-camphorsulfonyl)-(L)-prolyl-(L)-O-tert-butyl-tyrosine | 549.3 |
| | (200) | N-(3,4-methylenedioxy-phenylacetyl)-(L)-prolyl-(L)-O-tert-butyl-tyrosine | 497.2 |
| | (201) | N-(3-chlorobenzenesulfonyl)-(L)-4(R)-hydroxyprolyl-(L)-tyrosine-O-sulfate | 551.0 |
| | (202) | N-(3-chlorobenzenesulfonyl)-(L)-thiaprolyl-(L)-tyrosine-O-sulfate | 553.7 |
| | (203) | N-(3,5-dichlorobenzenesulfonyl)-(L)-prolyl-(L)-cysteine | 427.2 |
| | (204) | N-(3,5-dichlorobenzenesulfonyl)-(L)-prolyl-(L)-N-methyl-isoleucine | 451.2 |
| | (205) | N-(3,5-dichlorobenzenesulfonyl)-(L)-4(R)-aminoprolyl-(L)-O-tert-butyl-tyrosine | 558.3 |
| | (206) | N-(3-chlorobenzenesulfonyl)-(L)-4(R)-aminoprolyl-(L)-O-tert-butyl-tyrosine | 524.4 |
| | (207) | N-(3-cyanobenzenesulfonyl)-(L)-prolyl-(L)-tyrosine | 444.3 |
| | (208) | N-benzenesuulfonyl-(L)-prolyl-(L)-O-tert-butyl-tyrosine | 475.5 |
| | (209) | N-(4-methylsulfonylbenzenesulfonyl)-(L)-prolyl-(L)-O-tert-butyl-tyrosine | 553.2 |
| | (210) | N-(4,5-dichloro-2-thiophenesulfonyl)-(L)-4(R)-aminoprolyl-(L)-O-tert-butyl-tyrosine | 564.3 |
| | (211) | N-(4,5-dichloro-2-thiophenesulfonyl)-(L)-4(R)-aminoprolyl-(L)-4-fluorophenylalanine | 510.1 |
| | (212) | N-(9-fluorenylmethyloxycarbonyl)-(L)-prolyl-(L)-phenylalanine | 485 |
| | (218) | N-(benzenesulfonyl)-(L)-prolyl-(L)-phenylalanine | 403 |
| | (214) | N-(n-octyl-1-sulfonyl)-(L)-prolyl-(L)-phenylalanine | 418 |
| | (215) | N-(3-fluorobenzenesulfonyl)-(L)-5(R)-phenyl-prolyl-(L)-4-fluorophenylalanine | 515 |
| | (216) | N-(3,5-dichlorobenzenesulfonyl)-(L)-3(R)-phenyl-prolyl-(L)-4-iodophenylalanine | 582 |
| | (217) | N-(3,5-dichlorobenzenesulfonyl)-1,2,3,4-tetrahydro isoquinoline-1-carbonyl-(L)-4-fluorophenylalanine | 568 |

-continued

| Ex. | Compound Name | MS* |
|---|---|---|
| (218) | N-(3,5-dichlorobenzenesulfonyl)-1,3-dihydro isoindolyl-1-carbonyl-(L)-4-fluorophenylalanine | 554 |
| (219) | N-(4-(fluorescien-4-carbonylamino)benzene sulfonyl)-(L)-prolyl-(L)-O-tert-butyl-tyrosine | 879.2 |
| (220) | N-(3-ethoxycarbonyl-benzenesulfonyl)-(L)-prolyl-(L)-O-tert-butyl-tyrosine | 547.2 |
| (221) | N-(4-iodobenzenesulfonyl)-(L)-prolyl-(L)-4-benzoyl-phenylalanine | 633.0 |
| (222) | N-(3-(4-benzophenonyl-carbonylamino)-benzenesulfonyl)-(L)-prolyl-(L)-O-tert-butyl-tyrosine | 698.2 |
| (223) | N-(3-(6-(biotinylamino)-n-hexanoyl)-aminobenzenesulfonyl)-(L)-prolyl-(L)-O-tert-butyl-tyrosine | 829.4 |
| (224) | N-(3,5-dichlorobenzenesulfonyl)-[3.1.0]-3-azabicyclohexane-2-carbonyl-(L)-4-fluorophenylalanine | 518 |

*m/e: (M + 1 (H⁺))⁺ or (M + 18 (NH₄⁺))⁺

EXAMPLE 225

N-(3,5-Dichlorobenzenesulfonyl))-(L)-prolyl-(L)-3-(2-naphthyl)alanine

Step A: (L)-3-(2-Naphthyl)alanine, tert-butyl ester, hydrochloride

To a solution of N-Boc-2-naphthylalanine (1.0 g, 3.17 mmol) in a mixture of methylene chloride (7 mL) and cyclohexane (14 mL) were added t-butyl trichloroacetimidate (0.60 mL, 3.35 mmol) and boron trifluoride-etherate (60 µL, 0.473 mmol). The reaction mixture was stirred for 5 hours at room temperature under a nitrogen atmosphere and then treated a second time with the same amounts of t-butyl trichloroacetimidate and boron trifluoride-etherate as above. After stirring overnight, the mixture was filtered and the filtrate evaporated. The product was obtained pure by silica gel chromatography eluting with 10% diethyl ether in hexane; yield 843 mg. The product was treated with 1M HCl in ethyl acetate (11.5 mL) for 18 hours at room temperature. The mixture was evaporated and coevaporated several times with diethyl ether to afford the title compound; yield 670 mg.

400 MHz $^1$H NMR (CD$_3$OD): δ 1.38 (s, 9H); 3.29–3.46 (m, 2H); 4.28 (t, 1H); 7.40–7.90 (m, 7H).

Step B: N-(Benzyloxycarbonyl)-(L)-prolyl-(L)-3-(2-naphthyl)alanine, tert-butyl ester.

To a solution of N-(benzyloxycarbonyl)-(L)-proline (536 mg, 2.15 mmol) in methylene chloride (25 mL) were added 1-hydroxybenzotriazole (434 mg, 3.21 mmol), N-methylmorpholine (0.353 mL, 3.21 mmol), and (L)-2-naphthylalanine tert-butyl ester hydrochloride (660 mg, 2.14 mmol). After cooling in an ice-bath for 5 minutes, 1-(3-dimethylaminopropyl)-3-ethylcarbodiimide hydrochloride (EDC) (493 mg, 2.57 mmol) was added. After 15 minutes, the cooling bath was removed and the mixture stirred overnight under a nitrogen atmosphere. The mixture was diluted with methylene chloride, washed with water, 2n HCl, saturated NaHCO$_3$ solution, saturated brine solution, dried (anhydrous magnesium sulfate), and evaporated. Silica gel chromatography eluting with 30% ethyl acetate in hexane afforded pure title compound; yield 877 mg (81%).

Step C: (L)-Prolyl-(L)-3-(2-naphthyl)alanine, tert-butyl ester.

A solution of N-(benzyloxycarbonyl)-(L)-prolyl-(L)-2-naphthylalanine tert-butyl ester (870 mg, 1.73 mmol) in methanol (30 mL) was hydrogenated under an atmosphere of hydrogen gas in the presence of 10% palladium-on-charcoal (75 mg) until complete disappearance of starting material (several hours) as indicated by TLC (30% ethyl acetate in hexane). The catalyst was removed by filtration through Celite, the filter washed with methanol, and the combined filtrate and washings evaporated to afford an oil that crystallized upon standing; yield 604 mg (95%).

400 MHz $^1$H NMR (CD$_3$OD): δ 1.40 (s, 9H); 2.00 (m, 1H); 2.79 (m, 2H); 3.16 (dd, 1H); 3.58 (dd, 1H); 4.67 (dd, 1H); 7.32–7.81 (m, 7H).

Step D: N-(3.5-Dichlorobenzenesulfonyl))-(L)-prolyl-(L)-3-(2-naphthyl)alanine, tert-butyl ester.

To a solution of (O)-prolyl-(L)-2-naphthylalanine tert-butyl ester (400 mg, 1.09 mmol) in methylene chloride (10 mL) were added N,N-diisopropylethylamine (470 µL, 2.70 mmol), 4-dimethylaminopyridine (13 mg, 0.106 mmol), and 3,5-dichlorobenzenesulfonyl) chloride (320 mg, 1.30 mmol). The reaction mixture was stirred for 2 hours at room temperature, diluted with methylene chloride, washed with water, 2N HCl, saturated NaHCO$_3$ solution, saturated brine solution, dried (Anhydrous magnesium sulfate), and evaporated. Pure title compound was obtained by silica gel chromatography eluting with 20% ethyl acetate in hexane; yield 501 mg (80%).

400 MHz $^1$H NMR (CD$_3$OD): δ 1.40 (9, 9H); 1.53–1.89 (m, 4H); 3.20–3.45 (m, 4H); 4.20 (dd, 1H); 4.69 (dd, 1H); 7.40–7.80 (m, 10H).

Step E: N-(3.5-Dichlorobenzenesulfonyl))-(L)-prolyl-(L)-3-(2-naphthyl)alanine.

(224) A cooled solution of N-(3,5-dichlorobenzenesulfonyl))-(L)-prolyl-(L)-2-naphthylalanine tert-butyl ester (497 mg, 0.861 mmol) in methylene chloride (25 mL) was treated with trifluoroacetic acid (3.5 mL, 0.045 mol). The cooling bath was removed, and the mixture was stirred until TLC (25% ethyl acetate in hexane) indicated complete disappearance of starting material. The reaction mixture was then evaporated, coevaporated with methylene chloride (3×), toluene (2×), and finally methanol. The product was dried under high vacuum; yield 445 mg (99%).

MS: m/e 521 (M); 537 (M+NH$_3$)

400 MHz $^1$H NMR (CD$_3$OD): δ 1.51–1.87 (m, 4H); 3.19–3.46 (m, 4H); 4.20 (dd, 1H); 4.80 (dd, 1H); 7.39–7.82 (m, 10H).

The following compounds were prepared by the procedures described in Example 225 using the appropriate amino acid derivatives and acyl or sulfonyl chloride or alkyl or aryl isocyanate:

| Ex. | Compound Name | MS* |
|---|---|---|
| (226) | N-[4-(N'-2-toluylureido)phenylacetyl-(L)-prolyl-(L)-norleucine | 495 |
| (227) | N-(3,4-dimethoxybenzoyl)-(L)-prolyl-(L)-norleucine | 393 |
| (228) | N-(3,4-dimethoxybenzenesulfonyl))-(L)-pipecolyl-(L)-tryptophan | 516 |
| (229) | N-(4-nitrobenzenesulfonyl))-(L)-prolyl-(L)-norleucine | 414 |
| (230) | N-[3,5-di(trifluoromethyl)benzenesulfonyl)]-(L)-prolyl-(L)-norleucine | 505 |
| (231) | N-(3,5-dichlorobenzenesulfonyl))-(L)-prolyl-(L)-norleucine | 437 |
| (232) | N-(3-trifluoromethylbenzenesulfonyl))-(L)-prolyl-(L)-norleucine | 437 |
| (233) | N-[4-(benzoylamino)benzenesulfonyl))-(L)-prolyl-(L)-norleucine | 488 |
| (234) | N-(4-methoxy-3,5-dinitrobenzenesulfonyl)-(L)-prolyl-(L)-norleucine | 488 |

| Ex. | Compound Name | MS* |
|---|---|---|
| (235) | N-(3-chlorobenzesulfonyl))-(L)-prolyl-(L)-norleucine | 402 |
| (236) | N-(3-trifluoromethylbenzenesulfonyl))-(L)-prolyl-(L)-3-(2-naphthyl)alanine | 521 |
| (237) | N-(3-nitrobenzenesulfonyl))-(L)-prolyl-(L)-norleucine | 414 |
| (238) | N-(3-cyanobenzenesulfonyl))-(L)-prolyl-(L)-norleucine | 394 |
| (239) | N-(3,5-dichlorobenzenesulfonyl))-(L)-prolyl-(L)-tryptophan | 510 |
| (240) | N-(3-methylbenzenesulfonyl))-(L)-prolyl-(L)-norleucine | 383 |
| (241) | N-(3,5-dichlorobenzenesulfonyl))-(L)-3(S)-methyl-prolyl-(L)-3-(2-naphthyl)alanine | 535 |
| (242) | N-(3-chlorobenzenesulfonyl)-(L)-prolyl-(L)-3-(2-naphthyl)alanine | 488 |
| (243) | N-(3-fluorobenzenesulfonyl))-(L)-prolyl-(L)-3-(2-naphthyl)alanine | 471 |
| (244) | N-phenylacetyl-(L)-prolyl-(L)-3-(2-naphthyl)alanine | 431 |
| (245) | N-(3-phenylpropionyl)-(L)-prolyl-(L)-3-(2-naphthyl)alanine | 445 |
| (246) | N-(phenylaminocarbonyl)-(L)-prolyl-(L)-3-(2-naphthyl)alanine | 432 |
| (247) | N-(3,5-dichlorobenzenesulfonyl))-(L)-2-methyl-prolyl-(L)-3-(2-naphthyl)-alanine | 535 |
| (248) | N-(benzenesulfonyl)-(L)-prolyl-(L)-3-(2-naphthyl)alanine | 453 |
| (249) | N-(4-N'-phenylureidobenzenesulfonyl)-(L)-prolyl-(L)-3-(2-naphthyl)alanine | 587 |
| (250) | N-(3-fluorobenzenesulfonyl)-(L)-5,5-dimethyl-prolyl-(L)-3-(2-naphthyl)alanine | 499 |
| (251) | N-(4-N'-(2-toluyl)ureidobenzenesulfonyl)-(L)-prolyl-(L)-3-(2-naphthyl)alanine | 601 |
| (252) | N-(3-fluorobenzenesulfonyl)-(L)-prolyl-(L)-4-iodophenylalanine | 547 |
| (253) | N-(4-N'-benzylureidobenzenesulfonyl)-(L)-prolyl-(L)-3-(2-naphthyl)alanine | 601 |
| (254) | N-(phenyloxalyl)-(L)-prolyl-(L)-3-(2-naphthyl)alanine | 445 |
| (255) | N-(benzylaminocarbonyl)-(L)-prolyl-(L)-3-(2-naphthyl)alanine | 445 |
| (256) | N-(3-fluorobenzenesulfonyl)-(L)-2(S)-methyl-prolyl-(L)-4-fluorophenyalanine | 470 |
| (257) | N-(3,5-dichlorobenzenesulfonyl)-(L)-2(S)-methyl-prolyl-(L)-4-fluorophenylalanine | 520 |
| (258) | N-(3,5-dichlorobenzenesulfonyl)-(L)-prolyl-(L)-phenylalaninamide-N-methylsulfonamide | 565 |
| (259) | N-(3,5-dichlorobenzenesulfonyl)-(L)-2(S)-methyl-prolyl-(L)-4-iodophenylalanine | 628 |
| (260) | N-(3-fluorobenzenesulfonyl)-(L)-prolyl-(L)-phenylalanine | 261** |
| (261) | N-(3,5-dichlorobenzenesulfonyl)-(L)-5-methylprolyl-(L)-4-fluorophenylalanine | 520 |
| (262) | N-(3,5-dichlorobenzenesulfonyl)-3-phenylazetidinylcarbonyl-(L)-4-fluorophenylalanine | 568 |
| (263) | N-(3,5-dichlorobenzenesulfonyl)-(L)-2(S)-allylprolyl-(L)-4-fluorophenylalanine | 529 |
| (264) | N-(3,5-dichlorobenzenesulfonyl)-(L)-2(S)-methyl-prolyl-(L)-phenylalanine | |
| (265) | N-(3-trifluoromethylbenzenesulfonyl)-(L)-2(S)-methyl-prolyl-(L)-4-nitro-phenylalanine | 530 |
| (266) | N-(3,5-dichlorobenzenesulfonyl)-(L)-3(R)-methyl-prolyl-(L)-4-fluorophenylalanine | 502.3 |
| (267) | N-(3,5-dichlorobenzenesulfonyl)-(L)-2(S)-methyl-prolyl-(L)-4-cyanophenylalanine | 509 |
| (268) | N-(3,5-dichlorobenzenesulfonyl)-(L)-2(S)-methyl-prolyl-(L)-4-(aminocarbonyl)-phenylalanine | 545 |
| (269) | N-(3,5-dichlorobenzenesulfonyl)-(L)-3(R)-methyl-prolyl-(L)-4-(N-t-butoxycarbonylaminomethyl)-phenylalanine | 631.4 |
| (270) | N-(3,5-dichlorobenzenesulfonyl)-(L)-3(R)-methyl-prolyl-(L)-4-(aminomethyl)-phenylalanine | 514.3 |

*m/e: (M + 1 (H$^+$))$^+$ or (M + 18 (NH$_4^+$))$^+$
**(M − 159: N/SO$_2$Ar cleavage)

EXAMPLE 271

N-(3-Trifluoromethylphenylsulfonyl)-(L)-2(S)-methyl-prolyl-(L)-4-acetaminophenylalanine.

Step A: N-(3-trifluoromethylphenylsulfonyl)-(L)-2(S)-methyl-prolyl-(L)-4-aminophenylalanine, methyl ester.

To a solution of N-(3-trifluoromethylphenylsulfonyl)-(L)-2(S)-methyl-prolyl-(L)4-nitrophenylalanine, methyl ester (0.45 g, 0.85 mmol; prepared according to the methodology described in Example 225) in methanol (40 mL) was added 10% palladium on carbon catalyst (50 mg) and the resulting black suspension was stirred under 1 atm of hydrogen for 45 min. The reaction mixture was filtered (Whatman syringless filter device) and rotoevaporated under high vacuum to an off-white solid (0.42 g, 99% yield) which was used in the following step without further purification.

$^1$H-NMR (400 MHz, CDCl$_3$): δ 8.12 (s, 1H), 8.05 (d, 1H, J=7.8 Hz), 7.81 (d, 1H, J=7.7 Hz), 7.64 (t, 1H, J=−7.9 Hz), 7.03 (d, 1H, J=7.6 Hz), 6.97 (d, 2H, J=8.4 Hz), 6.73 (d, 2H, J=8.4), 4.76 (m, 1H), 3.75 (s, 3H), 3.48 (m, 1H), 3.28 (m, 1H), 3.14 (dd, 1H, J=14.2, 5.4 Hz), 2.98 (dd, 1H, J=14.2, 6.9 Hz), 2.29 (m, 1H), 1.78 (m, 1H), 1.62 (m, 2H), 1.57 (s, 3H).

Step B: N-(3-trifluoromethylphenylsulfonyl)-(L)-2(S)-methyl-prolyl-(L)-4-acetaminophenylalanine, methyl ester To a solution of N-(3-trifluoromethylphenylsulfonyl)-(L)-2(S)-methyl-prolyl-(L)-4-aminophenylalanine, methyl ester (42 mg, 0.082 mmol) in dry dichloromethane (0.5 mL) at 0° C., was added successively 2,6-lutidine (0.03 mL, 0.25 mmol; 3.0 equiv), acetyl chloride (0.01 mL, 0.125 mmol; 1.5 equiv), and 4-dimethylaminopyridine (10 mg, 0.082 mmol; 1.0 equiv). The yellow reaction mixture was stirred overnight. After this time, 1.0 N hydrochloric acid was added followed by extraction with ethyl acetate (3×). The combined organic layer was successively washed with saturated sodium bicarbonate solution and saturated salt solution and dried over anhydrous magnesium sulfate. The mixture was filtered and concentrated to furnish an orange-yellow oil (46 mg, 100% crude yield) which was purified by preparative thin layer chromatography (80% ethyl acetate, 20% hexanes). Yield: 39 mg (85%).

$^1$H-NMR (400 MHz, CDCl$_3$): δ 8.11 (s, 1H), 8.04 (d, 1H, J=8.0 Hz), 7.82 (d, 1H, J=7.7 Hz), 7.64 (t, 1H, J=−7.9 Hz), 7.41 (d, 1H, J=8.4 Hz), 7.25 (s, 1H), 7.09 (d, 2H, J=8.4 Hz), 7.07 (d, 1H, J=−8.0 Hz), 4.80 (m, 1H), 3.75 (s, 3H), 3.49 (m, 1H), 3.24 (m, 2H), 3.04 (dd, 1H, J=−14.0, −7.0 Hz), 2.29 (m, 1H), 2.13 (s, 3H), 1.75 (m, 1H), 1.61 (m, 2H), 1.57 (s, 3H).

Step C: N-(3-trifluoromethylphenylsulfonyl)-(L)-2(S)-methyl-prolyl-(L)-4-acetaminophenylalanine.

To a solution of N-(3-trifluoromethyl)-2(S)-methyl-prolyl-4-acetamino-(S)-phenylalanine, methyl ester (33 mg, 0.059 mmol) in ethanol (1.0 mL) was added 0.2 N sodium hydroxide solution (0.60 mL, 0.12 mmol; 2.0 equiv). The reaction mixture was stirred overnight (16 h) and then acidified with 1.0 N hydrochloric acid and extracted with ethyl acetate (3×). The combined organic layer was washed with saturated salt solution, dried over anhydrous magnesium sulfate, and rotoevaporated to yield an off-white solid (31 mg, 97% yield).

MS: m/e 542 (M+H$^+$); 559 (M+NH$_4^+$).

$^1$H-NMR (400 MHz, CD$_3$OD): δ 8.08 (m, 2H), 7.95 (d, 1H, J=7.7 Hz), 7.76 (t, 1H, J=−7.9 Hz), 7.48 (m, 3H), 7.18 (d, 2H, J=8.4), 4.69 (m, 1H), 3.43 (m, 1H), 3.32 (m, 2H), 3.05 (dd, 1H, J=−14.0, −7.0 Hz), 2.12 (m, 1H), 2.08 (s, 3H), 1.71 (m, 3H), 1.56 (s, 3H).

The following compounds were prepared by the procedures described in Example 271 using the acyl or sulfonyl chloride or alkyl or aryl isocyanate:

| Ex. | Compound Name | MS* |
|---|---|---|
| (272) | N-(3-trifluoromethylphenylsulfonyl)-(L)-2(S)-methyl-prolyl-(L)-4-(N'-(2-toluyl)ureido)phenylalanine. | 633 |
| (273) | N-(3-trifluoromethylphenylsulfonyl)-(L)-2(S)-methyl-prolyl-(L)-4-(N'-(4'-fluorophenylsulfonyl)ureido)phenylalanine. | 718 |
| (274) | N-(3-trifluoromethylphenylsulfonyl)-(L)-2(S)-methyl-prolyl-(L)-4-(ethoxycarbonyl)aminophenylalanine. | 572 |
| (275) | N-(3-trifluoromethylphenylsulfonyl)-(L)-2(S)-methyl-prolyl-(L)-4-(4'-(N'-(2-toluyl)ureido)phenylacetyl)aminophenylalanine. | 766 |
| (276) | N-(a-trifluoromethylphenylsulfonyl)-(L)-2(S)-methyl-prolyl-(L)-4-(4'-fluorophenylsulfonyl)aminophenylalanine. | 658 |
| (277) | N-(3-trifluoromethylphenylsulfonyl)-(L)-2(S)-methyl-prolyl-(L)-4-(phenylacetyl)aminophenylalanine. | 618 |
| (278) | N-(3-trifluoromethylphenylsulfonyl)-(L)-2(S)-methyl-prolyl-(L)-4-(4'-fluorobenzoyl)aminophenylalanine. | 622 |
| (279) | N-(3-trifluoromethylphenylsulfonyl)-(L)-2(S)-methyl-prolyl-(L)-4-(isobutyloxycarbonyl)aminophenylalanine. | 600 |
| (280) | N-(3-trifluoromethylphenylsulfonyl)-(L)-2(S)-methyl-prolyl-(L)-4-methylsulfonylaminophenylalanine. | 578 |
| (281) | N-(3-trifluoromethylphenylsulfonyl)-(L)-2(S)-methyl-prolyl-(L)-4-(N'-(4-fluorophenyl)ureido)phenylalanine. | 637 |
| (282) | N-(3-trifluoromethylbenzenesulfonyl)-(L)-2(S)-methyl-proyly-(L)-4-(N-(1,1-dioxo-1,2-isothiazolidinyl)-phenylalanine | 621 |
| (283) | N-(3-trifluoromethylphenylsulfonyl)-(L)-2(S)-methyl-prolyl-(L)-4-(N'-(4-(2-oxo-1-pyrrolidinyl)-phenylalanine. | 585 |

*m/e: $(M + 1 (H^+))^+$ or $(M + 18 (NH_4^+))^+$

EXAMPLE 284

N-(3.5-dichorobenzenesulfonyl)-(L)-prolyl-(L)-4-(4'-fluorobenzoyl)phenylalanine

Step A: 4-Iodo-(L)-Phenylalanine, tert-butyl ester hydrochloride.

To a suspension of N-Boc-4-iodo-(L)-phenylalanine (1.0 g, 2.56 mmol) in methylene chloride (7 mL) and cyclohexane (14 mL) were added t-butyl trichloroacetimidate (0.48 mL, 2.68 mmol) and boron trifluoride-etherate (48 μL). The reaction mixture was stirred for 5 hours at room temperature under a nitrogen atmosphere and then treated a second time with the same amounts of t-butyl trichloroacetimidate and boron trifluoride-etherate as above. After stirring overnight, a third addition was made, and the mixture was stirred a further 3 hours. The mixture was then filtered and the filtrate evaporated. The product was obtained pure by silica gel chromatography eluting with 10% diethyl ether in hexane; yield 650 mg. The product was treated with 1M HCl in ethyl acetate (7.3 mL) for 18 hours at room temperature. The mixture was evaporated and coevaporated several times with diethyl ether to afford the title compound; yield 522 mg.

400 MHz $^1$H NMR (CD$_3$OD): δ 1.42 (s, 9H); 3.13 (d, 2H); 4.18 (t, 1H); 7.09 (d, 2H); 7.75 (d, 2H).

Step B: N-(3,5-Dichlorobenzenesulfonyl)-(L)-proline

To a mixture of (L)-proline methyl ester hydrochloride (838 mg, 5.06 mmol) in methylene chloride (25 mL) at 0° C. were added N,N-diisopropylethylamine (2.64 mL, 15.2 mmol) and a solution of 3,5-dichlorobenzenesulfonyl chloride (1.49 g, 6.07 mmol) in methylene chloride (5 mL). The cooling bath was removed, and the mixture was stirred overnight at room temperature. It was then diluted with methylene chloride, washed with 1N hydrochloric acid, saturated NaHCO$_3$, saturated brine solution, dried over anhydrous sodium sulfate, and evaporated. The methyl ester was obtained pure by silica gel chromatography eluting with 10% acetone in hexane; yield 1.49 g. It was then taken up in ethanol (50 mL) and treated with 0.2 N sodium hydroxide (26.6 mL) for 1.5 hours at room temperature. The mixture was acidified with glacial acetic acid, concentrated, the residue taken up in methylene chloride, washed with water, saturated brine solution, dried (Na$_2$SO$_4$), and evaporated to give the title compound; yield 1.4 g.

400 MHz 111 NMR (CD$_3$OD): δ 1.80–2.15 (m, 4H); 3.35–4.45 (m, 2H); 4.30 (dd, 1H); 7.76 (m, 1H); 7.83 (m, 2H).

Step C: N-(3,5-Dichlorobenzenesulfonyl)-(L)-prolyl-(L)-4-iodophenylalanine, tert-butyl ester.

To a solution of N-(3,5-dichlorobenzenesulfonyl)-(L)-proline (386 mg, 1.19 mmol) in methylene chloride (23 mL) were added 1-hydroxybenzotriazole (241 mg, 1.79 mmol), N-methylmorpholine (0.33 mL, 2.98 mmol), and 4-iodo-(L)-phenylalanine tert-butyl ester hydrochloride (458 mg, 1.19 mmol). After cooling in an ice-bath for 5 minutes, 1-(3-dimethylaminopropyl)-3-ethylcarbodiimide hydrochloride (EDC) (274 mg, 1.43 mmol) was added. After 15 minutes, the cooling bath was removed, and the mixture was stirred overnight under a nitrogen atmosphere. The mixture was diluted with methylene chloride, washed with water, 1N HCl, saturated NaHCO$_3$ solution, saturated brine solution, dried (Anhydrous magnesium sulfate), and evaporated. Silica gel chromatography eluting with 20% ethyl acetate in hexane afforded pure title compound; yield 651 mg (84%).

MS: m/e 653 (M+1)

400 MHz $^1$H NMR (CD$_3$OD): δ 1.45 (s, 9H); 1.65–1.85 (m, 4H); 3.0 (dd, 1); 3.13 (dd, 1H); 3.45 (m, 1H); 4.20 (m, 1H) 4.55 (dd, 1H); 7.05 (d, 2H); 7.64 (d, 2H); 7.80 (s, 3H).

Step D: N-(3.5-dichlorobenzenesulfonyl)-(L)-prolyl-(L)-4-(4'-fluorobenzoyl)phenylalanine, tert-butyl ester, A solution of N-(3,5-dichlorobenzenesulfonyl)-(L)-prolyl-4-iodo-(L)-phenylalanine tert-butyl ester(100 mg, 0.15 mmol), 4-fluorobenzeneboronic acid (23 mg, 0.16 mmol), potassium carbonate(62 mg, 0.45 mmol), bis(triphenylphosphine)-palladium(II) chloride (4 mg, 0.0057 mmol) in anisole(4 ml) was flushed with nitrogen, then flushed with CO, and a balloon of CO was attached. The solution was then stirred at 80° C. for 5 hours on a timer overnight. The following day the solution was diluted with methylene chloride, washed once with water, once with brine, dried over Anhydrous magnesium sulfate, and solvent removed in vacuo. The desired product was obtained by silica gel chromatography eluting with methylene chloride, followed by 10% ethyl acetate in methylene chloride; yield 70 mg (72%)

MS: m/e 666.2 (M+H+NH$_3$)

400 MHz $^1$H NMR (CD$_3$OD): δ 1.46(s,9H); 1.65–1.95 (m,4H); 3.05–3.15 (dd,1H); 3.47(m,1H); 4.2(dd,1H); 4.65 (m,1H); 7.20(t,2H); 7.45(d,2H); 7.70(d,2H);7.76–7.85(m, 6H)

Step E: N-(3,5-dichlorobenzenesulfonyl)-(L)-prolyl-(L)-4-(4'-fluorobenzoyl)phenylalanine A solution of N-(3,5-dichlorobenzenesulfonyl)-(L)-prolyl-(L)-4-(4-fluorobenzoyl)phenylalanine, tert-butyl ester (23 mg, 0.035 mmol) in methylene chloride(1.2 mL) was cooled in ice bath. Trifluoroacetic acid (0.167 mL, 2.17 mmol) was then added, and ice bath was removed and reaction mixture was allowed to stir overnight at room temperature. The reaction mixture was then evaporated, coevaporated with methylene chloride(2×), toluene(2×), and methanol(2×). The product was obtained pure by eluting with 20% ethyl acetate in methylene chloride, followed by 8% methanol in methylene chloride; yield 19 mg(91%)

MS: m/e 609.8(M+H+NH$_3$)

400 Mhz $^1$H NMR (CD$_3$OD): δ 1.6–1.95(m,4H): 3.1–3.45 (m,4H): 4.17 (dd,1H): 4.55(m,1H): 7.2(t,2H): 7.4(d,2H): 7.66(d,2H): 7.78–7.85(m,5H)

The following compounds were prepared by the procedures described in Example 284 using the appropriate arylboronic acid derivative in Step D:

| Ex. | Compound Name | MS* |
|---|---|---|
| (285) | N-(3,5-dichlorobenzenesulfonyl)-(L)-prolyl-(L)-4-(4'-(2-methoxybenzoyl)phenylalanine | 604.08 |
| (286) | N-(3,5-dichorobenzenesulfonyl)-(L)-2(S)-methyl-prolyl-(L)-4-(4'-fluorobenzoyl)phenylalanine | 624 |

*m/e: (M + 1 (H$^+$))$^+$ or (M + 18 (NH$_4^+$))$^+$

EXAMPLE 287
N-(3.5-dichlorobenzenesulfonyl)-(L)-prolyl-(L)-4-(4-fluorobenzyl)phenyl alanine Step A: N-(3.5-dichlorobenzenesulfonyl)-(L)-prolyl-(L)-4-(4-fluoro-α-hydroxybenzyl)phenylalanine, tert-butyl ester, A solution of N-(3,5-dichorobenzenesulfonyl)-(L)-prolyl-(L)-4-(4'-fluorobenzoyl)phenylalanine (38 mg) in methanol (5 mL) was cooled to 0° C. Sodium borohydride (3 mg) was added. After stirring for 20 min, the solvent was removed by rotoevaporation and the residue dissolved in dichloromethane (30 mL). The solution was successively washed with water and saturated salt solution and dried over anhydrous magnesium sulfate. The mixture was filtered and the solvent was removed by rotoevaporation. The title compound (38 mg) was recovered and used with no further purification in the subsequent reaction.

Step B: N-(3.5-dichlorobenzenesulfonyl)-(L)-prolyl-(L)-4-(4-fluorobenzyl)phenylalanine A solution of N-(3,5-dichlorobenzenesulfonyl)-(L)-prolyl-(L)-4-(4-fluorophenyl-hydroxymethyl) phenylalanine, tert-butyl ester (38 mg) and triethylsilane (21 μL) in anhydrous dichloromethane was flushed with dry nitrogen for five minutes. The solution was then cooled in an ice bath and boron trifluoride etherate (16 μL) was added. After stirring for 3 hours, methanol (1 mL) was added and the solvent was removed by rotoevaporation. The residue was dissolved in ethyl acetate and the solution successively washed with saturated sodium bicarbonate solution and saturated salt solution and then dried over anhydrous magnesium sulfate. After the mixture was filtered, the solvent was removed by rotoevaporation. The residue was purified by flash column chromatography on silica gel eluted with 97.75% dichloromethante, 2% methanol and 0.25% acetic acid to yield the title compound (14 mg).

M/S: m/e=597.2 (M+NH$_4$).

$^1$H NMR (400 MHz, CD$_3$OD): δ 1.5–1.7 (m, 2H), 1.75–1.82 (m, 2H), 2.95–3.05 (m, 1H), 3.2–3.4 (m, 3H), 3.88 (s, 2H), 4.1–4.2 (m, 1H), 4.6–4.7 (m, 1H), 6.90 (t, J=9, 2H), 7.1–7.22 (m, 6H), 7.72 (s, 2H), 7.76 (s, 1H).

The following compounds were prepared by the procedures described in Example 287:

| Ex. | Compound Name | MS* |
|---|---|---|
| (288) | N-(3,5-dichlorobenzenesulfonyl)-(L)-prolyl-(L)-4-(2-methoxybenzyl)phenylalanine | 608.3 |

*m/e: (M + 1 (H$^+$))$^+$ or (M + 18 (NH$_4^+$))$^+$

EXAMPLE 289
N-(3.5-Dichlorobenzenesulfonyl)-(L)-prolyl-(L)-4-(2-nitrophenoxy)-phenylalanine Step A: N-Boc-4-(2-nitrophenoxy)-(L)-phenylalanine, methyl ester To a solution of N-Boc-(L)tyrosine, methyl ester (500 mg) and potassium carbonate (467 mg) in dimethylformamide (5 mL) was added dropwise 1-fluoro-2-nitrobenzene (189 μL). The yellow solution was stirred for 3 days at room temperature. The mixture was diluted with ether which was subsequently washed with 1N hydrochloric acid, water, saturated salt solution and dried over anhydrous magnesium sulfate. After filtration, the solvent was removed by rotoevaporation to yield the title compound (700 mg) which was used in the subsequent reaction without further purification.

$^1$H NMR (400 MHz, CD$_3$OD): δ 1.38 (s, 9H), 3.85–3.15 (m, 2H), 4.3–4.4(m, 1H), 6.95–7.1 (m, 3H), 7.24–7.3(m, 3H), 7.55–7.61 (t, 1H), 7.97–7.97(m, 1H).

Step B: 4-(2-nitrophenoxy)-(L)-phenylalanine methyl ester hydrochloride

N-Boc-4-(2-nitrophenoxy)-(L)-phenylalanine, methyl ester (600 mg) was stirred in a solution of 1N hydrochloric acid in ethyl acetate (10 mL) for 18 hours at room temperature. A precipitate formed, the solvent was removed by rotoevaporation, and co-evaporated with Et$_2$O (2×). The solid was than suspended with ethyl acetate, filtered, washed with diethyl ether, and allowed to air dry. The title compound was recovered (490 mg) and used in the subsequent reaction without further purification.

Step C: N-(3,5-Dichlorobenzenesulfonyl)-(L)-prolyl-(L)-4-(2-nitrophenoxy)phenylalanine, methyl ester.

A solution of N-(3,5-dichlorobenzenesulfonyl)-(L)-proline (429 mg), 4-(2-nitrophenoxy)-(L)-phenylalanine, methyl ester hydrochloride (445 mg), 1-hydroxybenztriazole (255 mg), N-methylmorpholine (0.35 mL) in dichloromethane (32 mL) was cooled to 0° C. 1-(3-dimethylaminopropyl)-3-ethylcarbodiimide hydrochloride (EDC; 289 mg) was then added. The reaction was allowed to warm to room temperature and stirred for 17 hr. The reaction was diluted with dichloromethane (100 mL) and successively washed with water, 1N hydrochloric acid, saturated sodium bicarbonate solution, and saturated salt solution. The organic layer was dried over anhydrous magnesium sulfate. The solution was filtered and the solvent removed by rotoevaporation. The residue was purified by flash column chromatography on silica gel eluted with 20% ethyl acetate in hexane to afford the title compound (714 mg) which was used in the subsequent reaction.

Step D: N-(3,5-Dichlorobenzenesulfonyl)-(L)-prolyl-(L)-4-(2-nitrophenoxy)-phenylalanine N-(3,5-Dichlorobenzenesulfonyl)-(L)-prolyl-(L)-4-(2-nitrophenoxy)-phenylalanine, methyl ester (110 mg) was dissolved in ethanol (6 mL) and a solution of potassium hydroxide (15 mg) in water (2 mL) was added. After stirring for 20 minutes, the reaction was acidified with acetic acid and the solvent removed by rotoevaporation. The residue was dissolved in ethyl acetate (40 mL), and the solution successively washed with saturated sodium bicarbonate solution and saturated salt solution. The solution was dried over anhydrouus magnesium sulfate, then filtered and the solvent removed by rotoevaporation to afford the title compound (40 mg).

M/S: m/e 625(M+NH$_4$)$^+$.

$^1$H NMR (400 MHz, CD$_3$OD): δ 1.63–1.72(m, 1H), 1.75–2.92(m, 3H), 3.01–3.08(dd, 1H), 3.25–3.35(m, 2H), 3.4–3.5 (m, 1H), 4.19 (dd, J=6,1, 1H), 4.68–4.74 (m, 1H), 6.97–7.05 (m, 3H), 7.2–7.35 (m, 3H), 7.45–7.5 (m, 1H), 7.77 (s, 3H), 7.91 (dd, J=7,2, 1H).

The following compound was prepared by the procedures described in Example 289:

| Example | Compound Name | MS* |
|---|---|---|
| (290) | N-(3,5-dichlorobenzenesulfonyl)-(L)-prolyl-(L)-4-(4-nitrophenoxy)-phenylalanine | 625 |
| (291) | N-(3,5-dichlorobenzenesulfonyl)-(L)-2(S)-methyl-prolyl-(L)-4-(2-nitrophenoxy)-phenylalanine | 639 |

*m/e: (M + 1 (H$^+$))$^+$ or (M + 18 (NH$_4^+$))$^+$

EXAMPLE 292
N-(3,5-Dichlorobenzenesulfonyl)-(L)-prolyl-(L)-4-(2-aminophenoxy)-phenylalanine Step A: N-(3.5-Dichlorobenzenesulfonyl)-(L)-prolyl-(L)-4-(2-aminophenoxy)-phenylalanine, methyl ester To a solution of N-(3,5-dichlorobenzenesulfonyl)-(L)-prolyl-(L)-4-(2-nitro-phenoxy)-phenylalanine, methyl ester (120 mg) in ethanol (4.5 mL) was added iron filings (42 mg) and acetic acid (0.5 mL). Reaction was refluxed for 3 h then cooled to room temperature. The mixture was filtered through a pad of celite and the solvent was removed by rotoevaporation. The resultant tar was dissolved in ethyl acetate and successively washed with saturated sodium bicarbonate solution and saturated salt solution. The organic layer was dried over anhydrous magnesium sulfate, filtered and the solvent removed by rotoevaporation. The residue was purified by flash column chromatography on silica gel eluted with 40% ethyl acetate in hexane to afford N-(3,5-dichlorobenzenesulfonyl)-(L)-prolyl-(L)-4-(2-aminophenoxy)-phenylalanine, methyl ester (75 mg) which was used in the subsequent reaction.

Step B: N-(3.5-Dichlorobenzenesulfonyl)-(L)-prolyl-(L)-4-(2-aminophenoxy)-phenylalanine N-(3,5-dichlorobenzenesulfonyl)-(L)-prolyl-(L)-4-(2-aminophenoxy)-phenylalanine, methyl ester was hydrolyzed by the procedure in Example 289, step D to afford N-(3,5-dichlorobenzenesulfonyl)-(L)-prolyl-(L)-4-(2-aminophenoxy)-phenylalanine.

M/S: m/e 578(M+1).

$^1$H NMR (400 MHz, CD$_3$OD): δ 1.62–1.9 (m, 4H), 3.0–3.07 (dd, 1H), 3.2–3.3(m, 2H), 3.4–3.5 (m, 1H), 4.19 (t, 1H), 4.62–4.7 (m, 1H), 6.6–6.65 (m, 1H), 6.73–6.77 (dd, 1H), 6.85–6.95 (m, 4H), 7.2 (d, J=2, 2H), 7.78 (s, 3H), 8.1–8.15 (d, 1H).

EXAMPLE 293
N-(3.5-Dichlorobenzenesulfonyl)-(L)-prolyl-(L)-4-(2-acetylaminophenoxy)-phenylalanine Step A: N-(3.5-Dichlorobenzenesulfonyl)-(L)-prolyl-(L)-4-(2-acetylaminophenoxy)-phenylalanine, methyl ester To a solution of N-(3,5-dichlorobenzenesulfonyl)-(L)-prolyl-(L)-4-(2-amino-phenoxy)-phenylalanine, methyl ester (55 mg) in pyridine (0.31 mL) and dichloromethane (4 mL) was dropwise added acetic anhydride (0.16 mL). After stirring for 1 hr, the reaction was diluted with dichloromethane (50 mL) and successively washed with water and saturated salt solution. The solution was dried over anhydrous magnesium sulfate, filtered and the solvent removed by rotoevaporation. The residue was purified by flash column chromatography on silica gel eluted with 5% ethyl acetate in dichloromethane to afford N-(3,5-dichlorobenzenesulfonyl)-(L)-prolyl-(L)4-(2-acetylaminophenoxy)-phenylalanine, methyl ester (41 mg) which was used in the subsequent reaction.

Step B: N-(3.5-Dichlorobenzenesulfonyl)-(L)-prolyl-(L)-4-(2-acetylaminophenoxy)-phenylalanine N-(3,5-dichlorobenzenesulfonyl)-(L)-prolyl-(L)-4-(2-acetylaminophenoxy)-phenylalanine, methyl ester was hydrolyzed by the procedure in Example 289, step D to afford N-(3,5-dichlorobenzenesulfonyl)-(L)-prolyl-(L)-4-(2-acetylaminophenoxy)-phenylalanine.

M/S: m/e 637(M+NH$_4$)$^+$.

$^1$H NMR (400 MHz, CD$_3$OD): d 1.6–1.95 (m, 4H), 2.06 (s, 3H), 3.0–3.08 (dd, 1H), 3.2–3.3 (m, 2H), 3.4–3.48 (m, 1H), 4.15–4.2 (m, 1H), 5.55–5.61 (m, 1H), 6.8–6.85 (d, 1H), 6.91 (d, J=9, 2H), 6.98–7.08 (m, 2H), 7.26 (d, J=9, 2H), 7.78 (s, 3H), 8.85–8.90 (dd, 1H).

The following compounds were prepared by the procedures described in Example 293:

| Ex. | Compound Name | MS* |
|---|---|---|
| (294) | N-(3,5-dichlorobenzenesulfonyl)-(L)-prolyl-(L)-4-(4-acetylaminophenoxy)-phenylalanine | 637 |
| (295) | N-(3,5-dichlorobenzenesulfonyl)-(L)-2(S)-methylprolyl-(L)-4-(2-acetylaminophenoxy)-phenylalanine | 636 |

*m/e: (M + 1 (H$^+$))$^+$ or (M + 18 (NH$_4^+$))$^+$

EXAMPLE 296

N-(3.5-Dichlorobenzenesulfonyl)-2-(S)-methyl-(L)-prolyl-4-(2-cyanophenoxy)-phenylalanine Step A: N-Boc-4-(2-cyanophenoxy)-phenylalanine, methyl ester A solution of 500 mg of N-Boc-4-(L)-tyrosine, methyl ester, 205 mg 2-fluorobenzonitrile, 245 mg KF 40 wt % on alumina, 45 mg 18-crown-6, and 7 mL of acetonitrile was run at reflux for seven days. The reaction was then diluted with methylene chloride, and washed with water and saturated salt solution. The organic layers were then dried over anhydrous magnesium sulfate and the solvent was removed in vacuo. The product was purified via silica gel chromatography eluted with 80% hexane:20% acetone to yield 253 mg of the product.

$^1$H NMR (400 Mhz, CD$_3$OD): δ 1.38(s, 9H), 2.9(dd, 1H), 3.13(dd, 1H), 3.70(s, 3H), 3.38(m, 1H), 6.88(d, 1H), 7.03 (d, J=9, 2H), 7.2(t, 1H), 7.29(d, J=9, 2H), 7.55(t, 1H), 7.72,(d, 1H).

Step B: 4-(2-cyanophenoxy)-phenylalanine, methyl ester, hydrochloride

The reaction was performed by an analogous procedure as described in Example 289, step B to yield the title compound.

Step C: N-Boc-2-(S)-methyl-(L)-prolyl-4-(2-cyanophenoxy)-phenylalanine, methyl ester To a solution of 131 mg of N-Boc-2-(S)-methyl-(L)-proline, 190 mg 4-(2-cyanophenoxy)-phenylalanine, methyl ester hydrochloride, 297 mg PyBOP, and 4 mL of methylene chloride at 0° C. was added 300 μL of diisopropylethylamine via syringe. The reactants were allowed to warm to room temperature and said reaction was run over the weekend.

The reaction was then diluted with methylene chloride, washed with water, 1N hydrochloric acid), saturated sodium bicarbonate solution, and saturated salt solution. The organic layer was dried over anhydrous magnesium sulfate and concentrated in vacuo. The product was purified via silica gel chromatography, eluted with 80% hexane:20% acetone to yield 263 mg of the title compound.

Step D: N-Boc-2-(S)-methyl-(L)-prolyl-4-(2-cyanophenoxy)-phenylalanine, methyl ester hydrochloride The reaction was performed by an analogous procedure as described in Example 289, step B to yield the title compound.

Step E: N-(3.5-Dichlorobenzenesulfonyl)-2-(S)-methyl-(L)-prolyl-4-(2-cyanophenoxy)-phenylalanine, methyl ester To a solution of 95 mg of N-Boc-2-(S)-methyl-(L)-prolyl-4-(2-cyanophenoxy)-phenylalanine, hydrochloride, 61 mg 3,5-dichlorobenzenesulfonyl chloride, and 2.5 mL of tetrahydrofuran at 0° C. was added 110 uL of diisopropylethylamine via syringe. The reaction was allowed to warm to room temperature and run at said temperature overnight. The reaction was diluted with methylene chloride, washed with water, 1N hydrochloric acid, saturated sodium bicarbonate solution, and saturated salt solution. The organic layer was dried over anhydrous magnesium sulfate and concentrated in vacuo. The product was purified via silica gel chromatography, eluted with 80% hexane:20% acetone to yield 62 mg of of N-(3,5-dichlorobenzenesulfonyl)-2-(S)-methyl-(L)-prolyl-4-(2-cyanophenoxy)-phenylalanine, methyl ester.

Step F: N-(3.5-Dichlorobenzenesulfonyl)-2-(S)-methyl-(L)-prolyl-4-(2-cyanophenoxy)-phenylalanine To a solution of 62 mg of N-(3,5-dichlorobenzenesulfonyl)-2-(S)-methyl-(L)-prolyl-4-(2-cyanophenoxy)-phenylalanine, methyl ester in mL of ethanol was added a solution of 11 mg potassium hydroxide in 2 mL of water. After 1.5 hours the solvent was removed in vacuo. The resultant solid was then dissolve in methylene chloride and washed with 0.5 M hydrochloric acid and saturated salt solution. The organic layers were dried over anhydrous magnesium sulfate and concentrated in vacuo. The formed diastereomers were separated via HPLC using a YMC ODS-AQ column, eluting with 80% MeOH: 20% WATER+0.1% TFA. The faster eluting product was shown to be the desired product.

M/S: m/e 619 (M+1+NH$_3$).

$^1$H NMR (400 Mhz, CD$_3$OD): δ 1.60(s, 3H), 1.7–1.9(m, 3H), 2.12–2.21(m, 1H), 3.08–3.16(dd, 1H), 3.3–3.5(m), 4.65–4.75(m, 1H), 6.91(d, J=8 1H), 7.04(d, 2H), 7.15 (t, 1H), 7.36 (d, J=9, 2H), 7.4–7.5 (t, 1H), 7.6–7.8(m, 4H).

The following compound was prepared by the procedures described in Example 296:

| Ex. | Compound Name | MS* |
|---|---|---|
| (297) | N-(3,5-Dichlorobenzenesulfonyl)-2-(S)-methyl-(L)-prolyl-4-(4-cyanophenoxy)-phenylalanine | 619 |

EXAMPLE 298

N-(3,5-Dichlorobenzenesulfonyl)-(L)-prolyl-(L)-O-tert-butyl-tyrosine.

Step A: N-(3.5-Dichlorobenzenesulfonyl)-(L)-prolyl-(L)-O-tert-butyl-tyrosine, methyl ester.

To a solution of 3,5-dichlorobenzenesulfonyl-(L)-proline (from Example 284, Step B) (1.70 gm, 5.23 mmole) in dry dichloromethane (15 mL) was added 1-hydroxybenzotriazole hydrate (782.3 mg, 5.78 mmole) followed by N-methylmorpholine (1.45 mL, 13.1 mmole), (L)-O-tert-butyl-tyrosine, methyl ester hydrochloride (1.58 gm, 6.31 mmole), and 1-ethyl-3-(3-dimethylamino-propyl) carbodiimide (1.41 gm, 7.36 mmole). Additional dichloromethane (5 mL) was added and the solution stirred under nitrogen at 25° C. overnight. Water was added and the layers separated. The aqueous layer was extracted with ethyl acetate (3×15 mL). The combined organic layers were successively washed with water (2×20 mL) and saturated salt solution and dried over anhydrous magnesium sulfate. After filtration, the solvent was removed by rotoevaporation. The residue was purified by flash column chromatography on silica gel eluted with 5–35% ethyl acetate in hexanes to yield N-(3,5-dichlorobenzenesulfonyl)-(L)-prolyl-(L)-O-tert-butyl-tyrosine, methyl ester as a pale white foam (2.85 gm, 98% yield).

MS: m/e 557.4 (M+1)$^+$.

400 MHz $^1$H NMR (CD$_3$OD): δ 1.28 (s, 9H), 1.49–1.66 (m, 3H), 2.03–2.07 (m, 1H), 2.99 (dd, J=14.0, 7.5 Hz, 1H), 3.06–3.12 (m, 1H), 3.19 (dd, J=14.1, 5.5 Hz, 1H), 3.34–3.39 (m, 1H), 3.74 (s, 3H), 4.04–4.07 (m, 1H), 4.76–4.81 (m, 1H), 6.88 (d, J=8.4 Hz, 2H), 6.99 (d, J=8.4 Hz, 3H), 7.58 (t, J=1.8 Hz, 1H), 7.69 (d, J=1.8 Hz, 2H).

Step B: N-(3.5-Dichlorobenzenesulfonyl)-(L)-prolyl-(L)-O-tert-butyl-tyrosine.

Under a dry nitrogen atmosphere, to a solution of 1.20 gm (2.15 mmole) of N-(3,5-dichlorobenzenesulfonyl)-(L)-prolyl-(L)-O-tert-butyl-tyrosine, methyl ester (1.20 gm, 2.15 mmole) in dry ethanol 25.8 mL) was added dropwise an aqueous 0.2N sodium hydroxide solution (12.9 mL, 2.58 mmole). The reaction was stirred for 1.5 hr at room temperature. A 1.0M aqueous solution of acetic acid (~2 mL) was added until pH 4–5 was obtained. The solvent was removed by rotoevaporation and the residue dissolved in dichloromethane and water. The layers were separated and the aqueous layer was extracted with dichloromethane (3×20 mL). The organic layers were combined, and successively washed with water, saturated salt solution, and dried over anhydrous sodium sulfate. After filtration, the solvent was removed by rotoevaporation. The residue dissolved in a minimum of dichloromethane and purified on a 4000 μm silica gel plate on a Chromatotron, eluted with 1–10% methanol in dichloromethane to yield N-(3,5-dichlorobenzenesulfonyl)-(L)-prolyl-(L)-O-tert-butyl-tyrosine as a pale yellow foam (1.15 gm, 99% yield).

MS: m/e 543.3 (M+1)$^+$.

400 MHz NMR (CD$_3$OD) δ 1.28 (s, 9H), 1.60–1.69 (m, 1H), 1.70–1.79 (m, 1H), 1.82–1.89 (m, 2H), 3.02–3.06 (m, 1H), 3.21–3.30 (m, 4H), 3.41–3.49 (m, 1H), 4.19 (br t, J=6.60 Hz, 1H), 4.62 (br s, 1H), 6.90 (d, J=8.3 Hz, 2H), 7.18 (d, J=8.4 Hz, 2H), 7.78 (s, 3H).

EXAMPLE 299

N-(3.5-Dichlorobenzenesulfonyl)-(L)-prolyl-(L)-O-methyl-tyrosine.

Step A: N-(3.5-Dichlorobenzenesulfonyl)-(L)-prolyl-(L)-O-tert-butyl-tyrosine, tert-butyl ester By the procedure of Example 284, step C, N-(3,5-dichlorobenzenesulfonyl)-(L)-proline was coupled with (L)-O-tert-butyl-tyrosine, tert-butyl ester hydrochloride. The product was purified by flash column chromatography on silica gel eluted with 5–35% ethyl acetate in hexane and isolated as a white foam (85% yield).

MS: m/e 599.0 (M+1)$^+$.

400 Mhz $^1$H NMR (CDCl$_3$) δ 1.28 (s, 9H), 1.42 (s, 9H), 1.56–1.63 (m, 4H), 2.05–2.08 (m, 1H), 2.99 (dd, J=14.0, 6.7 Hz, 1H), 3.09–3:17 (m, 2H), 3.35–3.38 (m, 1H), 4.06–4.08

(m, 1H), 4.67 (br dd, J=14.0, 6.3 Hz, 1H), 6.87 (br d, J=8.5 Hz, 2H), 7.03 (br d, J=8.4 Hz, 3H), 7.06(br d, J=7.6 Hz, 1H), 7.57 (t, J=1.8 Hz, 1H), 7.70 (d, J=1.8 Hz, 2H).

Step B: N-(3,5-Dichlorobenzenesulfonyl)-(L)-prolyl-(L)-tyrosine tert-butyl ester To a solution of N-(3,5-dichlorobenzenesulfonyl)-(L)-prolyl-(L)-O-tert-butyl-tyrosine, tert-butyl ester (1.20 gm, 2.00 mmole) in dry dichloromethane (6 mL) at 0° C. under a dry nitrogen atmosphere was dropwise added a 50% v/v solution of trifluoroacetic acid in dichloromethane (3.08 mL, 20 mmol) over a 10 min period. After stirring for 2 hr, the reaction mixture was quenched at 0° C. with an aqueous 5% sodium bicarbonate solution to pH=7–8. The layers were separated and the organic layer dried over anhydrous magnesium sulfate. After filtration, the solvent was removed by rotoevaporation and the residue purified by flash column chromatography on silica gel eluted with 1–10% methanol in dichloromethane to yield N-(3,5-dichlorobenzenesulfonyl)-(L)-prolyl-(L)-tyrosine, tert-butyl ester as a white foam (1.71 gm, 78% yield).

MS: m/s 543.4 (M+1)$^+$.

400 MHz $^1$H NMR (CDCl$_3$) δ 1.45 (s, 9H), 1.55–1.63 (m, 3H), 2.07 (m, 1H), 2.94 (dd, J=14.1, 6.90 Hz, 1H), 3.09–3.16 (m, 2H), 3.37–3.39 (m, 1H), 4.06–4.09 (m, 1H), 4.65–4.70 (m, 1H), 6.71 (d, J=8.5 Hz, 2H), 7.01 (d, J=8.5 Hz, 2H), 7.06 (d, J=7.7 Hz, 1H), 7.58 (t, J=1.8 Hz, 1H), 7.70 (d, J=1.8 Hz, 2H).

Step C: N-(3.5-dichlorobenzenesulfonyl)-(L)-prolyl-(L)-O-methyl-tyrosine, tert-butyl ester To a solution of N-(3,5-dichlorobenzenesulfonyl)-(L)-prolyl-(L)-tyrosine, tert-butyl ester (100 mg, 0.184 mmole) dissolved in dry dimethylformamide (1.0 mL) was added anhydrous potassium carbonate (76.3 mg, 0.552 mmol) and iodomethane (52.3 mg, 0.736 mmole). The reaction mixture was stirred vigorously at 25° C. overnight under a dry nitrogen atmosphere. Ethyl acetate (30 mL) was added and the solution acidified with aqueous 5% citric acid to pH=5. The layers were separated and the aqueous layer was extracted with ethyl acetate (3×20 mL). Organic layers were combined and washed successively with water and saturated salt solution, and dried over anhydrous magnesium sulfate. After filtration, the solvent was removed by rotoevaporation and the residue dissolved in a minimum of dichloromethane. This solution was loaded onto a 1000 micron silica gel Chromatotron plate and purified by gradient elution with 10–50% ethyl acetate in hexane to afford N-(3,5-dichlorobenzenesulfonyl)-(L)-prolyl-(L)-O-methyl-tyrosine, tert-butyl ester as an off-white powder (76 mg, 74% yield).

MS: m/e 557.5 (M+1)$^+$.

400 MHz $^1$H-NMR (CDCl$_3$) δ 1.44 (s, 9H), 1.56–1.69 (m, 3H), 2.08–2.11 (m, 1H), 2.95 (dd, J=14.0, 6.68 Hz, 1H), 3.09–3.16 (m, 2H), 3.35–3.40 (m, 1H), 3.75 (s, 3H), 4.07–4.09 (m, 1H), 4.66 (dd, J=13.8, 6.4 Hz, 1H), 6.78 (d, J=8.4 Hz, 2H), 7.04 (d, J=8.6 Hz, 3H), 7.57 (t, J=1.8 Hz, 1H), 7.70 (d, J=1.8 Hz, 2H).

Step D: N-(3.5-Dichlorobenzenesulfonyl)-(L)-prolyl-(L)-O-methyl-tyrosine.

To a solution of N-(3,5-dichlorobenzenesulfonyl)-(L)-prolyl-(L)-O-methyl-tyrosine, tert-butyl ester (50 mg, 0.090 mmole) dissolved in dry dichloromethane (0.3 mL) and anisole (5 μL) at 0° C. under a dry nitrogen atmosphere was dropwise added a 50% v/v solution of trifluoroacetic acid in dichloromethane (276 μL, 1.8 mmole). After the addition was completed, the ice bath was removed, and the reaction mixture allowed to stir vigorously for 2.5 hr. The reaction mixture was treated with dichloromethane (20 mL) and 5% aqueous sodium bicarbonate to pH=5. After separation of phases, the aqueous layer was extracted with dichloromethane (2×10 mL). The organic layers were combined and successively washed with water and saturated salt solution. The solution was dried over anhydrous magnesium sulfate and filtered. The solvent was removed by rotoevaporation and the residue dissolved in a minimum of dichloromethane. This solution was loaded onto a 1000 micron silica gel plate on a Chromatotron eluted with 1–10% methanol in dichloromethane to afford N-(3,5-dichlorobenzenesulfonyl)-(L)-prolyl-(L)-O-methyl-tyrosine as a light brown powder (28.5 mg, 63% yield).

MS: m/e 501.2 (M+1)$^+$.

400 MHz $^1$H-NMR (CD$_3$OD) δ 1.56–1.65 (m, 2H), 1.74–1.85 (m, 1H), 1.86–1.88 (m, 1H), 3.01 (dd, J=13.9, 6.4 Hz, 1H), 3.16–3.24 (m, 2H), 3.37–3.43 (m, 1H), 3.72 (s, 3H), 4.12 (dd, J=8.5, 3.4 Hz, 1H), 4.45 (br t, J=5.7 Hz, 1H), 6.79 (d, J=8.6 Hz, 2H), 7.15 (d, J=8.6 Hz, 2H), 7.80 (br m, 3H).

The following compounds were prepared by the procedures described in Example 299 using the appropriate alkylating or acylating agent in Step C:

| Ex. | Compound Name | MS* |
|---|---|---|
| (300) | N-(3,5-dichlorobenzenesulfonyl)-(L)-prolyl-(L)-O-benzyl-tyrosine | 577.4 |
| (301) | N-(3,5-dichlorobenzenesulfonyl)-(L)-prolyl-(L)-O-n-butyl-tyrosine | 543.5 |
| (302) | N-(3,5-dichlorobenzenesulfonyl)-(L)-prolyl-(L)-O-cyanomethyl-tyrosine | 526.4 |
| (303) | N-(3,5-dichlorobenzenesulfonyl)-(L)-prolyl-(L)-O-(2-methoxyethyl)-tyrosine | 547.4 |
| (304) | N-(3,5-dichlorobenzenesulfonyl)-(L)-prolyl-(L)-O-(2-ethoxyethyl)-tyrosine | 559.4 |
| (305) | N-(benzenesulfonyl)-(L)-prolyl-(L)-O-(2-methoxyethyl)-tyrosine | 477.0 |
| (306) | N-(benzenesulfonyl)-(L)-prolyl-(L)-O-(2-ethoxyethyl)-tyrosine | 491.2 |
| (307) | N-(3,5-dichlorobenzenesulfonyl)-(L)-prolyl-(L)-O-(1-pyrrolidinylcarbonyl)-tyrosine | 584.3 |
| (308) | N-(benzenesulfonyl)-(L)-prolyl-(L)-O-(1-pyrrolidinylcarbonyl)-tyrosine | 516.3 |
| (309) | N-(3,5-dichlorobenzenesulfonyl)-(L)-prolyl-(L)-O-(tert-butyl acetate)-tyrosine | 618 |
| (310) | N-(3,5-dichlorobenzenesulfonyl)-(L)-prolyl-(L)-O-(4-morpholinyl-carbonyl)-tyrosine | 599.1 |
| (311) | N-(3,5-dichlorobenzenesulfonyl)-(L)-prolyl-(L)-O-(1-(2-propanonyl)-tyrosine | 543.3 |
| (312) | N-(3,5-dichlorobenzenesulfonyl)-(L)-prolyl-(L)-2(S)-methyl-prolyl-(L)-O-(1-pyrrolidinylcarbonyl)-tyrosine | 598 |
| (313) | N-(3,5-dichlorobenzenesulfonyl)-(L)-prolyl-(L)-2(S)-methyl-prolyl-(L)-O-(tert-butyl acetate)-tyrosine | 632.1 |
| (314) | N-(3,5-dichlorobenzenesulfonyl)-(L)-prolyl-(L)-2(S)-methyl-prolyl-(L)-O-(2-ethoxyethyl)-tyrosine | 559.3 |
| (315) | N-(3,5-dichlorobenzenesulfonyl)-(L)-prolyl-(L)-O-(acetic acid)-tyrosine, methyl ester | 559.4 |
| (316) | N-(3,5-dichlorobenzenesulfonyl)-(L)-prolyl-(L)-O-(acetic acid)-tyrosine | 545.2 |
| (317) | N-(3,5-dichlorobenzenesulfonyl)-(L)-prolyl-(L)-2(S)-methyl-prolyl-(L)-O-(1-(2-propanonyl)-tyrosine | 557.3 |
| (318) | N-(3,5-dichlorobenzenesulfonyl)-(L)-prolyl-(L)-2(S)-methyl-prolyl-(L)-O-(1-pyrrolidinylcarbonyl)-tyrosine, methyl ester | 612.4 |
| (319) | N-(3,5-dichlorobenzenesulfonyl)-(L)-prolyl-(L)-2(S)-methyl-prolyl-(L)-O-(4-morpholinyl-carbonyl)-tyrosine | 614.2 |
| (320) | N-(3,5-dichlorobenzenesulfonyl)-(L)-prolyl-(L)-O-(2-pyrrolylcarbonyl)-tyrosine | 580.3 |
| (321) | N-(3,5-dichlorobenzenesulfonyl)-(L)-prolyl-(L)-2(S)-methyl-prolyl-(L)-O-(N-phenyl-N-methylaminocarbonyl)-tyrosine | 634.4 |
| (322) | N-(3,5-dichlorobenzenesulfonyl)-(L)-prolyl-(L)-2(S)-methyl-prolyl-(L)-O-(N,N-diethyl-aminocarbonyl)-tyrosine | 600.3 |

-continued

| Ex. | Compound Name | MS* |
|---|---|---|
| (323) | N-(3-chlorobenzenesulfonyl)-(L)-2(S)-methyl-prolyl-(L)-O-(4-morpholinyl-carbonyl)-tyrosine | 580.3 |
| (324) | N-(3,5-dichlorobenzenesulfonyl)-(L)-2(S)-methyl-prolyl-(L)-O-(N,N-diisopropyl-aminocarbonyl)-tyrosine | 628.6 |
| (325) | N-(3,5-dichlorobenzenesulfonyl)-(L)-prolyl-(L)-O-(benzoyl)-tyrosine | 591.3 |
| (326) | N-(3,5-dichlorobenzenesulfonyl)-(L)-prolyl-(L)-O-(cyclopentanoyl)-tyrosine | 583.3 |

*m/e: $(M + 1 (H^+))^+$ or $(M + 18 (NH_4^+))^+$

EXAMPLE 327
N-(3,5-Dichlorobenzenesulfonyl)-(L)-prolyl-(L)-O-(5-tetrazolyl)methyl-tyrosine Step A: N-(3.5-dichlorobenzenesulfonyl)-(L)-prolyl-(L)-O-cyanomethyl-tyrosine, tert-butyl ester To a solution of N-(3,5-dichlorobenzenesulfonyl)-(L)-prolyl-(L)-tyrosine, tert-butyl ester (200 mg, 0.368 mmole, obtained from Example 299, Step A) dissolved in 2.0 mL of dry dimethylformamide was added bromoacetonitrile (353.1 mg, 2.94 mmole) and anhydrous potassium carbonate (152.6 mg, 1.10 mmole). The reaction mixture was stirred vigorously under a dry nitrogen atmosphere at 40° C. overnight. The reaction mixture was then diluted with ethyl acetate and acidified with 5% aqueous citric acid to pH=5. After separation of the organic layers, the aqueous layer was washed with fresh ethyl acetate (3×). The combined organic layers were successively washed with water, saturated salt solution, and then dried over anhydrous magnesium sulfate. The residue obtained after filtration and removal of solvents was purified on a 1000 micron Chromatotron plate by gradient elution using 10-8-5-4-2-1:1 Hexane:EtoAc. This afforded 150.4 mg (70% yield) of the title compound as an off-white powder.

MS: (ESI) m/e 682.4 $(M+1)^+$.

$^1$H-NMR 400 MHz (CDCl$_3$) δ 1.44 (s, 9H), 1.56–1.69 (m, 3H), 2.08–2.11 (m, 1H), 3.00 (dd, J=14.0, 6.68 Hz, 1H), 3.05–3.13 (m, 1H), 3.21 (dd, J=14.0, 6.69 Hz, 1H), 3.35–3.51 (m, 1H), 4.09 (dd, J=8.5, 3.4 Hz, 1H), 4.68 (dd, J=13.8, 6.4 Hz, 1H), 4.73 (s, 2H), 6.89 (d, J=8.7 Hz, 2H), 7.09 (d, J=8.6 Hz, 2H), 7.15 (d, J=8.7 Hz, 2H), 7.58 (distorted m, 1H), 7.70–7.73 (distorted m, 2H).

Step B: N-(3.5-Dichlorobenzenesulfonyl)-(L)-prolyl-(L)-O-(5-tetrazolyl)methyl-tyrosine, tert-butyl ester A mixture of N-(3,5-dichlorobenzenesulfonyl)-(L)-prolyl-(L)-O-cyanomethyl-tyrosine, tert-butyl ester (82.0 mg, 0.141 mmol) and f trimethyltin azide (101.4 mg, 0.493 mmol) in 6 mL of dry toluene was stirred at reflux for 1 day. The reaction mixture was cooled to room temperature and concentrated in vacuo. The residue was treated with 6 mL of dry methanol and 3 g of silica gel and stirred vigorously overnight at room temperature. This slurry was concentrated to give a powder. This was vacuum-dried and then added as a slurry in methylene chloride to a 4.0×7.0 cm cartridge of Flash-40 silica gel and eluted with 10% methanol in methylene chloride. The fractions containing the desired product were combined and concentrated to yield 33.0 mg (38.2% yield) of the titled compound as a white powder.

Mass spectrum (ESI) m/e 630.1 $(M+18)^+$.

$^1$H-NMR400 MHz (CD$_3$OD) δ 1.41 (s, 9H), 1.61–1.92 (m, 5H), 2.08–2.11 (m, 1H), 2.97–3.01 (distorted m, 1H), 3.09 (dd, J=14.0, 6.2 Hz, 1H), 3.24–3.28 (m, 1H), 3.39–3.46 (m, 1H), 4.17–4.21 (m, 1H), 4.52 (dd, J=14.0, 5.9 Hz, 1H), 5.37 (s, 2H), 6.99 (d, J=8.7 Hz, 2H), 7.18 (d, J=8.7 Hz, 2H), 7.78–7.80 (distorted m, 3H), 8.15 (d, J=8.1 Hz, 1H).

Step C: N-(3.5-Dichlorobenzenesulfonyl)-(L)-prolyl-(L)-O-(5-tetrazolyl)methyl-tyrosine A mixture of N-(3,5-dichlorobenzenesulfonyl)-(L)-prolyl-(L)-O-(5-tetrazolyl)methyl-tyrosine, tert-butyl ester (30 mg, 0.0489 mmol) was dissolved in 2 mL of dry methylene chloride and was cooled in an ice bath. A solution of 1/1 v/v of trifluoroacetic acid (55.7 mg, 0.489 mmol) and methylene was added, which was stirred vigorously for three hr ice temperature. A stream of dry nitrogen was applied to remove the solvents and the residue was loaded onto a reverse phase prep-plate (RP-18wF$_{254}$s 0.2 mm 20×20 cm, EM Science) using a minimal amount of methylene chloride and eluted with 40:60 water/acetonitrile. The product band was collected and extracted with 10% methanol/methylene chloride, concentrated to provide 5.0 mg (18% yield) of the titled compound as a white foam material.

Mass spectrum (ESI) m/e 569.3 $(M+1)^+$.

$^1$H-NMR500 MHz (CD$_3$OD) δ 1.61–1.87 (m, 3H), 2.05 (distorted m, 1H), 3.02 (dd, J=14.0, 8.1 Hz, 1H), 3.18 (dd, J=14.1, 5.2 Hz, 1H),3.23–3.28 (m, 1H), 3.39–3.43 (m, 1H), 4.22 (t, J=6.0 Hz, 1H), 4.64 (dd, J=8.0, 5.3 Hz, 1H), 5.41 (s, 2H), 6.99 (distorted d, J=2.1 Hz, 2H), 7.22 (distorted d, J=1.8 Hz, 2H), 7.76–7.78 (m, 3H).

EXAMPLE 328
N-(3.5-Dichlorobenzenesulfonyl)-(L)-2(S)-methyl-prolyl-(L)-N'-benzyl-histidine Step A: N-t-Butyloxycarbonyl-(L)-2(S)-methyl-proline 2(S)-Methyl-proline (4.98 g, 38.55 mmol) was dissolved in dioxane (40 mL) and water (40 mL) to give a suspension. Triethyl amine (11.4 gm, 46.27 mmol) was added, followed by the addition of 2-(tert-butoxycarbonyloxyimino)-2-phenylacetonitrile (BOC-ON, 5.85 gm, 57.83 mmol). The reaction mixture was stirred at room temperature overnight to give a yellow solution. The reaction was quenched with water (160 mL) and diethyl ether (225 mL). The organic layers were separated and the ether layer extracted with water (80 mL). The combined aqueous layers were cooled to OC and treated with 2N hydrochloric acid to pH=2, and then extracted with ethyl acetate (3×150 mL). The combined organic layers were dried with over anhydrous sodium sulfate, filtered and concentrated to yield 7.24 g (82% yield) of the titled compound as a white solid (mp=119–125° C.).

Mass spectrum (ESI) m/e 230.1 $(M+1)^+$.

$^1$H-NMR 400 MHz (CD$_3$OD) δ 1.41 (s, 9H), 1.49 (s, 3H), 1.85–1.99 (m, 3H), 2.13–2.25 (m, 1H), 3.43–3.54 (m, 2H).

Step B: N-t-Butyloxycarbonyl-(L)-2(S)-methyl-prolyl-(L)-N-benzyl-histidine, methyl ester.

A mixture of N-t-butyloxycarbonyl-(L)-2(S)-methyl-proline (300 mg, 1.31 mmol) and of (L)-N$^ε$-benzyl-histidine, methyl ester dihydrochloride (339.28 mg, 1.31 mmol) in dry dimethylformamide (5 mL) and methylene chloride (2.5 mL) was stirred at room temperature. Diisopropylethyl amine (684.6 μL, 3.93 mmol) was added followed by the addition of benzotriazole-1-yl-oxy-tris-pyrrolidino-phosphosphate hexafluorophosphate (PyBOP, 681.6 mg, 1.31 mmol) and the mixture was stirred overnight. This reaction mixture was treated with 2N hydrochloric acid, water, and ethyl acetate. The layers were separated and the aqueous layer was extracted with ethyl acetate (3×). The combined organic layers were washed with saturated odium bicarbonate, water, saturated salt solution and dried over anhydrous magnesium sulfate. After filtration and removal of solvent by rotoevaporation, the residue was purified by flash chromatography on silica gel and eluted with 10-9-8-7-6-5-4-3-2-1:1 Hexane:ethyl acetate and finally with 1–2% methanol/methylene chloride. The fractions containing the desired material were combined and concentrated to yield 357.8 mg (58% yield) of the titled compound as a sticky white foam.

Mass spectrum (ESI) m/e 471.5 (M+1)⁺.

400 MHz (CD₃OD) δ 1.34 (s, 9H), 1.43 (distorted s, 3H), 1.62–2.05 (m, 4H), 2.98–3.11 (m, 2H), 3.38–3.42 (m, 1H), 3.47–3.55 (m, 1H), 3.66 (s, 3H), 4.66–4.70 (m, 1H), 5.16 (distorted s, 2H), 6.95 (s, 1H), 7.26–7.38 (m, 5H), 7.86 (s, 1H), 8.09 (s, 1H).

Step C: (L)-2(S)-Methyl-prolyl-(L)-N'-benzyl-histidine, methyl ester, dihydrochloride.

A mixture of N-t-butyloxycarbonyl-(L)-2(S)-methyl-prolyl-(L)-N-benzyl-histidine, methyl ester (272.5 mg, 0.649 mmol) and hydrochloric acid(g)/ethyl acetate (14.0 mL, 58.4 mmol) in dry ethyl acetate (2 mL) was stirred at room temperature for one hour. Methylene chloride was added and solvents were removed by rotoevaporation. The residue was dried under high vacuum overnight and gave 235.1 mg (97.6% yield) of the titled compound. Mass spectrum (CI) m/e 371.3 (M+1)⁺.

¹H-NMR 400 MHz (CD₃OD) δ 1.43 (s, 3H), 1.87–1.93 (m, 1H), 2.01–2.13 (m, 2H), 2.32–2.37 (m, 1H), 3.14–3.21 (m, 1H), 3.29–3.38 (m, 4H), 3.71 (s, 3H), 4.77 (dd, J=10.1, 5.3 Hz, 1H), 5.39 (s, 2H), 7.40–7.43 (m, 5H), 9.05 (distorted s, 1H).

Step D: N-(3.5-Dichlorobenzenesulfonyl)-(L)-2(S)-methyl-prolyl-(L)-N'-benzyl-histidine, methyl ester.

(L)-2(S)-methyl-prolyl-(L)-N-benzyl-histidine, methyl ester, dihydrochloride (191.3 mg, 0.516 mmol was dissolved in dry tetrahydrofuran (5 mL) and dry dimethylformamide (2.5 mL). Diisopropylethyl amine (269.8 μL, 1.55 mmol) and 4,4'-dimethylaminopyridine were added to this solution. After cooling to 5° C. for 5 minutes, a solution of 3,5-dichlorobenzenesulfonyl chloride (190.2 mg, 0.774 mmol) in dry tetrahydrofuran (2.5 mL) was added to the reaction mixture which was allowed to reach room temperature overnight. This reaction mixture was treated with water and ethyl acetate. The aqueous layer was extracted with ethyl acetate (3×). The organic layers were combined and successively washed with water and saturated salt solution and dried with anhydrous magnesium sulfate. After filtration, the solvents were removed by rotoevaporation. The residue was purified on a 4.0×7.0 cm cartridge of Flash-40 silica gel and eluted 1–2–3–4–5% methanol/methylene chloride to yield 116.6 mg (39% yield) of the titled compound.

Mass spectrum (CI) m/e 579.1 (M+1)⁺.

¹H-NMR 400 MHz (CDCl₃) δ 1.67 (s, 3H), 1.72–1.86 (m, 2H), 1.91–1.98 (m, 1H), 2.30–2.35 (m, 1H), 3.12 (dd, J=15.0, 4.76 Hz, 1H), 3.18 (dd, J=14.6, 6.02 Hz, 1H), 3.33–3.39 (m, 1H), 3.66 (s, 3H), 4.77 (dd, J=6.11, 1.27 Hz, 1H), 5.04 (s, 2H), 6.76 (s, 1H), 7.12–7.15 (m, 2H), 7.29–7.35 (m, 3H), 7.72 (distorted d, J=1.99 Hz, 2H), 7.99 (distorted s, 2H).

Step E: N-(3.5-Dichlorobenzenesulfonyl)-(L)-2(S)-methyl-prolyl-(L)-N'-benzyl-histidine.

A mixture of N-(3,5-dichlorobenzenesulfonyl)-(L)-2(S)-methyl-prolyl-(L)-N-benzyl-histidine, methyl ester (115.5 mg, 0.199 mmol) in 0.2N sodium hydroxide in ethanol (1.2 mL) was stirred at room temperature for 4 hours. The reaction mixture was treated with ethyl acetate and 5% citric acid to pH=3–4. The aqueous layer was extracted with ethyl acetate (3×). The combined organic layers were washed with saturated salt solution and dried over anhydrous magnesium sulfate. The solution was filtered and the solvents were removed removed by rotoevaporation. The residue was purified on a 4.0×7.0 cm cartridge of Flash-40 silica gel eluted with 15% methanol/methylene chloride to yield 51.2 mg (45.5% yield) of the titled compound as a light brown foam.

Mass spectrum (ESI) m/e 565.4 (M+1)⁺.

¹H-NMR 400 MHz (CDCD₃) δ 1.28 (s, 3H), 1.75–1.84 (m, 3H), 2.10–2.14 (m, 1H), 3.06–3.12 (m, 1H), 3.24–3.29 (m, 2H), 3.31–3.42 (m, 2H), 4.46–4.49 (m, 1H), 5.23 (s, 2H), 7.18 (s, 1H), 7.30–7.37 (m, 5H), 7.74–7.79 (m, 3H), 8.34 (broad s, 1H).

EXAMPLE 329

N-Benzenesulfonyl-(L)-prolyl-2-amino-2-norbornanecarboxylic acid

Step A: 2-Amino-2-norbornanecarboxylic acid, methyl ester hydrochloride.

To 25 mL of methanol at 0° C. was added thionyl chloride (2.4 mL, 32 mmol). After stirring at 0° C. for 5 min, 2-amino-2-norbornanecarboxylic acid (1.0 g, 6.4 mmol) was added in one portion, and the mixture was heated at reflux for 16 h. The mixture was concentrated to give the product (1.2 g, 92%) as a white solid.

Step B: N-Benzenesulfonyl-(L)-prolyl-2-amino-2-norbornanecarboxylic acid, methyl ester To a solution of 2-amino-2-norbornanecarboxylate, methyl ester hydrochloride (400 mg, 2.0 mmol), N-benzenesulfonyl-(L)-proline (510 mg, 2.0 mmol), 1-(3-dimethylaminopropyl)-3-ethylcarbodiimide hydrochloride (306 mg, 2.0 mmol), 1-hydroxybenzotriazole (202 mg, 2.0 mmol) in 4 mL of tetrahydrofuran at 0° C. was added N-methyl morpholine (0.22 mL, 2.0 mmol). After 15 min at 0° C., the reaction mixture was stirred at room temperature for 16 h, and was concentrated in vacuo. The residue was purified by flash column chromatography on silica gel eluted with 10:1 methylene chloride/ethyl acetate to give the title compound (478 mg, 59%) as a mixture of diastereomers.

MS: calculated for $C_{20}H_{26}N_2O_5S$ 406; found m/e 417 (M+H⁺), 423 (M+NH₄⁺).

Step C: N— Benzenesulfonyl-(L)-prolyl-2-amino-2-norbornanecarboxylic acid

A solution of N-phenylsulfonyl-(L)-prolyl-2-amino-2-norbornanecarboxylic acid, methyl ester (210 mg, 0.2 mmol) in 3 mL of 1:1 aqueous sodium hydroxide (1 M) and methanol was stirred at room temperature for 2 weeks. The reaction was quenched with concentrated hydrochloric acid (0.2 mL), and the resulting mixture was partitioned between saturated salt solution and ethyl acetate. The product was extracted with ethyl acetate and was purified by flash chromatography on silica gel eluted with 100:5:1 methylene chloride/methanol/acetic acid to give the product as a mixture of diastereomers.

MS: calculated for $C_{19}H_{24}N_2O_5S$, 392; found m/e 393 (M+H⁺), 410 (M+NH₄⁺)

EXAMPLE 330

N-Benzenesulfonyl-(L)-prolyl-3(R)-methyl-phenylalanine

Step A: N-Benzenesulfonyl-(L)-prolyl-3(R)-methyl-phenylalanine, methyl ester.

The title compound was prepared by the procedure described in Example 289 Steps A—C starting from (L)-3 (R)-methyl-phenylalanine (prepared by the procedure of Hruby and coworkers: Tetrahedron, 1992, 48, 4733).

Step B: N-Benzenesulfonyl-(L)-prolyl-3(R)-methyl-phenylalanine,

A solution of N-phenylsulfonyl-(L)-prolyl-(L)-3(R)-methyl-phenylalanine, methyl ester (23 mg, 0.053 mmol) in 1.0 mL of 1:1 tetrahydrofuran/water at 0° C. was added lithium hydroxide hydrate (12 mg, 0.033 mmol) and hydrogen peroxide (30%, 33 mL, 0.033 mmol). The reaction was allowed to warm up to 18° C. over 2 hr. The reaction was quenched with dilute sodium thiosulfate and 1 M hydrochloric acid, and the resulting mixture was partitioned between saturated salt solution and ethyl acetate. The product was extracted with ethyl acetate and purified by flash column chromatography on silica gel eluted with 50:50:1 ethyl acetate/hexane/acetic acid to 20:1 ethyl acetate/acetic acid to give the product (17 mg, 77%).

MS: calculated for $C_{21}H_{24}N_2O_5S$, 416; found m/e 417 $(M+H^+)$, 434 $(M+NH_4^+)$ $^1$H-NMR (500 Mhz, $CD_3OD$) δ 8.2–7.2 (10H, m), 4.65 (1H, d), 4.23 (1H, dd), 3.48–3.36 (2H, m), 3.23 (1H, m), 2.0–1.2 (4H, m), 1.38 (3H, d)

EXAMPLE 331

N-Phenylsulfonyl-(L)-prolyl-(L)-2.3-methano-phenylalanine and N-Phenylsulfonyl-(L)-prolyl-(D)-2.3-methano-phenylalanine.

Step A: N-Phenylsulfonyl-(L)-prolyl-(L)-2.3-methano-phenylalanine, methyl ester and N-Phenylsulfonyl-(L)-prolyl-(D)-2.3-methano-phenylalanine, methyl ester.

The title compounds were prepared by the procedure described in Example 289, Steps A–C starting from E-2,3-methanophenylalanine, methyl ester hydrochloride (prepared by the procedure of Stammers and coworkers: J. Org. Chem., 1982, 47, 3270). Under the described conditions, reaction of diazomethane with Z-2-phenyl-4-benzylidene-5-oxazolinone (Aldrich) gave a 4:1 mixture of Z-1,5-diphenyl-6-oxa-4-azaspiro(2,4)hept-4-ene-7-one and E-1,5-diphenyl-6-oxa-4-azaspiro(2,4)hept-4-ene-7-one, and the minor diastereomer was carried on to E-2,3-methanophenylalanine methyl ester hydrogen chloride salt as described. Subsequent peptide coupling (51 mg scale) afforded a 1:1 mixture of diastereomers, which were partially separated on silica gel eluting with 4:4:1 methylene chloride/hexane/ethyl acetate.

Top isomer: $^1$H-NMR (500 Mhz, $CD_3OD$) δ 8.0–7.1 (10H, m), 4.18 (1H, dd), 3.60 (1H, ddd), 3.30 (3H, S), 3.4–3.2 (1H, m), 2.96 (1H, dd), 2.18 (1H, dd), 2.1–1.8 (3H, m), 1.7–1.6 (1H, m), 1.58 (1H, dd)

Bottom isomer: $^1$H-NMR (500 Mhz, $CD_3OD$) δ 8.0–7.2 (10H, m), 4.24 (1H, dd), 3.66 (1H, ddd), 3.30 (3H, S), 3.26 (1H, ddd), 2.88 (1H, dd), 2.22 (1H, dd), 2.1–1.8 (3H, m), 1.66–1.60 (1H, m), 1.53 (1H, dd)

Step B: N-Phenylsulfonyl-(L)-prolyl-(L)-2.3-methano-phenylalanine and N-phenylsulfonyl-(L)-prolyl-(D)-2,3-methano-phenylalanine.

To a solution of the top isomer of N-phenylsulfonyl-(L)-prolyl-2,3-methanophenylalanine, methyl ester (15 mg, 0.035 mmol) in 0.6 mL of 1:1 tetrahydrofuran/water was added lithium hydroxide hydrate (15 mg, 0.35 mmol), and the mixture was stirred at room temperature for 15 hr. The reaction was quenched with concentrated hydrochloric acid (0.2 mL), and the resulting mixture was partitioned between brine and ethyl acetate. The product was extracted with ethyl acetate and was purified by flash chromatography on silica gel eluted with 100:5:1 methylene chloride/methanol/acetic acid to give the product in quantitative yield.

MS: calculated for $C_{21}H_{22}N_2O_5S$, 414; found m/e 415.3 $(M+H^+)$, 432.3 $(M+NH_4^+)$ $^1$H-NMR (500 Mhz, $CD_3OD$) δ 8.0–7.0 (10H, m), 4.10 (1H, dd), 3.60 (1H, ddd), 3.27 (1H, ddd), 2.84 (1H, dd), 2.18 (1H, dd), 2.1–1.8 (3H, m), 1.66–1.56 (1H, m), 1.57 (1H, dd).

The bottom isomer was hydrolyzed in the same fashion as described for the top isomer:

MS: calculated for $C_{21}H_{22}N_2O_5S$, 414; found m/e 415.2 $(M+H^+)$, 432.2 $(M+NH_4^+)$ $^1$H-NMR (500 Mhz, $CD_3OD$) δ 8.0–7.1 (10H, m), 4.06 (1H, dd), 3.66 (1H, ddd), 3.27 (1H, ddd), 2.86 (1H, dd), 2.19 (1H, dd), 2.1–1.8 (3H, m), 1.68–1.58 (1H, m), 1.52 (1H, dd).

EXAMPLE 332

N-(3.5-Dichlorobenzenesulfonyl-(L-2(S)-methyl-prolyl-(L)-4-(5-((1H,3H)-1.3-dimethylpyrimidine-2,4-dione))-phenylalanine Step A: N-(3-Fluorobenzenesulfonyl)-(L)-prolyl-(L)-4-trimethylstannylalanine, tert-butyl ester, A solution of N-(3-fluorobenzenesulfonyl)-(L)-prolyl-(L)-4-iodophenylalanine, tert-butyl ester (1.0 gm, 1.53 mmol), hexamethylditin (411 μL, 2.14 mmol), triphenylphosphine (8 mg, 0.03 mmol), lithium chloride (71 mg, 1.68 mmol), and tetrakis(triphenylphosphine)palladium(0) (88 mg, 0.077 mmol) in 1,4-dioxane (10 mL) was heated to 95° C. under a dry nitrogen atmosphere for 1.5 hr. The solution was cooled and diluted with ethyl acetate (100 mL) and successively washed with 1N sodium hydroxide solution (2×) and saturated salt solution (1×). After drying over anhydrous magnesium sulfate, the solution was filtered and the solvent removed by rotoevaporation. The residue was purified by silica gel column chromatography eluted with 10% acetone in hexanes to yield N-(3-fluorobenzenesulfonyl)-(L)-prolyl-(L)-4-(trimethylstannyl) phenylalanine, tert-butyl ester (577 mg, 54% yield).

MS: m/e 658 (M+18; $NH_4^+$).

N-(3,5-Dichlorobenzenesulfonyl)-(L)-2(S)-methyl-prolyl-(L)-4-trimethylstannyl)phenylalanine, tert-butyl ester was prepared from N-(3,5-dichlorobenzenesulfonyl)-(L)-2(S)-methyl-prolyl-(L)-4-iodophenylalanine, tert-butyl ester by an analogous procedure.

Step B: N-(3,5-Dichlorobenzenesulfonyl)-(L)-2(S)-methyl-prolyl-(L)-4-(5-((1H,3H)-1,3-dimethylpyrimidine-2.4-dione))-phenylalanine. tert butyl ester A solution of N-(3,5-dichlorobenzenesulfonyl)-(L)-2(S)-methyl-prolyl-(L)-4-trimethylstannylphenylalanine, tert-butyl ester (70 mg, 0.1 mmol), (1H,3H)-1,3-dimethyl-5-iodo-pyrimidine-2,4-dione (40 mg, 0.15 mmol) and tetrakis-triphenylphosphine palladium (4 mg, 0.003 mmol) in dry dimethylformamide (1 mL) was heated in an oil bath at 100° C. for 1 hr under a dry nitrogen atmosphere. After cooling, the solvent was removed by rotoevaporation under high vacuum. The residue was purified by flash column chromatography on silica gel eluted with 15% acetone in hexanes to give the title compound as a light yellow solid (27 mg, 40% yield).

MS: (m/e) 696 (M+18 ($NH_4^+$)).

Step C: N-(3,5-Dichlorobenzenesulfonyl)-(L)-2(S)-methyl-prolyl-(L)-4-(5-((1H,3H)-1,3-dimethylpyrimidine-2,4-dione))phenylalanine The tert-butyl ester of N-(3,5-dichlorobenzenesulfonyl)-(L)-2(S)-methyl-prolyl-(L)-4-(5-((1H,3H)-1,3-dimethylpyrimidine-2,4-dione))-phenylalanine, tert butyl ester (24 mg, 0.035 mmol) was stirred in a solution of trifluoroacetic acid (170 μL, 2.2 mmol) in methylene chloride (1.0 mL) according to the procedure described in Example 225, Step E to yield the title compound.

MS: (m/e) 640 (M+18 ($NH_4^+$)).

EXAMPLE 333

Inhibition of VLA-4 Dependent Adhesion to BSA-CS-1 Conjugate

Step A. Preparation of CS-1 Coated Plates.

Untreated 96 well polystyrene flat bottom plates were coated with bovine serum albumin (BSA; 20 μg/ml) for 2 hours at room temperature and washed twice with phosphate buffered saline (PBS). The albumin coating was next derivatized with 10 μg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 μg/ml and allowed to react for 2 hours at room temperature. The plates were washed twice with PBS and stored at 4° C.

Step B. Preparation of Fluorescently Labeled Jurkat Cells.

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 µg/ml streptomycin and 2 mM glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of $2 \times 10^6$ cells/ml in PBS containing a 1 µM concentration of a fluorogenic esterase substrate (2',7'-bis-(2-carboxyethyl)-5-(and -6)-carboxyfluorescein, acetoxymethyl ester; BCECF-AM; Molecular Probes Inc., Eugene, Oreg.; catalog #B-1150) for 30–60 minutes at 37° C. in a 5% $CO_2$/air incubator. The fluorescently labeled Jurkat cells were washed two times in PBS and resuspended in RPMI containing 0.25% BSA at a final concentration of $2.0 \times 10^6$ cells/ml.

Step C. Assay Procedure.

Compounds of this invention were prepared in DMSO at 100× the desired final assay concentration. Final concentrations were selected from a range between 0.001 nM-100 µM. Three µL of diluted compound, or vehicle alone, were premixed with 300 µL of cell suspension in 96-well polystyrene plates with round bottom wells. 100 µL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 334

Antagonism of VLA-4 Dependent Binding to VCAM-Ig Fusion Protein.

Step A. Preparation of VCAM-Ig.

The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAATTCTTTTACAGCCTGCC-3';
5'-PCR primer:
5'-ATAGGAATTCCAGCTGCCACCATGCCTGGGAAGATGG The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1: MPGKMVVILGASNILWIM-FAASQAFKIETTPESRYLAQIGDSVSLTC STTGCESPFFSWRTQIDSPLNGKVT-NEGTTSTLTMNPVSFGNEHSYLC TATCESRKLE-KGIQVEIYSFPKDPEIHLSGPLEAGKPITVKCSVADVY PFDRLEIDLLKGDHLMKSQE-FLEDADRKSLETKSLEVTFTPVIEDIGKV LVCRAKL-HIDEMDSVPTVRQAVKEL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 µg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B. Preparation of $^{125}$I-VCAM-Ig.

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C. VCAM-Ig Binding Assay.

Compounds of this invention were prepared in DMSO at 100× the desired final assay concentration. Final concentrations were selected from a range between 0.001 nM-100 µM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., MA) by making the following additions to duplicate wells: (i) 200 µL of binding buffer containing 1 mM $MnCl_2$; (ii) 20 µL of $^{125}$I-VCAM-Ig in binding buffer containing 1 mM $MnCl_2$ (final assay concentration ~100 pM); (iii) 2.5 µL of compound solution or DMSO; (iv) and $0.5 \times 10^6$ cells in a volume of 30 µL. The plates were incubated at room temperature for 30 minutes, filtered on a vacuum box, and washed on the same apparatus by the addition of 100 µL of binding buffer containing 1 mM $MnCl_2$. After insertion of the multiscreen plates into adapter plates (Packard, Meriden, Conn., cat# 6005178), 100 µL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-1 g binding corresponding to 0% inhibition. Control wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 335

Antagonism of $\alpha_4\beta_7$ Dependent Binding to VCAM-Ig Fusion Protein.

Step A. $\alpha_4\beta_7$ Cell line.

RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 U penicillin/100 µg streptomycin/2 mM L-glutamine at 37° C., 5% carbon dioxide. The cells were pelleted at 1000 rpm for 5 minutes and then washed twice and resuspended in binding buffer (25 mM Hepes, 150 mM NaCl, 0.1% BSA, 3 mM KCl, 2 mM Glucose, pH 7.4).

Step B. VCAM-IG Binding Assay.

Compounds of this invention were prepared in DMSO at 100× the desired final assay concentration. Final concentrations were selected from a range between 0.001 nM-100 µM. Compounds were assayed in Millipore MHVB multiscreen plates (Cat# MHVBN4550) by making the following sequential additions to duplicate wells: (i) 100 µl/well of binding buffer containing 1.5 mM $MnCl_2$; (ii) 10 µl/well $^{125}$I-VCAM-Ig in binding buffer (final assay concentration<500 pM); (iii) 1.5 µl/well test compound or DMSO alone; (iv) 38 µl/well RPMI-8866 cell suspension ($1.25 \times 10^6$ cells/well). The plates were incubated at room temperature for 45 minutes on a plate shaker at 200 rpm, filtered on a vacuum box, and washed on the same apparatus by the addition of 100 µL of binding buffer containing 1 mM $MnCl_2$. After insertion of the multiscreen plates into adapter plates (Packard, Meriden, Conn., cat# 6005178), 100 µL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the $IC_{6-0}$ was determined from a ten point titration using a validated four parameter fit algorithm.

What is claimed is:

1. A compound having the formula Ia:

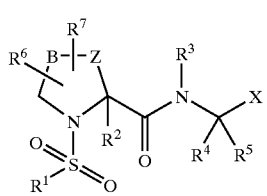

Ia or a pharmaceutically acceptable salt thereof, wherein $R^1$ is (1) heteroaryl selected from benzothiadiazolyl, thienyl, imidazolyl, pyridyl and pyrazolyl optionally substituted with one to four substituents independently selected from $R^b$; or (2) phenyl substituted at the 3-position optionally having a second substituent, wherein said substituents are independently selected from $R^b$, and provided that said second substituent is other than $CH=CHC(O)OR^f$;

$R^2$ is
1) hydrogen,
2) $C_{1-10}$alkyl,
3) $C_{2-10}$alkenyl,
4) $C_{2-10}$alkynyl,
5) aryl,
6) aryl-$C_{1-10}$alkyl,
7) heteroaryl,
8) heteroaryl-$C_{1-10}$alkyl, wherein alkyl, alkenyl, and alkynyl are optionally substituted with one to four substituents independently selected from $R^a$; and aryl and heteroaryl optionally substituted with one to four substituents independently selected from $R^b$;

$R^3$ is
1) hydrogen,
2) $C_{1-10}$alkyl,
3) Cy, or
4) Cy-$C_{1-10}$ alkyl, wherein alkyl is optionally substituted with one to four substituents independently selected from $R^a$; and Cy is optionally substituted with one to four substituents independently selected from $R^b$;

$R^4$ is
1) hydrogen,
2) $C_{1-10}$alkyl,
3) $C_{2-10}$alkenyl,
4) $C_{2-10}$alkynyl,
5) Cy,
6) Cy-$C_{1-10}$alkyl,
7) Cy-$C_{2-10}$alkenyl,
8) Cy-$C_{2-10}$alkynyl, wherein alkyl, alkenyl and alkynyl are optionally substituted with one to four substituents selected from phenyl and $R^x$, and Cy is optionally substituted with one to four substituents independently selected from $R^y$; or $R^3$, $R^4$ and the atoms to which they are attached together form a mono- or bicyclic ring containing 0–2 additional heteroatoms selected from N, O and S;

$R^5$ is
1) hydrogen,
2) $C_{1-10}$alkyl,
3) $C_{2-10}$alkenyl,
4) $C_{2-10}$alkynyl,
5) aryl,
6) aryl-$C_{1-10}$alkyl,
7) heteroaryl,
8) heteroaryl-$C_{1-10}$alkyl, wherein alkyl, alkenyl and alkynyl are optionally substituted with one to four substituents selected from $R^x$, and aryl and heteroaryl are optionally substituted with one to four substituents independently selected from $R^y$; or $R^4$, $R^5$ and the carbon to which they are attached form a 3–7 membered mono- or bicyclic ring containing 0–2 heteroatoms selected from N, O and S;

$R^6$ and $R^7$ are each independently selected from the group consisting of
1) a group selected from $R^d$, and
2) a group selected from $R^x$; or $R^6$, $R^7$ and the atom to which both are attached, or $R^6$, $R^7$ and the two adjacent atoms to which they are attached, together form a 5–7 membered saturated or unsaturated monocyclic ring containing zero to three heteroatoms selected from N, O or S, $R^a$ is
1) Cy, or
2) a group selected from Rx;
wherein Cy is optionally subsituted with one to four substituents independently selected from $R^c$;

$R^b$ is
1) a group selected from $R^a$,
2) $C_{1-10}$ alkyl,
3) $C_{2-10}$ alkenyl,
4) $C_{2-10}$ alkynyl,
5) aryl $C_{1-10}$alkyl,
6) heteroaryl $C_{1-10}$ alkyl,
wherein alkyl, alkenyl, alkynyl, aryl, heteroaryl are optionally substituted with a group independently selected from $R^c$;

$R^c$ is
1) halogen,
2) $NO_2$,
3) $C(O)OR^f$,
4) $C_{1-4}$alkyl,
5) $C_{1-4}$alkoxy,
6) aryl,
7) aryl $C_{1-4}$alkyl,
8) aryloxy,
9) heteroaryl,
10) NRfRg,
11) NRfC(O)Rg,
12) NRfC(O)NRfRg, or
13) CN;

$R^d$ and $R^e$ are independently selected from hydrogen, $C_{1-10}$alkyl, $C_{2-10}$ alkenyl, $C_{2-10}$alkynyl, Cy and Cy $C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy-$C_{1-10}$alkyl wherein Cy is optionally substituted with $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^i$
1) $C_{1-10}$alkyl,
2) $C_{2-10}$alkenyl,
3) $C_{2-10}$alkynyl, or
4) aryl;
wherein alkyl, alkenyl, alkynyl and aryl are each optionally substituted with one to four substituents independently selected from $R^c$;

$R^x$ is
1) —$OR^d$,
2) —$NO_2$,
3) halogen
4) —$S(O)_mR^d$,
5) —$SR^d$,
6) —$S(O)_2OR^d$,
7) —$S(O)_mNR^dR^e$,
8) —$NR^dR^e$,
9) —$O(CR^fR^g)_nNR^dR^e$,
10) —$C(O)R^d$,
11) —$CO_2R^d$,
12) —$CO_2(CR^fR^g)_bCONR^dR^e$,
13) —$OC(O)R^d$,
14) —CN,
15) —$C(O)NR^dR^e$,
16) —$NR^dC(O)R^e$,
17) —$OC(O)NR^dR^e$,
18) —$NR^dC(O)OR^e$,
19) —$NR^dC(O)NR^dR^e$,
20) —$CR^d(N$—$OR^e)$,
21) —$CF_3$,
22) oxo,
23) $NR^dC(O)NR^d SO_2R^i$,
24) $NR^dS(O)_mR^e$,
25) —$OS(O)_2OR^d$, or
26) —$OP(O)(OR^d)_2$;

$R^y$ is
1) a group selected from $R^x$,
2) $C_{1-10}$ alkyl,
3) $C_{2-10}$ alkenyl,
4) $C_{2-10}$ alkynyl,
5) aryl $C_{1-10}$alkyl,
6) heteroaryl $C_{1-10}$ alkyl,
7) cycloalkyl,
8) heterocyclyl;

wherein alkyl, alkenyl, alkynyl and aryl are each optionally substituted with one to four substituents independently selected from $R^x$;

Cy is cycloalkyl, heterocyclyl, aryl, or heteroaryl;

m is an integer from 1 to 2;

n is an integer from 1 to 10;

X is —$C(O)OR^d$;

Z is selected from —C— and —C—C—;

B is selected from the group consisting of
1) a bond,
2) —C-
3) —C—C—,
3) —C=C—,
4) a heteroatom selected from the group consisting of nitrogen, oxygen, and sulfur; and
5) —$S(O)_m$—;

with the proviso that $R^6/R^7$ is not oxo when attached to the carbon between N and B.

2. A compound of claim 1 wherein Z is C.

3. A compound of claim 1 wherein B is C, C=C, C—C or S.

4. A compound of claim 1 wherein X is $C(O)OR^d$.

5. A compound of claim 1 wherein $R^5$ is H and $R^4$ is $C_{1-10}$ alkyl or Cy-$C_{1-10}$alkyl, wherein alkyl is optionally substituted with one to four substituents selected from phenyl and RX, and Cy is optionally substituted with one to four substituents independently selected from RY; or $R^4$, $R^5$ and the carbon to which they are attached together form a 3–7 membered mono- or bicyclic carbon only ring.

6. A compound of claim 5, wherein $R^4$ is phenyl-$C_{1-3}$ alkyl, wherein phenyl is optionally substituted with one or two groups selected from RY.

7. A compound of claim 1, having the formula Ib:

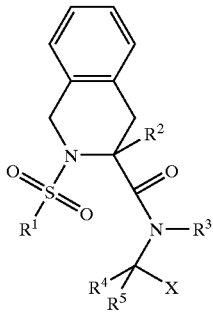

Ib wherein $R^2$ is H or $C_{1-6}$ alkyl, and $R^1$, $R^2$, $R^3$, $R^4$ and $R^5$ and X are as defined in claim 1.

8. A compound of claim 7, wherein X is $CO_2H$; $R^1$ is phenyl substituted at the 3-position optionally having a second substituent, wherein said substituents are independently selected from $R^b$; $R^2$ is H; $R^3$ is H or $C_{1-3}$ alkyl; $R^4$ is phenyl-$C_{1-3}$alkyl, wherein phenyl is optionally substituted with one or two groups selected from RY; and $R^5$ is H.

9. A compound of claim 1, having the formula Ic:

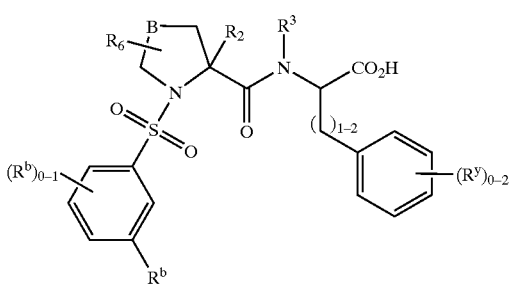

Ic wherein $R^2$ is H or $C_{1-3}$ alkyl; $R^6$ is H, $C_{1-6}$ alkyl, aryl, $OR^d$, $SR^d$, $NR^dR^e$, or $NR^dC(O)R^e$; B is S, C=C, C or C—C; $R^3$ is H or $C_{1-6}$alkyl, Rb and RY are as defined in claim 1.

10. A compound of claim 9 wherein B is C and Rb is halogen, $C_{1-10}$alkoxy, cyano, or trifluoromethyl.

11. A compound of claim 1 selected from the group consisting of:

N-(3,4-dimethoxybenzenesulfonyl)-1,2,3,4-tetrahydroisoquinoline-3(S)-carbonyl-(L)-leucine;
N-(3,4-dimethoxybenzenesulfonyl)-1,2,3,4-tetrahydroisoquinoline-3(S)-carbonyl-(L)-arginine;
N-(3,4-dimethoxybenzenesulfonyl)-1,2,3,4-tetrahydroisoquinoline-3(S)-carbonyl-(L)-glutamic acid;
N-(3,4-dimethoxybenzenesulfonyl)-1,2,3,4-tetrahydroisoquinoline-3(S)-carbonyl-glycine;
N-(3,4-dimethoxybenzenesulfonyl)-1,2,3,4-tetrahydroisoquinoline-3(S)-carbonyl-(L)-(1-naphthyl)alanine;
N-(3,4-dimethoxybenzenesulfonyl)-1,2,3,4-tetrahydroisoquinoline-3(S)-carbonyl-(L)-α-t-butylglycine;
N-(3,4-dimethoxybenzenesulfonyl) 1,2,3,4-tetrahydroisoquinoline-3(S)-carbonyl-(L)-3-(2-thienyl)alanine;
N-(3,4-dimethoxybenzenesulfonyl)-1,2,3,4-tetrahydroisoquinoline-3(S)-carbonyl-(L)-cyclohexylalanine;
N-(3,4-dimethoxybenzenesulfonyl)-1,2,3,4-tetrahydroisoquinoline-3(S)-carbonyl-(L)-3-(2-naphthyl)alanine;
N-(3,4-dimethoxybenzenesulfonyl)-1,2,3,4-tetrahydroisoquinoline-3(S)-carbonyl-(L)-3,3-diphenylalanine;
N-(3,4-dimethoxybenzenesulfonyl)-1,2,3,4-tetrahydroisoquinoline-3(S)-carbonyl-1,2,3,4-tetrahydroisoquinoline-3-carboxylic acid;
N-(3,4-dimethoxybenzenesulfonyl)-1,2,3,4-tetrahydroisoquinoline-3(S)-carbonyl-(L)-proline;
N-(3,4-dimethylbenzenesulfonyl)-1,2,3,4-tetrahydroisoquinoline-3(S)-carbonyl-(L)-cysteine;
N-(2,5-dichlorobenzenesulfonyl)-1,2,3,4-tetrahydroisoquinoline-3(S)-carbonyl-(L)-norleucine;
N-(3,4-dimethoxybenzenesulfonyl)-1,2,3,4-tetrahydroisoquinoline-3(S)-carbonyl-(L)-phenylalanine;
N-(3,4-dimethoxybenzenesulfonyl)-1,2,3,4-tetrahydroisoquinoline-3(S)-carbonyl-(L)-glutamine;
N-(3,4-dimethoxybenzenesulfonyl)-1,2,3,4-tetrahydroisoquinoline-3(S)-carbonyl-(L)-(4-nitrophenyl)alanine;
N-(3,4-dimethoxybenzenesulfonyl)-1,2,3,4-tetrahydroisoquinoline-3(S)-carbonyl-(L)-asparagine;
N-(3,4-dimethoxybenzenesulfonyl)-1,2,3,4-tetrahydroisoquinoline-3(S)-carbonyl-(L)-methionine;
N-(3,4-dimethoxybenzenesulfonyl)-1,2,3,4-tetrahydroisoquinoline-3(S)-carbonyl-(L)-homophenylalanine;
N-(3,4-dimethoxybenzenesulfonyl)-1,2,3,4-tetrahydroisoquinoline-3(S)-carbonyl-(D)-norleucine;
N-(3,4-dimethoxybenzenesulfonyl)-1,2,3,4-tetrahydroisoquinoline-3(S)-carbonyl-(L)-(4-fluorophenyl)alanine;
N-(3-toluenesulfonyl)-1,2,3,4-tetrahydroisoquinoline-3(S)-carbonyl-(L)-norleucine;
N-(4-chloro-3-nitrobenzenesulfonyl)-1,2,3,4-tetrahydroisoquinoline-3(S)-carbonyl-(L)-norleucine;
N-(3,5-dichlorobenzenesulfonyl) 1,2,3,4-tetrahydroisoquinoline-3 (S)-carbonyl-(L)-norleucine;
N-(3,4-dichlorobenzenesulfonyl) 1,2,3,4-tetrahydroisoquinoline-3(S)-carbony(L)-norleucine;
N-(2,3-dichlorobenzenesulfonyl)-1,2,3,4-tetrahydroisoquinoline-3(S)-carbonyl-(L)-norleucine;
N-(2,5-dimethoxybenzenesulfonyl)-1,2,3,4-tetrahydroisoquinoline-3(S)-carbonyl-(L)-norleucine;
N-(3,4-dimethoxybenzenesulfonyl)-1,2,3,4-tetrahydroisoquinoline-3(S)-carbonyl-(L)-serine;
N-(3,4-dimethoxybenzenesulfonyl)-1,2,3,4-tetrahydroisoquinoline-3(S)-carbonyl-(L)-isoleucine;
N-(3,4-dimethoxybenzenesulfonyl)-1,2,3,4-tetrahydroisoquinoline-3(S)-carbonyl-(L)-tryptophan;
N-(2,1,3-benzothiadiazole-4-sulfonyl)-1,2,3,4-tetrahydroisoquinoline-3(S)-carbonyl-(L)-tryptophan;
N-(3,4-dimethoxybenzenesulfonyl)-1,2,3,4-tetrahydroisoquinoline-3(S)-carbonyl-(L)-3-(3-pyridyl)alanine;
N-(3,4-dimethoxybenzenesulfonyl)-1,2,3,4-tetrahydroisoquinoline-3(S)-carbonyl-(L)-3-(2-naphthyl)alanine, ethyl ester;
N-(3,4-dimethoxybenzenesulfonyl)-1,2,3,4-tetrahydroisoquinoline-3(R)-carbonyl-(D)-norleucine;
N-(3-nitrobenzenesulfonyl)-1,2,3,4-tetrahydroisoquinoline-3(S)-carbonyl-(L)-norleucine;
N-(3-trifluoromethylbenzenesulfonyl)-1,2,3,4-tetrahydroisoquinoline-3(S)-carbonyl-(L)-norleucine;
N-(2-thienylsulfonyl)-1,2,3,4-tetrahydroisoquinoline-3(S)-carbonyl-(L)-norleucine;
N-(3,4-dimethoxybenzenesulfonyl)-1,2,3,4-tetrahydroisoquinoline-3(S)-carbonyl-(L)-N-methylleucine;

N-(3,4-dimethoxybenzenesulfonyl)-1,2,3,4-tetrahydroisoquinoline-3(S)-carbonyl-(L)-citrulline;
N-(3,5-dichlorobenzenesulfonyl)-(L)-prolyl-(L)-(3-iodo) tyrosine;
N-(3,5-dichlorobenzenesulfonyl)-(L)-prolyl-(L)-3-(3-pyridyl)alanine;
N-(3,5-dichlorobenzenesulfonyl)-(L)-prolyl-(L)-phenylalanine;
N-(3,5-dichlorobenzenesulfonyl)-(L)-prolyl-(L)-glutamic acid;
N-(3,5-dichlorobenzenesulfonyl)-(L)-prolyl-(L)-arginine;
N-(N-(3,5-dichlorobenzenesulfonyl)-(L)-prolyl)-1-aminocyclopentane-1-carboxylic acid;
N-(3,5-dichlorobenzenesulfonyl)-(L)-prolyl-(L)-3-(3,4-dichlorophenyl)alanine;
N-(3,5-dichlorobenzenesulfonyl)-(L)-prolyl-(L)-3-(2-naphthyl)alanine, ethyl ester;
N-(3,5-dichlorobenzenesulfonyl)-(L)-prolyl-(L)-3-(4-bromophenyl)alanine;
N-(3,5-dichlorobenzenesulfonyl)-(L)-prolyl-(L)-3-(4-nitrophenyl)alanine;
N-(3,5-dichlorobenzenesulfonyl)-(L)-prolyl-(L)-3-(4-thiazolyl)alanine;
N-(3,5-dichlorobenzenesulfonyl)-(L)-prolyl-(L)-3-(2-chlorophenyl)alanine;
N-(3,5-dichlorobenzenesulfonyl)-(L)-prolyl-(L)-3-(4-chlorophenyl)alanine;
N-(3,5-dichlorobenzenesulfonyl)-(L)-prolyl-(L)-3-(4-cyanophenyl)alanine;
N-(3,5-dichlorobenzenesulfonyl)-(L)-prolyl-(L)-tyrosine, O-sulfate;
N-(3,5-dichlorobenzenesulfonyl)-(L)-prolyl-(L)-3,5-diiodotyrosine;
N-(3,5-dichlorobenzenesulfonyl)-(L)-prolyl-(L)-tyrosine;
N-(3,5-dichlorobenzenesulfonyl)-(L)-prolyl-(L)-aspartic acid;
N-(3,5-dichlorobenzenesulfonyl)-(L)-prolyl-(L)-tryptophan;
N-(3,5-dichlorobenzenesulfonyl)-(L)-prolyl-(L)-methionine;
N-(3,4-dimethoxybenzenesulfonyl)-(L)-prolyl-(L)-norleucine;
N-(3,5-di(trifluoromethyl)benzenesulfonyl)-(L)-prolyl-(L)-3-(2-naphthyl)alanine;
N-(3,4-dimethoxybenzenesulfonyl)-(L)-thiaprolyl-(L)-3-(2-naphthyl)alanine;
N-(3,4-dimethoxybenzenesulfonyl)-(L)-thiaprolyl-(L)-norleucine;
N-(3,5-dichlorobenzenesulfonyl)-(L)-thiaprolyl-(L)-3-(2-naphthyl)alanine;
N-(3,4-dimethoxybenzenesulfonyl)-(L)-pipecolyl-(L)-norleucine;
N-(3,4-dimethoxybenzenesulfonyl)-(L)-pipecolyl-(L)-norleucine, ethyl ester, N-(3,5-dichlorobenzenesulfonyl)-(L)-pipecolyl-(L)-homophenylalanine;
N-(3,5-dichlorobenzenesulfonyl)-(L)-pipecolyl-(L)-(3-iodo)tyrosine;
N-(3,5-dichlorobenzenesulfonyl)-(L)-pipecolyl-(L)-3-(2-naphthyl)alanine;
N-(3,5-di(trifluoromethyl)benzenesulfonyl)-(L)-pipecolyl-(L)-3-(2-naphthyl)alanine;
N-(3,4-dimethoxybenzenesulfonyl)-(L)-pipecolyl-(L)-3-(2-naphthyl)alanine, ethyl ester;
N-(3,4-dimethoxybenzenesulfonyl)-(L)-octahydroisoquinoline-3-carbonyl-(L)-norleucine;
N-(3,4-dimethoxybenzenesulfonyl)-azetidine-2-carbonyl-(L)-norleucine;
N-(3,5-dichlorobenzenesulfonyl)-(L)4(S)-hydroxyprolyl-(L)-3-(2-naphthyl)alanine;
N-(3,4-dimethoxybenzenesulfonyl)-(L)-4(S)-hydroxyprolyl-(L)-norleucine;
N-(3,4-dimethoxybenzenesulfonyl)-(L)-3,4-dehydroprolyl-(L)-norleucine;
N-(3-bis(N,N-benzenesulfonyl)aminobenzenesulfonyl)-(L)-prolyl-(L)-norleucine;
N-(3,5-dichlorobenzenesulfonyl)-(L)-prolyl-(L)-3-(4-pyridyl)alanine;
N-(3,5-dichlorobenzenesulfonyl)-(L)-4(R)-aminoprolyl-(L)-3-(2-naphthyl)alanine;
N-(3,5-dichlorobenzenesulfonyl)-(L)-3,4-dehydroprolyl-(L)4-fluorophenylalanine;
N-(3-chlorobenzenesulfonyl)-(L)-prolyl-(L)-4-fluorophenylalanine;
N-(3,5-dichlorobenzenesulfonyl)-(L)-4(R)-hydroxyprolyl-(L)4-fluorophenylalanine;
N-(3,5-dichlorobenzenesulfonyl)-(L)-thiaprolyl-(L)-tyrosine;
N-(3,5-dichlorobenzenesulfonyl)-(L)-thiaprolyl-(L)-3-iodotyrosine;
N-(3-fluorobenzenesulfonyl)-(L)-thiaprolyl-(L)-3-(2-naphthyl)alanine;
N-(3-fluorobenzenesulfonyl)-(L)-pipecolyl-(L)-3-(2-naphthyl)alanine;
N-(3-fluorobenzenesulfonyl)-(L)-thiaprolyl-(L)-4-fluorophenylalanine;
N-(3-fluorobenzenesulfonyl)-(L)-prolyl-(L)-4-fluorophenylalanine;
N-(3-chlorobenzenesulfonyl)-(L)-3,4-dehydroprolyl-(L)-4-fluorophenylalanine;
N-(3-fluorobenzenesulfonyl)-(L)-4(R)-hydroxyprolyl-(L)-4-fluorophenylalanine;
N-(3-chlorobenzenesulfonyl)-(L)-4(R)-hydroxyprolyl-(L)4-fluorophenylalanine;
N-(3,5-dichlorobenzenesulfonyl)-(L)-pipecolyl-(L)-4-fluorophenylalanine;
N-(3-fluorobenzenesulfonyl)-(L)-3,4-dehydroprolyl-(L)-tyrosine;
N-(4,5-dichloro-2-thiophenesulfonyl)-(L)-prolyl-(L)-tyrosine;
N-(3-fluorobenzenesulfonyl)-(L)-4(R)-hydroxyprolyl-(L)-tyrosine;
N-(3-chlorobenzenesulfonyl)-(L)-4(R)-hydroxyprolyl-(L)-tyrosine;
N-(3-fluorobenzenesulfonyl)-(L)-pipecolyl-(L)-4-fluorophenylalanine;
N-(3-fluorobenzenesulfonyl)-(L)-4(R)-hydroxyprolyl-(L)-tyrosine, O-tert-butyl ether;
N-(3-chlorobenzenesulfonyl)-(L)-4(R)-hydroxyprolyl-(L)-tyrosine, O-tert-butyl ether;
N-(4,5-dichloro-2-thiophenesulfonyl)-(L)-3,4-dehydroprolyl-(L)-tyrosine
N-(3,5-dichlorobenzenesulfonyl)-(L)-3(S)-methyl-prolyl-(L)-4-fluorophenylalanine;
N-(4,5-dichloro-2-thiophenesulfonyl)-(L)-3,4-dehydroprolyl-(L)-tyrosine;
N-(3-fluorobenzenesulfonyl)-(L)-3,4-dehydroprolyl-(L)-tyrosine, O-tert-butyl ether;
N-(3-chlorobenzenesulfonyl)-(L)-3,4-dehydroprolyl-(L)-tyrosine, O-tert-butyl ether;
N-(3-chlorobenzenesulfonyl)-(L)-2(S)-methyl-prolyl-(L)-4-fluorophenylalanine;
N-(3-chlorobenzenesulfonyl)-(L)-2(S)-methyl-prolyl-(L)-tyrosine;
N-(3-chlorobenzenesulfonyl)-(L)-2(S)-methyl-prolyl-(L)-tyrosine, O-tert-butyl ether;

N-(3,5-dichlorobenzenesulfonyl)-(L)-2(S)-methyl-prolyl-(L)-tyrosine;
N-(3-fluorobenzenesulfonyl)-(L)-prolyl-(L)-3-iodotyrosine;
N-(3-chlorobenzenesulfonyl)-(L)-prolyl-(L)-3-iodotyrosine;
N-(3-fluorobenzenesulfonyl)-(L)-prolyl-(L)-3-phenylalanine;
N-(3-chlorobenzenesulfonyl)-(L)-prolyl-(L)-phenylalanine;
N-(3,5-dichlorobenzenesulfonyl)-(L)-prolyl-(L)-phenylalanine;
N-(3-fluorobenzenesulfonyl)-(L)-4(R)-hydroxyprolyl-(L)-phenylalanine;
N-(3-chlorobenzenesulfonyl)-(L)-4(R)-hydroxyprolyl-(L)-phenylalanine;
N-(4,5-dichloro-2-thiophenesulfonyl)-(L)-3,4-dehydroprolyl-(L)-3-(4-pyridyl)alanine;
N-(4,5-dichloro-2-thiophenesulfonyl)-(L)-thiaprolyl-(L)-3-(4-pyridyl)alanine;
N-(4,5-dichloro-2-thiophenesulfonyl)-(L)-3,4-dehydroprolyl-(L)-4-fluorophenyl-alanine;
N-(3,5-dichlorobenzenesulfonyl)-(L)-4(R)-hydroxyprolyl-(L)-phenylalanine;
N-(3-trifluoromethylbenzenesulfonyl)-(L)-prolyl-(L)-4-fluorophenylalanine;
N-(3-trifluoromethylbenzenesulfonyl)-(L)-thiaprolyl-(L)-4-fluorophenylalanine;
N-(3-fluorobenzenesulfonyl)-(L)-3,4-dehydroprolyl-(L)-4-fluorophenylalanine;
N-(3,5-dichlorobenzenesulfonyl)-(L)-prolyl-(L)-tyrosine, O-phosphoric acid;
N-(3-chlorobenzenesulfonyl)-(L)-4(R)-aminoprolyl-(L)-tyrosine;
N-(4,5-dichloro-2-thiophenesulfonyl)-(L)-thiaprolyl-(L)-tyrosine;
N-(N₁-methyl-4-imidazolesulfonyl)-(L)-prolyl-(L)-4-fluorophenylalanine;
N-(3,5-dichlorobenzenesulfonyl)-(D)-prolyl-(D)-4-fluorophenylalanine;
N-(4,5-dichloro-2-thiophenesulfonyl)-(L)-4(R)-aminoprolyl-(L)-3-(4-pyridyl)alanine;
N-(5-(5-trifluoromethyl-2-pyridylsulfonyl)-2-thiophenesulfonyl)-(L)-prolyl-(L)-4-fluorophenylalanine;
N-(5-(N-(4-chlorobenzoyl)aminomethyl))-2-thiophenesulfonyl)-(L)-prolyl-(L)-4-fluorophenylalanine;
N-(5-(3-(1'-methyl-5-trifluoromethyl-pyrazoyl))-2-thiophenesulfonyl)-(L)-prolyl-(L)-4-fluorophenylalanine;
N-(3-fluorobenzenesulfonyl)-2(S)-methylprolyl-(L)-O-tert-butyl-tyrosine;
N-(3-fluorobenzenesulfonyl)-(L)4(R)-aminoprolyl-(L)-4-fluorophenylalanine;
N-(3,5-dichlorobenzenesulfonyl)-(L)-4(R)-aminoprolyl-(L)-4-fluorophenylalanine;
N-(3-chlorobenzenesulfonyl)-(L)-4(R)-aminoprolyl-(L)-4-fluorophenylalanine;
N-(3,5-dichlorobenzenesulfonyl)-(L)-4(S)-aminoprolyl-(L)-4-fluorophenylalanine;
N-(3-chlorobenzenesulfonyl)-(L)-thiaprolyl-(L)-4-fluorophenylalanine;
N-(4-bromo-5-chloro-2-thiophenesulfonyl)-(L)-prolyl-(L)-4-fluorophenylalanine;
N-(4,5-dichloro-2-thiophenesulfonyl)-(L)-prolyl-(L)-4-fluorophenylalanine;
N-(3,5-dichlorobenzenesulfonyl)-(L)-thiaprolyl-(L)-3,5-di iodotyrosine;
N-(5-benzoylaminomethyl-2-thiophenesulfonyl)-(L)-prolyl-(L)-4-fluorophenyl-alanine;
N-(3-chlorobenzenesulfonyl)-(L)-prolyl-(L)-O-tert-butyl-tyrosine;
N-(5-benzenesulfonyl-2-thiophenesulfonyl)-(L)-prolyl-(L)-4-fluorophenylalanine;
N-(3-bromo-5-chloro-2-thiophenesulfonyl)-(L)-prolyl-(L)-4-fluorophenylalanine;
N-(3-chlorobenzenesulfonyl)-(L)-3,4-dehydroprolyl-(L)-tyrosine;
N-(3,5-dichlorobenzenesulfonyl)-(L)-prolyl-(L)-homophenylalanine;
N-(4-benzenesulfonyl-2-thiophenesulfonyl)-(L)-prolyl-(L)-O-tert-butyl-tyrosine;
N-(5-benzoylaminomethyl-2-thiophenesulfonyl)-(L)-prolyl-(L)-O-tert-butyl-tyrosine;
N-(5-benzenesulfonyl-2-thiophenesulfonyl)-(L)-prolyl-(L)-O-tert-butyl-tyrosine;
N-(3-fluorobenzenesulfonyl)-(L)-thiaprolyl-(L)-O-tert-butyl-tyrosine;
N-(3,5-dichlorobenzenesulfonyl)-(L)-prolyl-(L)-cysteine, amide;
N-(1-methyl-4-imidazolylsulfonyl)-(L)-prolyl-(L)-O-tert-butyl-tyrosine;
N-(5-(4-trifluoromethylbenzenesulfonyl)-2-thiophenesulfonyl)-(L)-prolyl-(L)-O-tert-butyl-tyrosine;
N-(3-bromobenzenesulfonyl)-(L)-prolyl-(L)-O-tert-butyl-tyrosine;
N-(4,5-dichloro-2-thiophenesulfonyl)-(L)-prolyl-(L)-3-fluorophenylalanine;
N-(5-chloro-2-thiophenesulfonyl)-(L)-prolyl-(L)4-fluorophenylalanine;
N-(3-chlorobenzenesulfonyl)-(L)-thiaprolyl-(L)-tyrosine;
N-(3,5-dichlorobenzenesulfonyl)-(L)-2(S)-methylprolyl-(L)-O-tert-butyl-tyrosine;
N-(3-chlorobenzenesulfonyl)-(L)-4(R)-hydroxyprolyl-(L)-tyrosine-O-sulfate;
N-(3-chlorobenzenesulfonyl)-(L)-thiaprolyl-(L)-tyrosine-O-sulfate;
N-(3,5-dichlorobenzenesulfonyl)-(L)-prolyl-(L)-cysteine;
N-(3,5-dichlorobenzenesulfonyl)-(L)-prolyl-(L)-N-methyl-isoleucine;
N-(3,5-dichlorobenzenesulfonyl)-(L)-4(R)-aminoprolyl-(L)-O-tert-butyl-tyrosine;
N-(3-chlorobenzenesulfonyl)-(L)-4(R)-aminoprolyl-(L)-O-tert-butyl-tyrosine;
N-(3-cyanobenzenesulfonyl)-(L)-prolyl-(L)-tyrosine;
N-(4,5-dichloro-2-thiophenesulfonyl)-(L)-4(R)-aminoprolyl-(L)-O-tert-butyl-tyrosine;
N-(4,5-dichloro-2-thiophenesulfonyl)-(L)-4(R)-aminoprolyl-(L)-4-fluorophenyl-alanine;
N-(3-fluorobenzenesulfonyl)-(L)-5(R)-phenyl-prolyl-(L)-4-fluorophenylalanine;
N-(3,5-dichlorobenzenesulfonyl)-(L)-3(R)-phenyl-prolyl-(L)-4-iodophenylalanine;
N-(3,5-dichlorobenzenesulfonyl)-1,2,3,4-tetrahydroisoquinoline-1-carbonyl-(L)-4-fluorophenylalanine;
N-(3,5-dichlorobenzenesulfonyl)-1,3-dihydro isoindolyl-1-carbonyl-(L)-4-fluorophenylalanine;
N-(3-ethoxycarbonyl-benzenesulfonyl)-(L)-prolyl-(L)-O-tert-butyl-tyrosine;
N-(3-(4-benzophenonyl-carbonylamino)-benzenesulfonyl)-(L)-prolyl-(L)-O-tert-butyl-tyrosine;
N-(3,5-dichlorobenzenesulfonyl)-[3.1.0]-3-azabicyclohexane-2-carbonyl-(L)-4-fluorophenylalanine;
N-(3,5-dichlorobenzenesulfonyl))-(L)-prolyl-(L)-3-(2-naphthyl)alanine;
N-(3,4-dimethoxybenzenesulfonyl))-(L)-pipecolyl-(L)-tryptophan;
N-[3,5-di(trifluoromethyl)benzenesulfonyl)]-(L)-prolyl-(L)-norleucine;

N-(3,5-dichlorobenzenesulfonyl))-(L)-prolyl-(L)-norleucine;
N-(3-trifluoromethylbenzenesulfonyl))-(L)-prolyl-(L)-norleucine;
N-(3-chlorobenzenesulfonyl))-(L)-prolyl-(L)-norleucine;
N-(3-trifluoromethylbenzenesulfonyl))-(L)-prolyl-(L)-3-(2-naphthyl)alanine;
N-(3-nitrobenzenesulfonyl))-(L)-prolyl-(L)-norleucine;
N-(3-cyanobenzenesulfonyl))-(L)-prolyl-(L)-norleucine;
N-(3,5-dichlorobenzenesulfonyl))-(L)-prolyl-(L)-tryptophan;
N-(3-methylbenzenesulfonyl))-(L)-prolyl-(L)-norleucine;
N-(3,5-dichlorobenzenesulfonyl))-(L)-3(S)-methyl-prolyl-(L)-3-(2-naphthyl)alanine;
N-(3-chlorobenzenesulfonyl)-(L)-prolyl-(L)-3-(2-naphthyl)alanine;
N-(3-fluorobenzenesulfonyl))-(L)-prolyl-(L)-3-(2-naphthyl)alanine;
N-(3,5-dichlorobenzenesulfonyl))-(L)-2-methyl-prolyl-(L)-3-(2-naphthyl)alanine;
N-(3-fluorobenzenesulfonyl)-(L)-5,5-dimethyl-prolyl-(L)-3-(2-naphthyl)alanine;
N-(3-fluorobenzenesulfonyl)-(L)-prolyl-(L)-4-iodophenylalanine;
N-(3-fluorobenzenesulfonyl)-(L)-2(S)-methyl-prolyl-(L)-4-fluorophenylalanine;
N-(3,5-dichlorobenzenesulfonyl)-(L)-2(S)-methyl-prolyl-(L)-4-fluorophenylalanine;
N-(3,5-dichlorobenzenesulfonyl)-(L)-prolyl-(L)-phenylalaninamide-N-methylsulfonamide;
N-(3,5-dichlorobenzenesulfonyl)-(L)-2(S)-methyl-prolyl-(L)-4-iodophenylalanine;
N-(3-fluorobenzenesulfonyl)-(L)-prolyl-(L)-phenylalanine;
N-(3,5-dichlorobenzenesulfonyl)-(L)-5-methylprolyl-(L)-4-fluorophenylalanine;
N-(3,5-dichlorobenzenesulfonyl)-3-phenylazetidinylcarbonyl-(L)4-fluoro-phenylalanine;
N-(3,5-dichlorobenzenesulfonyl)-(L)-2(S)-allylprolyl-(L)-4-fluorophenylalanine;
N-(3,5-dichlorobenzenesulfonyl)-(L)-2(S)-methyl-prolyl-(L)-phenylalanine;
N-(3-trifluoromethylbenzenesulfonyl)-(L)-2(S)-methyl-prolyl-(L)-4-nitro-phenylalanine;
N-(3,5-dichlorobenzenesulfonyl)-(L)-3(R)-methyl-prolyl-(L)-4-fluorophenylalanine;
N-(3,5-dichlorobenzenesulfonyl)-(L)-2(S)-methyl-prolyl-(L)-4-cyanophenylalanine;
N-(3,5-dichlorobenzenesulfonyl)-(L)-2(S)-methyl-prolyl-(L)4-(aminocarbonyl)-phenylalanine;
N-(3,5-dichlorobenzenesulfonyl)-(L)-3(R)-methyl-prolyl-(L)-4-(N-t-butoxycarbonylaminomethyl)-phenylalanine;
N-(3,5-dichlorobenzenesulfonyl)-(L)-3(R)-methyl-prolyl-(L)-4-(aminomethyl)-phenylalanine;
N-(3-tri fluoro methylphenyl sulfonyl)-(L)-2 (S)-methyl-prolyl-(L)-4-acetaminophenylalanine;
N-(3-trifluoromethylphenylsulfonyl)-(L)-2(S)-methyl-prolyl-(L)-4-(N'-(2-toluyl)ureido)phenylalanine;
N-(3-trifluoromethylphenylsulfonyl)-(L)-2(S)-methyl-prolyl-(L)-4-(N'-(4'-fluorophenylsulfonyl)ureido)phenylalanine;
N-(3-trifluoromethylphenylsulfonyl)-(L)-2(S)-methyl-prolyl-(L)-4-(ethoxycarbonyl)aminophenylalanine;
N-(3-trifluoromethylphenylsulfonyl)-(L)-2(S)-methyl-prolyl-(L)-4-(4'-(N'-(2-toluyl)ureido)phenylacetyl)aminophenylalanine;
N-(3-trifluoromethylphenylsulfonyl)-(L)-2(S)-methyl-prolyl-(L)-4-(4'-fluorophenylsulfonyl)aminophenylalanine;
N-(3-trifluoromethylphenylsulfonyl)-(L)-2(S)-methyl-prolyl-(L)-4-(phenylacetyl)aminophenylalanine;
N-(3-trifluoromethylphenylsulfonyl)-(L)-2(S)-methyl-prolyl-(L)4-(4'-fluorobenzoyl)aminophenylalanine;
N-(3-trifluoromethylphenylsulfonyl)-(L)-2(S)-methyl-prolyl-(L)-4-(isobutyloxycarbonyl)aminophenylalanine;
N-(3-trifluoromethylphenylsulfonyl)-(L)-2(S)-methyl-prolyl-(L)4-methylsulfonylaminophenylalanine;
N-(3-trifluoromethylphenylsulfonyl)-(L)-2(S)-methyl-prolyl-(L)-4-(N'-(4-fluorophenyl)ureido)phenylalanine;
N-(3-trifluoromethylbenzenesulfonyl)-(L)-2(S)-methyl-prolyl-(L)-4-(N-(1,1-dioxo-1,2-isothiazolidinyl)-phenylalanine;
N-(3-trifluoromethylphenylsulfonyl)-(L)-2(S)-methyl-prolyl-(L)-4-(N'-(4-(2-oxo-1-pyrrolidinyl)-phenylalanine;
N-(3,5-dichorobenzenesulfonyl)-(L)-prolyl-(L)-4-(4'-fluorobenzoyl)phenylalanine;
N-(3,5-dichlorobenzenesulfonyl)-(L)-prolyl-(L)-4'-(2-methoxybenzoyl)phenylalanine;
N-(3,5-dichorobenzenesulfonyl)-(L)-2(S)-methyl-prolyl-(L)-4-(4'-fluorobenzoyl)phenylalanine;
N-(3,5-dichlorobenzenesulfonyl)-(L)-prolyl-(L)-4-(4-fluorobenzyl)phenyl alanine;
N-(3,5-dichlorobenzenesulfonyl)-(L)-prolyl-(L)-4-(2-methoxybenzyl)phenylalanine;
N-(3,5-dichlorobenzenesulfonyl)-(L)-prolyl-(L)-4-(2-nitrophenoxy)-phenylalanine;
N-(3,5-dichlorobenzenesulfonyl)-(L)-prolyl-(L)-4-(4-nitrophenoxy)-phenylalanine;
N-(3,5-dichlorobenzenesulfonyl)-(L)-2(S)-methyl-prolyl-(L)-4-(2-nitrophenoxy)-phenylalanine;
N-(3,5-dichlorobenzenesulfonyl)-(L)-prolyl-(L)-4-(2-aminophenoxy)-phenylalanine;
N-(3,5-dichlorobenzenesulfonyl)-(L)-prolyl-(L)-4-(2-acetylaminophenoxy)-phenylalanine;
N-(3,5-dichlorobenzenesulfonyl)-(L)-prolyl-(L)-4-(4-acetylaminophenoxy)-phenylalanine;
N-(3,5-dichlorobenzenesulfonyl)-(L)-2(S)-methylprolyl-(L)-4-(2-acetylaminophenoxy)-phenylalanine;
N-(3,5-dichlorobenzenesulfonyl)-2-(S)-methyl-(L)-prolyl-4-(2-cyanophenoxy)-phenylalanine;
N-(3,5-dichlorobenzenesulfonyl)-2-(S)-methyl-(L)-prolyl-4-(4-cyanophenoxy)-phenylalanine;
N-(3,5-dichlorobenzenesulfonyl)-(L)-prolyl-(L)-O-tert-butyl-tyrosine;
N-(3,5-dichlorobenzenesulfonyl)-(L)-prolyl-(L)-O-methyl-tyrosine;
N-(3,5-dichlorobenzenesulfonyl)-(L)-prolyl-(L)-O-benzyl-tyrosine;
N-(3,5-dichlorobenzenesulfonyl)-(L)-prolyl-(L)-O-n-butyl-tyrosine;
N-(3,5-dichlorobenzenesulfonyl)-(L)-prolyl-(L)-O-cyanomethyl-tyrosine;
N-(3,5-dichlorobenzenesulfonyl)-(L)-prolyl-(L)-O-(2-methoxyethyl)-tyrosine;
N-(3,5-dichlorobenzenesulfonyl)-(L)-prolyl-(L)-O-(2-ethoxyethyl)-tyrosine;
N-(3,5-dichlorobenzenesulfonyl)-(L)-prolyl-(L)-O-(1-pyrrolidinylcarbonyl)-tyrosine;
N-(3,5-dichlorobenzenesulfonyl)-(L)-prolyl-(L)-O-(tert-butyl acetate)-tyrosine;
N-(3,5-dichlorobenzenesulfonyl)-(L)-prolyl-(L)-O-(4-morpholinyl-carbonyl)-tyrosine;
N-(3,5-dichlorobenzenesulfonyl)-(L)-prolyl-(L)-O-(1-(2-propanonyl)-tyrosine;
N-(3,5-dichlorobenzenesulfonyl)-(L)-2(S)-methyl-prolyl-(L)-O-(1-pyrrolidinylcarbonyl)-tyrosine;

N-(3,5-dichlorobenzenesulfonyl)-(L)-2(S)-methyl-prolyl-(L)-O-(tert-butyl acetate)-tyrosine;
N-(3,5-dichlorobenzenesulfonyl)-(L)-2(S)-methyl-prolyl-(L)-O-(2-ethoxyethyl)-tyrosine;
N-(3,5-dichlorobenzenesulfonyl)-(L)-prolyl-(L)-O-(acetic acid)-tyrosine, methyl ester;
N-(3,5-dichlorobenzenesulfonyl)-(L)-prolyl-(L)-O-(acetic acid)-tyrosine;
N-(3,5-dichlorobenzenesulfonyl)-(L)-2(S)-methyl-prolyl-(L)-O-(1-(2-propanonyl)-tyrosine;
N-(3,5-dichlorobenzenesulfonyl)-(L)-2(S)-methyl-prolyl-(L)-O-(1-pyrrolidinylcarbonyl)-tyrosine, methyl ester;
N-(3,5-dichlorobenzenesulfonyl)-(L)-2(S)-methyl-prolyl-(L)-O-(4-morpholinyl-carbonyl)-tyrosine;
N-(3,5-dichlorobenzenesulfonyl)-(L)-prolyl-(L)-O-(2-pyrrolylcarbonyl)-tyrosine;
N-(3,5-dichlorobenzenesulfonyl)-(L)-2(S)-methyl-prolyl-(L)-O-(N-phenyl-N-methylaminocarbonyl)-tyrosine;
N-(3,5-dichlorobenzenesulfonyl)-(L)-2(S)-methyl-prolyl-(L)-O-(N,N-diethyl-aminocarbonyl)-tyrosine;
N-(3-chlorobenzenesulfonyl)-(L)-2(S)-methyl-prolyl-(L)-O-(4-morpholinyl-carbonyl)-tyrosine;
N-(3,5-dichlorobenzenesulfonyl)-(L)-2(S)-methyl-prolyl-(L)-O-(N,N-diisopropyl-aminocarbonyl)-tyrosine;
N-(3,5-dichlorobenzenesulfonyl)-(L)-prolyl-(L)-O-(benzoyl)-tyrosine;
N-(3,5-dichlorobenzenesulfonyl)-(L)-prolyl-(L)-O-(cyclopentanoyl)-tyrosine;
N-(3,5-dichlorobenzenesulfonyl)-(L)-prolyl-(L)-O-(5-tetrazolyl)methyl-tyrosine;
N-(3,5-dichlorobenzenesulfonyl)-(L)-2(S)-methyl-prolyl-(L)-Nε-benzyl-histidine; and
N-(3,5-dichlorobenzenesulfonyl)-(L)-2(S)-methyl-prolyl-(L)-4-(5-((1H,3H)-1,3-dimethylpyrimidine-2,4-dione))-phenylalanine.

12. A compound selected from the group consisting of:
N-(2,4-dinitrobenzenesulfonyl)-1,2,3,4-tetrahydroisoquinoline-3(S)-carbonyl-(L)-norleucine;
N-(2-mesitylenesulfonyl)-1,2,3,4-tetrahydroisoquinoline-3(S)-carbonyl-(L)-norleucine;
N-(4-chlorobenzenesulfonyl)-1,2,3,4-tetrahydroisoquinoline-3 (S)-carbonyl-(L)-norleucine;
N-(N'-acetylsulfanilyl)-1,2,3,4-tetrahydroisoquinoline-3(S)-carbonyl-(L)-norleucine;
N-(4-fluorobenzenesulfonyl)-1,2,3,4-tetrahydroisoquinoline-3(S)-carbonyl-(L)-norleucine;
N-(4-nitrobenzenesulfonyl)-1,2,3,4-tetrahydroisoquinoline-3(S)-carbonyl-(L)-norleucine;
N-(4-trifluoromethylbenzenesulfonyl)-1,2,3,4-tetrahydroisoquinoline-3(S)-carbonyl-(L)-norleucine;
N-(2,6-dichlorobenzenesulfonyl)-1,2,3,4-tetrahydroisoquinoline-3(S)-carbonyl-(L)-norleucine;
N-(2,4-difluorobenzenesulfonyl)-1,2,3,4-tetrahydroisoquinoline-3(S)-carbonyl-(L)-norleucine;
N-(2-cyanobenzenesulfonyl)-1,2,3,4-tetrahydroisoquinoline-3(S)-carbonyl-(L)-norleucine;
N-(2-trifluoromethylbenzenesulfonyl)-1,2,3,4-tetrahydroisoquinoline-3(S)-carbonyl-(L)-norleucine;
N-(2,4-dichlorobenzenesulfonyl)-1,2,3,4-tetrahydroisoquinoline-3(S)-carbonyl-(L)-norleucine;
N-(4-cyanobenzenesulfonyl)-1,2,3,4-tetrahydroisoquinoline-3(S)-carbonyl-(L)-norleucine;
N-(4-iodobenzenesulfonyl)-1,2,3,4-tetrahydroisoquinoline-3(S)-carbonyl-(L)-norleucine;
N-(5-benzenesulfonyl-2-thiophenesulfonyl)-(L)-prolyl-(L)-O-tert-butyl-tyrosine;
N-(3-fluorobenzenesulfonyl)-(L)-thiaprolyl-(L)-O-tert-butyl-tyrosine;
N-(4-methoxybenzenesulfonyl)-(L)-prolyl-(L)-O-tert-butyl-tyrosine;
N-(1(R)-(+)-10-camphorsulfonyl)-(L)-prolyl-(L)-O-tert-butyl-tyrosine;
N-(1(S)-(+)-10-camphorsulfonyl)-(L)-prolyl-(L)-O-tert-butyl-tyrosine;
N-(4-(fluorescien-4-carbonylamino)benzenesulfonyl)-(L)-prolyl-(L)-O-tert-butyl-tyrosine;
N-(4-iodobenzenesulfonyl)-(L)-prolyl-(L)4-benzoyl-phenylalanine;
N-(3-(6-(biotinylamino)-n-hexanoyl)-aminobenzenesulfonyl)-(L)-prolyl-(L)-O-tert-butyl-tyrosine;
N-(4-nitrobenzenesulfonyl))-(L)-prolyl-(L)-norleucine;
N-(4-(benzoylamino)benzenesulfonyl))-(L)-prolyl-(L)-norleucine;
N-(4-methoxy-3,5-dinitrobenzenesulfonyl)-(L)-prolyl-(L)-norleucine;
N-(4-N'-phenylureidobenzenesulfonyl)-(L)-prolyl-(L)-3-(2-naphthyl)alanine;
N-(4-N'-(2-toluyl)ureidobenzenesulfonyl)-(L)-prolyl-(L)-3-(2-naphthyl)alanine;
N-(4-N'-benzylureidobenzenesulfonyl)-(L)-prolyl-(L)-3-(2-naphthyl)alanine;
N-benzenesulfonyl-(L)-prolyl-2-amino-2-norbornanecarboxylic acid;
N-benzenesulfonyl-(L)-prolyl-3(R)-methyl-phenylalanine;
N-benzenesulfonyl-(L)-prolyl-(L)-2,3-methano-phenylalanine; and
N-benzenesulfonyl-(L)-prolyl-(D)-2,3-methano-phenylalanine.

* * * * *